(12) United States Patent
Miller et al.

(10) Patent No.: US 11,834,433 B2
(45) Date of Patent: *Dec. 5, 2023

(54) COMPOUNDS

(71) Applicant: INFLAZOME LIMITED, Dublin (IE)

(72) Inventors: David Miller, Cambridge (GB); Jimmy Van Wiltenburg, Groningen (NL); Matthew Cooper, Cambridge (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/977,251

(22) PCT Filed: Mar. 1, 2019

(86) PCT No.: PCT/EP2019/055140
§ 371 (c)(1),
(2) Date: Sep. 1, 2020

(87) PCT Pub. No.: WO2019/166627
PCT Pub. Date: Sep. 6, 2019

(65) Prior Publication Data
US 2021/0040065 A1    Feb. 11, 2021

(30) Foreign Application Priority Data

Mar. 2, 2018  (GB) ..................... 1803411
Feb. 20, 2019 (GB) ..................... 1902318

(51) Int. Cl.
*C07D 401/12* (2006.01)
*C07D 231/18* (2006.01)
*C07D 405/04* (2006.01)
*C07D 405/14* (2006.01)

(52) U.S. Cl.
CPC ......... *C07D 401/12* (2013.01); *C07D 231/18* (2013.01); *C07D 405/04* (2013.01); *C07D 405/14* (2013.01)

(58) Field of Classification Search
CPC .. C07D 231/18; C07D 401/12; C07D 405/04; C07D 405/14; A61K 31/415
See application file for complete search history.

(56) References Cited

U.S. PATENT DOCUMENTS

| | | |
|---|---|---|
| 2011/0294780 A1 | 12/2011 | Bignan et al. |
| 2018/0044287 A1 | 2/2018 | O'Neill et al. |
| 2020/0399242 A1 | 12/2020 | Miller et al. |
| 2020/0399243 A1 | 12/2020 | Miller et al. |
| 2020/0407340 A1 | 12/2020 | Cooper et al. |
| 2021/0002274 A1 | 1/2021 | Cooper et al. |
| 2021/0047302 A1 | 2/2021 | Cooper et al. |
| 2022/0106289 A1 | 4/2022 | Cooper et al. |
| 2022/0163539 A1 | 5/2022 | Cooper et al. |

FOREIGN PATENT DOCUMENTS

| | | |
|---|---|---|
| EP | 1236468 A1 | 9/2002 |
| EP | 2138482 A1 | 12/2009 |
| GB | 2104069 A | 3/1983 |
| WO | WO 1994/026702 A1 | 11/1994 |
| WO | WO 1998/032733 A1 | 7/1998 |
| WO | WO 2001/019390 A1 | 3/2001 |
| WO | WO 2002/050032 A1 | 6/2002 |
| WO | WO 2005/082863 A1 | 9/2005 |
| WO | WO 2005/082864 A1 | 9/2005 |
| WO | WO 2006/075955 A1 | 7/2006 |
| WO | WO 2008/014186 A1 | 1/2008 |
| WO | WO 2008/099794 A1 | 8/2008 |
| WO | WO 2011/149841 A1 | 12/2011 |
| WO | WO 2016/131098 A1 | 8/2016 |
| WO | WO 2017/140778 A1 | 8/2017 |
| WO | WO 2017/184604 A1 | 10/2017 |
| WO | WO 2018/215818 A1 | 11/2018 |
| WO | WO 2019/008025 A1 | 1/2019 |
| WO | WO 2019/008029 A1 | 1/2019 |
| WO | WO 2019/034686 A1 | 2/2019 |
| WO | WO 2019/034688 A1 | 2/2019 |
| WO | WO 2019/034690 A1 | 2/2019 |

(Continued)

OTHER PUBLICATIONS

Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Alston & Bird LLP

(57) ABSTRACT

The present invention relates to compounds of formula (I): comprising a 5-membered nitrogen-containing heteroaryl ring A, wherein the heteroaryl ring A is substituted with at least one group containing an oxygen atom, and wherein said oxygen atom is attached to the heteroaryl ring A via at least two other atoms. The present invention further relates to salts, solvates and prodrugs of such compounds, to pharmaceutical compositions comprising such compounds, and to the use of such compounds in the treatment and prevention of medical disorders and diseases, most especially by the inhibition of NLRP3.

Formula (I)

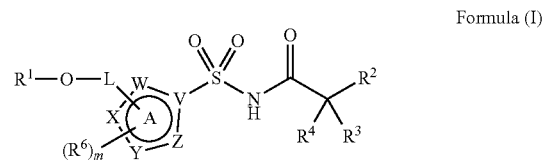

19 Claims, No Drawings

(56) References Cited

FOREIGN PATENT DOCUMENTS

| WO | WO 2019/034692 A1 | 2/2019 |
|---|---|---|
| WO | WO 2019/034693 A1 | 2/2019 |
| WO | WO 2019/034696 A1 | 2/2019 |
| WO | WO 2019/034697 A1 | 2/2019 |
| WO | WO 2019/068772 A1 | 4/2019 |
| WO | WO 2019/079119 A1 | 4/2019 |
| WO | WO 2019/092170 A1 | 5/2019 |
| WO | WO 2019/092171 A1 | 5/2019 |
| WO | WO 2019/092172 A1 | 5/2019 |
| WO | WO 2019/166619 A1 | 9/2019 |
| WO | WO 2019/166621 A1 | 9/2019 |
| WO | WO 2019/166623 A1 | 9/2019 |
| WO | WO 2019/166624 A1 | 9/2019 |
| WO | WO 2019/166627 A1 | 9/2019 |
| WO | WO 2019/166628 A1 | 9/2019 |
| WO | WO 2019/166629 A1 | 9/2019 |
| WO | WO 2019/166632 A1 | 9/2019 |
| WO | WO 2019/166633 A1 | 9/2019 |
| WO | WO 2019/206871 A1 | 10/2019 |
| WO | WO 2019/211463 A1 | 11/2019 |
| WO | WO 2020/010118 A1 | 1/2020 |
| WO | WO 2020/035464 A1 | 2/2020 |
| WO | WO 2020/035465 A1 | 2/2020 |
| WO | WO 2020/035466 A1 | 2/2020 |
| WO | WO 2020/079207 A1 | 4/2020 |
| WO | WO 2020/086728 A1 | 4/2020 |
| WO | WO 2020/104657 A1 | 5/2020 |
| WO | WO 2020/208249 A1 | 10/2020 |
| WO | WO 2021/032588 A1 | 2/2021 |
| WO | WO 2021/032591 A1 | 2/2021 |
| WO | WO 2021/043966 A1 | 3/2021 |
| WO | WO 2021/165245 A1 | 8/2021 |

OTHER PUBLICATIONS

Simone, Oncology: Introduction, Cecil Textbook of Medicine, 20th Edition, vol. 1, pp. 1004-1010, 1996.*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Razonable et al., PubMed Abstract (Herpes 10(3):60-5), 2003.*
Goff, PubMed Abstract (J Gene Med. 3(6):517-28), 2001.*
WIPO Application No. PCT/EP2019/055140, PCT International Preliminary Report on Patentability dated Sep. 8, 2020.
WIPO Application No. PCT/EP2019/055140, PCT International Search Report and Written Opinion of the International Searching Authority dated May 22, 2019.
Belikov, et al., "The interconnection between chemical structure, properties of substances and their effect on the body", MEDpressinform, Pharmaceutical Chemistry, Text Book, 4th Edition, Moscow, Chap. 2.6, 27-29, (2007), Brief statement of relevance.
Burch, et al., "Structure-activity relationships and pharmacokinetic parameters of quinoline acylsulfonamides as potent and selective antagonists of the EP4 receptor," Bioorg Med Chem Lett, 18(6):2048-2054, (2008).
CAS 1388800-35-8, Aug. 9, 2012.
CAS 1394754-16-5, Sep. 18, 2012.
CAS 1427583-89-8, Apr. 9, 2013.
CAS 1647400-37-0, Feb. 15, 2015.
CAS 1808711-66-1, Sep. 29, 2015.
CAS 2128079-36-5, Sep. 17, 2017.
CAS 2130083-93-9, Sep. 24, 2017.
CAS 2130517-27-8, Sep. 25, 2017.
CAS 900813-70-9, Aug. 11, 2006.

Clark, et al., "MF498 [N-{[4-(5,9-Diethoxy-6-oxo-6,8-dihydro-7H-pyrrolo[3,4-g]quinolin-7-yl)-3-methylbenzyl]sulfonyl}-2-(2-methoxyphenyl)acetamide], a Selective E Prostanoid Receptor 4 Antagonist, Relieves Joint Inflammation and Pain in Rodent Models of Rheumatoid and Osteoarthritis," JPET, 325(2), 425-434, (2008).
Coll, et al., "A small-molecule inhibitor of the NLRP3 inflammasome for the treatment of inflammatory diseases," Nature Medicine, 21(3): 248-255, (2015).
Disease—Wikipedia, retrieved from the internet on Feb. 2, 2022 at: https://en.wikipedia.org/wiki/Disease.
Ettmayer, et al., "Lessons learned from marketed and investigational prodrugs," J. Med. Chem., 47(10):2394-2404 (2004).
Gadakh, et al., "N-Acylated sulfonamide congeners of fosmdomycin lack any inhibitory activity against DXR," Bioorganic & Medicinal Chemistry Letters, 25: 1577-1573, (2015).
Han, "Targeted prodrug design to optimize drug delivery," AAPS Pharmsci. 2(1) Article 6: 1-11, (2000).
Himiceskij, Chemical Encyclopedia, (1983), p. 130-131 [and brief statement of relevance in English].
Li, et al "The identification of substituted benzothiophene derivatives as PGE(2) subtype 4 receptor antagonists: From acid to non-acid," Bioorg Med Chem Lett, 21(2):734-737, (2011).
Liedtke, et al., "Arylpyrrolizines as inhibitors of microsomal prostaglandin E2 synthase-1 (mPGES-1) or as dual inhibitors of mPGES-1 and 5-lipoxygenase (5-LOX)," J Med Chem, 52(15): 4968-4972, (2009).
Luo, et al., "Principles of cancer therapy: oncogene and non-oncogene addiction," Cell, 136: 823-837, (2009).
Parajuli, et al., "Prodrug as a novel approach of drug delivery—a review," Journal of Drug Delivery & Therapeutics, 5(3), pp. 5-9, (2015).
Schroder, "Could an NLRP3 inhibitor be the one drug to conquer common diseases?" Drug Discovery, Vo. 98, Issue 7, 1-11, (Feb. 2020).
Solvation—Wikipedia, retrieved from the internet on Jan. 15, 2022 at: https://en.wikipedia.org/wiki/Solvation.
Stella, "Prodrugs as theraputics," Expert Opinion of theraputic patents, 14(3): 277-286 (2004).
Testa, "Prodrug Research: futile or fertile?" Biochemical Pharmacology, 68, 2097-2106, (2004).
Zahid, et al., "Pharmacological Inhibitors of the NLRP3 Inflammasome," Front. Immunol., 10(2538): 1-10, (2019).
Zawilska, et al., "Prodrugs: a challenge for the drug development," Pharmacological reports: PR, vol. 65, No. 1, pp. 1-14, (Apr. 2013).
Zhang, et al., "New Highly PotentNLRP3 Inhibitors: Furanochalcone Velutone F Analogues," ACS Med. Chem. Lett., 13, 560-569, (Mar. 2022).
GB Application 1803412.4 Search Report dated Oct. 9, 2018.
GB Application No. 1803414.0, Search Report dated Oct. 16, 2018.
WIPO Application No. PCT/EP2019/055135, PCT International Preliminary Report on Patentability dated Sep. 17, 2020.
WIPO Application No. PCT/EP2019/055135, PCT International Search Report and Written Opinion of the International Searching Authority dated Apr. 2, 2019.
WIPO Application No. PCT/EP2019/055144 PCT International Search Report of the International Searching Authority dated Apr. 24, 2019.
WIPO Application No. PCT/EP2019/055144, PCT International Preliminary Report on Patentability dated Sep. 17, 2020.
WIPO Application No. PCT/EP2019/055146, PCT International Preliminary Report on Patentability dated Sep. 17, 2020.
WIPO Application No. PCT/EP2019/055146, PCT International Search Report and Written Opinion of the International Searching Authority dated May 23, 2019.
WIPO Application No. PCT/EP2019/055150, PCT International Preliminary Report on Patentability dated Sep. 17, 2020.
WIPO Application No. PCT/EP2019/055150, PCT International Search Report and Written Opinion of the International Searching Authority dated May 22, 2019.
WIPO Application No. PCT/EP2019/055154 PCT International Search Report of the International Searching Authority dated Jun. 14, 2019.

(56) References Cited

OTHER PUBLICATIONS

WIPO Application No. PCT/EP2019/055154, PCT International Preliminary Report on Patentability dated Sep. 17, 2020.
Alikhan, et al., "Hidradenitis suppurativa: A comprehensive review," J AM Acad Dermatol, vol. 60, No. 4, pp. 539-561, (Apr. 2009).
Allen, et al., "The NLRP3 inflammasome functions as a negative regulator of tumorigenesis during colitis-associated cancer," J Exp Med, vol. 207, No. 5, pp. 1045-1056, (Apr. 2010).
Amsler, et al., "The inflammasome as a target of modulation by DNA viruses," Future Virol., 8(4), pp. 357-370, (2013).
Basiorka, et al., The NLRP3 inflammasome functions as a driver of the myelodysplastic syndrom phenotype, Blood, vol. 128, No. 25, pp. 2960-2975, (Dec. 2016).
Braddock et al., "Targeting IL-1 in Inflammatory Disease: New Opportunities for Thereapeutic Intervention," Nature Reviews, vol. 3, (Apr. 2004).
Cook, et al., "The NLRP3 inflammasome, a target for therapy in diverse disease states," Eur. J. Immunol, 40: 595-653, (2010).
Dempsey, et al, "inhibiting the NLRP3 inflammasome with MCC950 promotes non-phlogistic clearance of amyloid-β and cognitive function in APP/PS1 mice," Brain, Behavior, and Immunity, 61, 306-316, (2017).
DeNardo, et al., "New Insights into Mechanisms Controlling the NLRP3 Inflammasome and Its Role in Lung Disease," the American Journal of Pathology, vol. 184, No. 1, pp. 42-54, (Jan. 2014).
Doyle, et al., "NLRP3 has a protective role in age-related macular degeneration through the induction of IL-18 by drusen componets," Nature Medicine, vol. 18, No. 5, pp. 791-498, (May 2012).
Duewell, et al.,"NLRP3 inflammasomes are required for atherogenesis and activated by cholesterol crystals," Nature Letters, vol. 464, doi:10.1038/nature08938, (Apr. 2010).
Fang, et al., "Increased expression of NLRP3 inflammasome componets and interleukin-18 in patients with bullous pemphigoid," Journal of Dermatological Science, 83, 116-123, (2016).
Granata, et al., "NLRP3 Inflammasome Activation in Dialyzed Chronic Kidney Disease Patients," PLoS ONE, 10(3): e0122272, (2015).
Henao-Mejia, et al., "Inflammasome-mediated dysbiosis regulates progression of NAFLD and obesity," Nature, vol. 482, pp. 170-185, (Feb. 2012).
Hu, et al., "Inflammation-induced tumorigenesis in the colon is regulated by caspase-1 and NLR4," PNAS, vol. 107, No. 50, pp. 21635-21640, (Dec. 2010).
Huang, et al., "NLRP3 inflammasome activation promotes inflammation-induced carcinogenesis in head and neck squamous cell carcinoma," Journal of Experimental & Clinical Cancer Research, 36:116, (2017).
Iannitti, et al., "IL-1 receptor antagonist ameliorates inflammasome-dependent inflammation in murine and human cystic fiborsis," Nature Communications, 7:10791, doi:10.1038/ncomms10791, (Mar. 2016).
Inoue, et al., "The role of interferon-β in the treatment of multiple sclerosis and experimental autoimmune encephalomyelitis—in the perspective of inflammasomes," Immunology, 139, 11-18, (2013).
Jager, et al., "Key Role of NLrp3 Inflammasome Activation in Granduloma Generation of Sarcoidosis," AM J Respir Crit Care Med, 191, A5816, (2015).
Kim, et al., "Role for NLRP3 Inflammasome-mediated, IL-1β-Dependent Responses in Severe, Steroid-Resistant Asthma," American Journal of Respiratory and Critical Care Medicine, vol. 196, No. 3, pp. 283-297, (Aug. 2017).
Lazaridis, et al., "Acitvation of NLRP3 Inflammasome in Inflammatory Bowel Disease: Differences Between Crohn's Disease and Ulcerative Colitis," Dig Dis Sci, 62:2348-2356, (2017).
Li, et al., "Dysregulation of the NLRP3 inflammasome complex and related cytokines in patients with multiple myeloma," Hematology, vol. 21, No. 3, pp. 144-151, (2016).
Li, et al., "Aging-related gene signature regulated by NLrp3 predicts glioma progression," Am J Cancer Res., 5(1) 442-449, (2015).
Loukovaara, et al., "NLRP3 inflammasome activation is associated with proliferative diabetic retinopathy," Acta Ophthalmol, 95: 803-808, (2017).
Masters, "Specific inflammasomes in complex diseases," Clinical Immunology, http://dx.doi.org/10.1016/j.clim.2012.12.006, (2013).
Menu et al., "The NLRP3 inflammasome in health and disease: the good, the bad and the ugly," Clinical and Experimental Immunology, 166: 1-15. (Jun. 2011).
Mridha, et al., "NLRP3 inflammasome blockade reduces liver inflammation and fibrosis in experimenal NASH in mice," Journal of Hepatology, http://dx.doi.org/10.1016/j.jhep.2017.01.022, (2017).
Neudecker, et al., "Myeloid-derived miR-223 regulates intestinal inflammation via repression of the NLRP3 inflammasome," JEM, published online May 9, 2017 at http://doi.org/10.1084/jem.20160462, downloaded on (Jun. 2019).
Niebuhr, et al., "Impaired NLRP3 inflammasome expressison and function in atopic dermatitis due to Th2 milieu," Allergy, 69: 1058-1067, (2014).
Ozaki, et al., "Targeting the NLRP3 inflammasome in chronic inflammatory diseases: current perspectives," Journal of Inflammation Research, 8, 15-27, (Jan. 2015).
Primiano, et al., "Efficacy and Pharmacology of the NLRP3 Inflammasome Inhibitor CP-456,773 (CRID3) in Murine Models of Dermal and Plumonary Inflammation," The Journal of Immunology, 197: 2421-2433, (2016).
Puyang, et al., "Retinal Ganglion Cell Loss is Delayed Following Opti Nerve Crush in NLRP3 Knockout Mice," Scientific Reports, 6:20998, (Feb. 2016).
Qin, et al., "Propionibacterium acnes induces IL-1β secretion via the NLRP3 inflammasome in human monocytes," J Invest Dermatol, 134(2): 381-388, (Feb. 2014).
Ridker, et al., "Antiinflammatory Therapy with Canakinumab for Atherosclerotic Disease," The New England Journal of Medicine, DOI:10.1056/NEJMoa1707914, (Aug. 2017).
Ridker, et al., "Effect of interleukin-1β inhibition with canakinumab on incident lung cancer in patients with atherosclerosis: exploratory results from a randomised, double-blind, plaebo-controlled trial," Lancet, 390: 1833-42, (2017).
Sano, et al., "Tet2-Mediated Clonal Hematopoiesis Accelerates Heart Failure Through a Mechanism Involoving the IL-1β/NLRP3 Inflammasome," The Journal of the American College of Cardiology, vol. 71, No. 8, pp. 875-886, (Feb. 2018).
Schroder, et al., "The Inflammasomes," Cell, 140, 821-832, (Mar. 2010).
Scott, et al., "A randomised trial evaluating anakinra in early active rheumatoid arthritis," Clinical and Experimental Reheumatology, 34: 88-93, (2016).
Strowig, et al., "Inflammasomes in health and disease," Nature, vol. 481, pp. 278-286, (Jan. 2012).
Tarallo, et al., "DICER1 Loss and Alu RNA Induce Age-Related Macular Degeneration via the NLRP3 Inflammasome and MyD88," Cell, 149, 847-859, (May 2012).
VanHout, et al., "The selective NLRP3-inflammasome inhibitor MCC950 reduces infarct size and preserves cardiac function in a pig model of myocardial infarction," European Heart Journal, 38, 828-836, (2017).
Walsh, et al., "Inflammasomes in the CNS," Nature Reviews, vol. 15, pp. 84-97, (Feb. 2014).
Wang, et al., "Activation of NLRP3 inflammasome enhances the proliferation and migration of A549 lung cancer cells," Onccology Reports, 35: 2053-2064, (2016).
Wen, et al., "A role for the NLRP3 inflammasome in metabolic diseases—did Warburg miss inflammation?" Nature Immunology, vol. 13, No. 4, pp. 352-357, (Apr. 2012).
Wu, et al., "NLRP3 Nucleotide Oligomerization Domain-Like Receptor Family, Pyrin Domain Containing 3)-Caspase-1 Inflammasome Degrades Contractile Proteins," Arterioscler Thromb Vase Biol., 37:694-706, (Apr. 2017).
U.S. Appl. No. 16/977,249, Final Office Action dated Jan. 19, 2023.
U.S. Appl. No. 16/977,249, Non-Final Office Action dated Apr. 27, 2022.
U.S. Appl. No. 16/977,249, Requirement for Restriction/Election dated Sep. 15, 2021.

(56) References Cited

OTHER PUBLICATIONS

U.S. Appl. No. 16/977,434, Final Office Action dated Apr. 11, 2023.
U.S. Appl. No. 16/977,451, Notice of Allowance dated Sep. 21, 2021.
U.S. Appl. No. 16/977,452, Non-Final Office Action and Interview Summary dated Dec. 5, 2023.
U.S. Appl. No. 16/977,452, Requirement for Restriction/Election dated Nov. 23, 2001.
U.S. Appl. No. 16/977,464, Non-Final Office Action dated Jun. 30, 2022.
U.S. Appl. No. 16/977,464, Requirement for Restriction/Election dated Dec. 13, 2021.
U.S. Appl. No. 16/977,452, Final Office Action dated Dec. 13, 2022.
U.S. Appl. No. 16/977,452, Non-Final Office Action dated Apr. 27, 2022.
U.S. Appl. No. 16/977,451, Final Office Action dated Mar. 31, 2022.
U.S. Appl. No. 16/977,451, Non-Final Office Action dated Aug. 11, 2022.
Rautio, et al. "Prodrugs: design and clinical applications," Nature Reviews, vol. 7, pp. 255-270, (Mar. 2008).
U.S. Appl. No. 16/977,445, Final Office Action dated Feb. 15, 2023.
U.S. Appl. No. 16/977,445, Non-Final Office Action dated May 2, 2022.
U.S. Appl. No. 16/977,445, Requirement for Restriction/Election dated Jan. 20, 2022.
U.S. Appl. No. 16/977,452, Requirement for Restriction/Election dated Nov. 23, 2021.
U.S. Appl. No. 16/977,4364, Final Office Action dated Apr. 11, 2023.
U.S. Appl. No. 16/977,445, Non-Final Office Action and Interview Summary dated Aug. 10, 2023.
U.S. Appl. No. 16/977,464, Non-Final Office Action dated Aug. 22, 2023.
Blevins et al., "The NLRPS Inflammasome Pathway: A Review of Mechanisms and Inhibitors for the Treatment of Inflammatory Diseases," Frontiers in Aging Neuroscience, vol. 14, Article, 879021, (Jun. 2022).
Zhang et al., "Mechanisms of NLRP3 Inflammasome Activation: Its Role in the Treatment of Alzheimer's Disease," Neurochemical Research, 45:2560-2572, (Sep. 2020).

\* cited by examiner

COMPOUNDS

CROSS-REFERENCE TO RELATED APPLICATIONS

This application is a national stage entry of PCT/EP2019/055140 filed Mar. 1, 2019, which claims the benefit of GB Patent Application No. 1803411.6 filed Mar. 2, 2018 and GB Patent Application No. 1902318.3 filed Feb. 20, 2019.

FIELD OF THE INVENTION

The present invention relates to compounds of formula (I) and to associated salts, solvates, prodrugs and pharmaceutical compositions. The present invention further relates to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlr3–/– mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-p-nitrostyrene and dimethyl sulfoxide (DMSO), although these agents have limited potency and are nonspecific.

Current treatments for NLRP3-related diseases include biologic agents that target IL-1. These are the recombinant IL-1β receptor antagonist anakinra, the neutralizing IL-1p antibody canakinumab and the soluble decoy IL-1β receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1p is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1, WO 2018/015445 A1, WO 2018/136890 A1, WO 2018/215818 A1, WO 2019/008025 A1 and WO 2019/008029 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

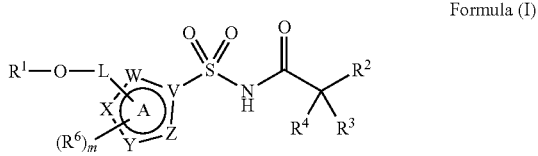

Formula (I)

wherein:
Q is selected from O or S;
V is selected from N or C, and W, X, Y and Z are each independently selected from N, O, NH or CH, wherein at least one of V, W, X, Y and Z is N or NH;
L is a saturated or unsaturated hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;
$R^1$ is hydrogen or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally L and $R^1$ together with the oxygen atom to which they are attached may form a 3- to 12-membered saturated or unsaturated cyclic group, wherein the cyclic group may optionally be substituted;
optionally $R^1$—O—L—, and any two adjacent W, X, Y or Z, may together form a 3- to 12-membered saturated or unsaturated cyclic group fused to ring A, wherein the cyclic group fused to ring A may optionally be substituted;
$R^2$ is a cyclic group substituted at the α and α' positions, wherein $R^2$ may optionally be further substituted;
$R^3$ is hydrogen, halogen, —OH, —NH$_2$, —CN, —R$^5$, —OR$^5$, —NHR$^5$ or —N(R$^5$)$_2$;
$R^4$ is hydrogen, halogen, —OH, —NH$_2$, —CN, —R$^5$, —OR$^5$, —NHR$^5$ or —N(R$^5$)$_2$; or
$R^3$ and $R^4$ together with the carbon atom to which they are attached may form a 3- to 7-membered saturated or unsaturated cyclic group, wherein the cyclic group may optionally be substituted;
each $R^5$ is independently an optionally substituted $C_1$-$C_4$ alkyl group;
each $R^6$ is independently halogen, —OH, —NO$_2$, —NH$_2$, —N$_3$, —SH, —SO$_2$H, —SO$_2$NH$_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
optionally any $R^6$, and any two adjacent W, X, Y or Z, may together form a 3- to 12-membered saturated or unsaturated cyclic group fused to ring A, wherein the cyclic group fused to ring A may optionally be substituted; and
m is 0, 1, 2 or 3;
provided that any atom of L or $R^1$ that is directly attached to W, X, Y or Z is not the same atom of L or $R^1$ that is directly attached to the oxygen atom of $R^1$—O—L—.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_2$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear (i.e. straight-chained) or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

As used herein, where it is stated that a cyclic group is monocyclic, it is to be understood that the cyclic group is not substituted with a divalent bridging substituent (e.g. —O—, —S—, —NH—, —N(R$^\beta$)— or —R$^\alpha$—) so as to form a bridged, fused or spiro substituent. However, unless stated otherwise, a substituted monocyclic group may be substituted with one or more monovalent cyclic groups. Similarly, where it is stated that a group is bicyclic, it is to be understood that the cyclic group including any bridged, fused or spiro divalent bridging substituents attached to the cyclic group, but excluding any monovalent cyclic substituents, is bicyclic.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

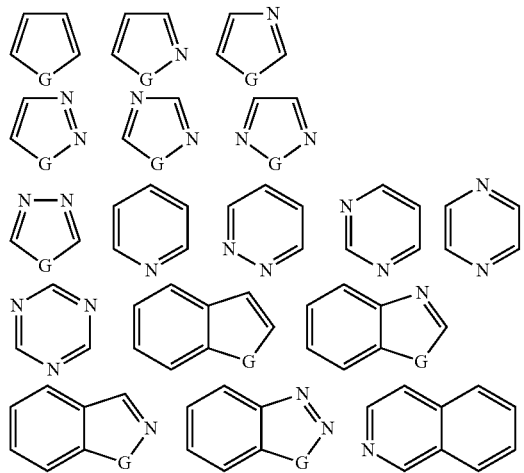

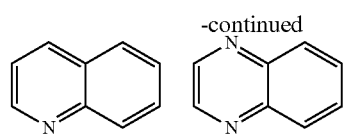

wherein G=O, S or NH.

Unless stated otherwise, where a cyclic group or moiety is stated to be non-aromatic, such as a cycloalkyl, cycloalkenyl or non-aromatic heterocyclic group, it is to be understood that the group or moiety, excluding any ring systems which are part of or formed by optional substituents, is non-aromatic. Similarly, where a cyclic group or moiety is stated to be aromatic, such as an aryl or a heteroaryl group, it is to be understood that the group or moiety, excluding any ring systems which are part of or formed by optional substituents, is aromatic. A cyclic group or moiety is considered non-aromatic, when it does not have any tautomers that are aromatic. When a cyclic group or moiety has a tautomer that is aromatic, it is considered aromatic, even if it has tautomers that are not aromatic.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^1$)$_2$; —NH—R$^\alpha$—OH; —NH—R$^\alpha$—OR; —NH—R$^\alpha$—NH$_2$; —NH—R$^\alpha$—NHR$^\beta$; —NH—R$^\alpha$—N(R)$_2$; —NR$^\beta$—R$^\alpha$—OH; —NR$^\beta$—R$^\alpha$—OR; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; a C$_3$-C$_7$ cycloalkyl group optionally substituted with one or more C$_1$-C$_3$ alkyl or C$_1$-C$_3$ haloalkyl groups; a C$_3$-C$_7$ cycloalkenyl group optionally substituted with one or more C$_1$-C$_3$ alkyl or C$_1$-C$_3$ haloalkyl groups; or a 3- to 7-membered non-aromatic heterocyclic group optionally substituted with one or more C$_1$-C$_6$ alkyl or C$_1$-C$_6$ haloalkyl groups; and/or (ii) any two hydrogen atoms attached to the same carbon or nitrogen atom may optionally be replaced by a π-bonded substituent independently selected from oxo (═O), ═S, ═NH or ═NR$^\beta$; and/or (iii) any sulfur atom may optionally be substituted with one or two π-bonded substituents independently selected from oxo (═O), ═NH or ═NR$^\beta$; and/or (iv) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a $C_1$-$C_6$ alkyl, $C_2$-$C_6$ alkenyl, $C_2$-$C_6$ alkynyl or $C_3$-$C_6$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —C≡CH, oxo (═O), or 4- to 6-membered heterocyclic group.

Typically, in an optionally substituted group or moiety:
(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR—COR$^\beta$; —CONH$_2$; —CONHR$^\beta$; —CON(R)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R)$_2$; a $C_3$-$C_7$ cycloalkyl group optionally substituted with one or more $C_1$-$C_3$ alkyl or $C_1$-$C_3$ haloalkyl groups; a $C_3$-$C_7$ cycloalkenyl group optionally substituted with one or more $C_1$-$C_3$ alkyl or $C_1$-$C_3$ haloalkyl groups; or a 3- to 7-membered non-aromatic heterocyclic group optionally substituted with one or more $C_1$-$C_6$ alkyl or $C_1$-$C_6$ haloalkyl groups; and/or (ii) any two hydrogen atoms attached to the same carbon atom may optionally be replaced by a π-bonded substituent independently selected from oxo (═O), ═S, ═NH or ═NR$^\beta$; and/or (iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a $C_1$-$C_6$ alkyl, $C_2$-$C_6$ alkenyl, $C_2$-$C_6$ alkynyl or $C_3$-$C_6$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —C≡CH, oxo (═O), or 4- to 6-membered heterocyclic group.

Typically, in an optionally substituted group or moiety:
(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR—COR$^\beta$; —CONH$_2$; —CONHR$^\beta$; —CON(R)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R)$_2$; a $C_3$-$C_7$ cycloalkyl group optionally substituted with one or more $C_1$-$C_3$ alkyl or $C_1$-$C_3$ haloalkyl groups; a $C_3$-$C_7$ cycloalkenyl group optionally substituted with one or more $C_1$-$C_3$ alkyl or $C_1$-$C_3$ haloalkyl groups;

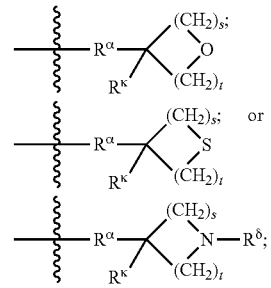

(ii) any two hydrogen atoms attached to the same carbon atom may optionally be replaced by a π-bonded substituent independently selected from oxo (═O), ═S, ═NH or ═NR$^\beta$; and/or (iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;

wherein each —R$^\alpha$— is independently selected from an alkylene, alkenylene or alkynylene group, wherein the alkylene, alkenylene or alkynylene group contains from 1 to 6 carbon atoms in its backbone, and wherein the alkylene, alkenylene or alkynylene group may optionally be substituted with one or more halo and/or —R$^\beta$ groups;

wherein each —R$^\beta$ is independently selected from a C$_1$-C$_6$ alkyl, C$_2$-C$_6$ alkenyl, C$_2$-C$_6$ alkynyl or C$_3$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), halo, —OH, —CN, —C≡CH, oxo (═O), or 4- to 6-membered heterocyclic group;

wherein each —R$^\delta$ is independently selected from hydrogen, C$_1$-C$_5$ alkyl, C$_1$-C$_5$ haloalkyl, —CO(C$_1$-C$_3$ alkyl) or C$_3$-C$_6$ cycloalkyl;

wherein each —R$^\kappa$ is independently selected from hydrogen, C$_1$-C$_3$ alkyl, C$_1$-C$_3$ haloalkyl or C$_1$-C$_3$ alkoxy;

wherein each s is independently selected from 1, 2 or 3; and wherein each t is independently selected from 1, 2 or 3.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —N(R$^\beta$)— or —R$^\alpha$—) of an optionally substituted group or moiety (e.g. R$^1$) must only be attached to the specified group or moiety and may not be attached to a second group or moiety (e.g. R$^2$), even if the second group or moiety can itself be optionally substituted.

The term "halogen" or "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

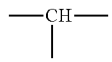

is replaced by

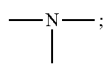

—CH$_2$— is replaced by —NH—, —O— or —S—;
—CH$_3$ is replaced by —NH$_2$, —OH or —SH;
—CH═ is replaced by —N═;
CH$_2$═ is replaced by NH═, O═ or S═; or
CH≡ is replaced by N≡;

provided that the resultant group comprises at least one carbon atom. For example, methoxy, dimethylamino and aminoethyl groups are considered to be hydrocarbyl groups including one or more heteroatoms N, O or S in their carbon skeleton.

In the context of the present specification, unless otherwise stated, a C$_x$-C$_y$ group is defined as a group containing from x to y carbon atoms. For example, a C$_1$-C$_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are to be counted as carbon atoms when calculating the number of carbon atoms in a C$_x$-C$_y$ group. For example, a morpholinyl group is to be considered a C$_6$ heterocyclic group, not a C$_4$ heterocyclic group.

For the purposes of the present specification, where it is stated that a first atom or group is "directly attached" to a second atom or group it is to be understood that the first atom or group is covalently bonded to the second atom or group with no intervening atom(s) or group(s) being present. So, for example, for the group (C═O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

As will be understood, ring A is a 5-membered heteroaryl group containing at least one nitrogen atom, optionally one or more oxygen atoms, but no sulfur atoms in the 5-membered ring structure. In one embodiment, ring A is monocyclic. In such an embodiment, the groups R$^1$—O-L- and, if present, R$^6$ are monovalent, but may be or include cyclic groups. Examples of monocyclic 5-membered heteroaryl groups containing at least one nitrogen atom, optionally one or more oxygen atoms, but no sulfur atoms in the 5-membered ring structure include pyrrolyl, imidazolyl, pyrazolyl, triazolyl, tetrazolyl, oxazolyl, isoxazolyl and oxadiazolyl groups.

For the purposes of the present specification, where it is stated that W, X, Y or Z may be NH or CH, it is to be understood that this refers to W, X, Y and Z before possible substitution with R$^1$—O-L- or R$^6$ is considered. Thus, where it is stated that W, X, Y or Z may be NH, it is to be understood that W, X, Y or Z may be NH, N—R$^6$ or N-L-O—R$^1$ after substitution is considered. Similarly, where it is stated that W, X, Y or Z may be CH, it is to be understood that W, X, Y or Z may be CH, C—$R^6$ or C-L-O—$R^1$ after substitution is considered.

As stated, V is selected from N or C, and W, X, Y and Z are each independently selected from N, O, NH or CH, wherein at least one of V, W, X, Y and Z is N or NH. Typically, one, two or three of V, W, X, Y and Z are N or NH. Typically, at least one of V, W, X, Y and Z is C or CH.

In one embodiment, V is selected from N or C, and W, X, Y and Z are each independently selected from N, NH or CH, wherein at least one of V, W, X, Y and Z is N or NH. Typically in such an embodiment, one, two or three of V, W, X, Y and Z are N or NH, and the remainder of V, W, X, Y and Z are C or CH. Examples of such groups include pyrrolyl, imidazolyl, pyrazolyl and triazolyl groups. More typically, two of V, W, X, Y and Z are N or NH, and three of V, W, X, Y and Z are C or CH. Thus, in this most typical embodiment ring A is an imidazolyl or a pyrazolyl group.

As will be understood, $R^1$—O-L- may be attached to any ring atom represented by W, X, Y or Z. Typically, $R^1$—O-L- is attached to X or Y.

In one embodiment, $R^1$—O-L- is attached to a ring nitrogen atom of ring A. In another embodiment, $R^1$—O-L- is attached to a ring carbon atom of ring A.

In one embodiment, the group $R^1$—O-L-, including any optional substituents, contains only atoms selected from the group consisting of carbon, hydrogen, nitrogen, oxygen and halogen atoms. In a further embodiment, the group $R^1$—O-L-, including any optional substituents, contains only atoms selected from the group consisting of carbon, hydrogen, oxygen and halogen atoms. In a further embodiment, the group $R^1$—O-L-, including any optional substituents, contains only atoms selected from the group consisting of carbon, hydrogen and oxygen atoms.

As stated above, L is a saturated or unsaturated hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton. Since any atom of L that is directly attached to W, X, Y or Z is not the same atom of L that is directly attached to the oxygen atom of $R^1$—O-L-, L must comprise at least two atoms.

Typically, L contains from 2 to 10 atoms other than hydrogen or halogen. More typically, L contains from 2 to 8 atoms other than hydrogen or halogen. Most typically, L contains from 2 to 4 atoms other than hydrogen or halogen.

In one embodiment, L is an alkylene or an alkenylene group, wherein the alkylene or alkenylene group may be straight-chained or branched, wherein the alkylene or alkenylene group may be optionally substituted, and wherein the alkylene or alkenylene group may optionally include one or more heteroatoms N or O in its carbon skeleton.

The alkylene or alkenylene group may be substituted with any optional substituent as outlined above, including with one or more divalent bridging substituents such that L is or includes a cyclic group. Typically however L, including any optional substituents, contains the number of atoms other than hydrogen or halogen specified above.

In one embodiment, where L is substituted, it is substituted with:
(i) one or more substituents (such as one, two or three substituents) independently selected from halo, —CN, —OH, —$NH_2$, oxo (=O) and =NH; and/or
(ii) one or more divalent bridging substituents selected from —O—, —NH—, $C_1$-$C_4$ alkylene and $C_2$-$C_4$ alkenylene groups, wherein the $C_1$-$C_4$ alkylene or $C_2$-$C_4$ alkenylene groups may be straight-chained or branched, wherein the $C_1$-$C_4$ alkylene or $C_2$-$C_4$ alkenylene groups may optionally be substituted with one or more substituents (such as one, two or three substituents) independently selected from halo, —CN, —OH, —$NH_2$, oxo (=O) and =NH, and wherein the $C_1$-$C_4$ alkylene or $C_2$-$C_4$ alkenylene groups may optionally include one or more heteroatoms N or O in their carbon skeleton.

More typically, where L is substituted, it is substituted with:
(i) one or more substituents (such as one, two or three substituents) independently selected from halo, —OH, —$NH_2$ and oxo (=O); and/or
(ii) one or more divalent bridging substituents selected from —O—, —NH—, $C_1$-$C_3$ alkylene and $C_2$-$C_3$ alkenylene groups, wherein the $C_1$-$C_3$ alkylene or $C_2$-$C_3$ alkenylene groups may be straight-chained or branched, wherein the $C_1$-$C_3$ alkylene or $C_2$-$C_3$ alkenylene groups may optionally be substituted with one or more substituents (such as one, two or three substituents) independently selected from halo, —OH, —$NH_2$ and oxo (=O), and wherein the $C_1$-$C_3$ alkylene or $C_2$-$C_3$ alkenylene groups may optionally include one or more heteroatoms N or O in their carbon skeleton.

Most typically, where L is substituted, it is substituted with:
(i) one or more substituents (such as one, two or three substituents) independently selected from fluoro, chloro, and —OH; and/or
(ii) a —$CH_2$— or —$CH_2CH_2$— group, wherein the —$CH_2$— or —$CH_2CH_2$— group may optionally be substituted with one or more substituents (such as one, two or three substituents) independently selected from fluoro, chloro, and —OH.

As stated above, $R^1$ is hydrogen or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton.

In one embodiment, $R^1$ is hydrogen or an alkyl, cycloalkyl or cycloalkyl-alkylene group, wherein the alkyl, cycloalkyl or cycloalkyl-alkylene group optionally includes one or more heteroatoms N or O in its carbon skeleton and wherein the alkyl, cycloalkyl or cycloalkyl-alkylene group is optionally substituted with one or more substituents (such as one, two or three substituents) independently selected from halo, —CN, —OH, —$NH_2$, oxo (=O) and =NH. More typically, $R^1$ is hydrogen or a $C_1$-$C_6$ alkyl or $C_3$-$C_6$ cycloalkyl group, wherein the $C_1$-$C_6$ alkyl or $C_3$-$C_6$ cycloalkyl group is optionally substituted with one or more substituents (such as one, two or three substituents) independently selected from halo, —OH, —$NH_2$ and oxo (=O). More typically still, $R^1$ is hydrogen or a $C_1$-$C_4$ alkyl group, wherein the $C_1$-$C_4$ alkyl group is optionally substituted with one or more fluoro and/or chloro groups. Most typically, $R^1$ is hydrogen or methyl.

Typically, where $R^1$ is not hydrogen, $R^1$ contains from 1 to 8 atoms other than hydrogen or halogen. More typically, where $R^1$ is not hydrogen, $R^1$ contains from 1 to 6 atoms other than hydrogen or halogen. Most typically, where $R^1$ is not hydrogen, $R^1$ contains from 1 to 4 atoms other than hydrogen or halogen.

In another embodiment, L and $R^1$ together with the oxygen atom to which they are attached may form a 3- to 12-membered saturated or unsaturated cyclic group, wherein the cyclic group may optionally be substituted. As will be appreciated, the resultant cyclic group is a heterocyclic group, typically a non-aromatic heterocyclic group. In such an embodiment, not all of L and/or $R^1$ need to form the resultant cyclic group. Accordingly, the resultant group $R^1$—O-L- may for example be an alkyl-substituted heterocyclyl group, or a heterocyclyl-alkylene group.

Typically, L and $R^1$ together with the oxygen atom to which they are attached form a 3- to 7-membered saturated or unsaturated monocyclic group, wherein the monocyclic group may optionally be substituted. Typically, said monocyclic group is a monocyclic non-aromatic heterocyclic group. More typically, said monocyclic group is a 4- to 6-membered saturated heterocyclic group which only includes the atoms O and C and optionally N in the ring structure.

In one embodiment, $R^1$—O-L- has the formula $R^{10}$-$L^2$-, wherein:

$R^{10}$ is a 3- to 12-membered saturated or unsaturated heterocyclic group, wherein $R^{10}$ includes at least one oxygen atom in the ring structure, wherein $R^{10}$ optionally includes one or more additional heteroatoms N, O or S in the ring structure, and wherein $R^{10}$ is optionally substituted; and $L^2$ is a bond or a saturated or unsaturated hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;

provided that at least one oxygen atom in the ring structure of $R^{10}$ is not directly attached to the same atom of $R^{10}$-$L^2$- that is directly attached to W, X, Y or Z.

Typically, the group $R^{10}$-$L^2$- contains from 4 to 12 atoms other than hydrogen or halogen. More typically, the group $R^{10}$-$L^2$- contains from 4 to 10 atoms other than hydrogen or halogen. Most typically, the group $R^{10}$-$L^2$- contains from 5 to 8 atoms other than hydrogen or halogen.

Typically, $R^{10}$ is a 3- to 7-membered saturated or unsaturated monocyclic group, wherein $R^{10}$ includes at least one oxygen atom in the ring structure, wherein $R^{10}$ optionally includes one or more additional heteroatoms N or O in the ring structure, and wherein $R^{10}$ is optionally substituted. Typically, $R^{10}$ is non-aromatic. More typically, $R^{10}$ is a 4- to 6-membered saturated monocyclic group, wherein $R^{10}$ includes at least one oxygen atom in the ring structure, wherein $R^{10}$ optionally includes one or two additional heteroatoms N or O in the ring structure, and wherein $R^{10}$ is optionally substituted. For example, $R^{10}$ may be an optionally substituted oxetanyl, tetrahydrofuranyl, 1,3-dioxolanyl, tetrahydropyranyl, 1,4-dioxanyl or morpholinyl group.

Typically, $L^2$ is a bond or an alkylene or an alkenylene group, wherein the alkylene or alkenylene group may be straight-chained or branched, wherein the alkylene or alkenylene group may optionally be substituted, and wherein the alkylene or alkenylene group may optionally include one or more heteroatoms N or O in its carbon skeleton. More typically, $L^2$ is a bond or an alkylene group, wherein the alkylene may be straight-chained or branched, wherein the alkylene group may optionally be substituted, wherein the alkylene group may optionally include one or two heteroatoms N or O in its carbon skeleton, and wherein $L^2$, including any optional substituents, contains from 1 to 6 atoms other than hydrogen or halogen. More typically still, $L^2$ is a bond or a —$CH_2$—, —CO— or —N(Me)-CO— group. Most typically, $L^2$ is a bond, i.e. $R^1$—O-L- has the formula $R^{10}$— wherein $R^1$ is as defined above.

Where $R^{10}$ is substituted, typically it is substituted with one or more substituents (such as one, two or three substituents) independently selected from halo, —CN, —OH, —$NH_2$, oxo (=O), =NH, —$R^{20}$, —$OR^{20}$, —$NHR^{20}$, —$N(R^{20})_2$ or =$NHR^{20}$, wherein each $R^{20}$ is independently selected from a $C_1$-$C_4$ alkyl, $C_1$-$C_4$ haloalkyl, $C_3$-$C_4$ cycloalkyl or $C_3$-$C_4$ halocycloalkyl group, or any two $R^{20}$ attached to the same nitrogen atom may together form a $C_2$-$C_5$ alkylene or $C_2$-$C_5$ haloalkylene group. More typically, where $R^{10}$ is substituted, it is substituted with one or more substituents (such as one, two or three substituents) independently selected from halo, —CN, —OH, —$NH_2$, —$R^2$, —$OR^2$, —$NHR^2$ and —$N(R^{20})_2$, wherein each $R^{20}$ is independently selected from a $C_1$-$C_4$ alkyl, $C_1$-$C_4$ haloalkyl, $C_3$-$C_4$ cycloalkyl or $C_3$-$C_4$ halocycloalkyl group, or any two $R^{20}$ attached to the same nitrogen atom may together form a $C_2$-$C_5$ alkylene or $C_2$-$C_5$ haloalkylene group. More typically still, where $R^{10}$ is substituted, it is substituted with one or more substituents (such as one, two or three substituents) independently selected from fluoro, chloro, —OH, —$NH_2$, -Me, -Et, —OMe, —OEt, —NHMe, —NHEt, —$N(Me)_2$, —N(Me)Et and —$N(Et)_2$ groups, wherein any methyl (Me) or ethyl (Et) group may optionally be substituted with one or more fluoro and/or chloro groups. Most typically, where $R^{10}$ is substituted, it is substituted with one or more substituents (such as one, two or three substituents) independently selected from fluoro, —OH, -Me, -Et, —OMe, —OEt, —$N(Me)_2$, —N(Me)Et and —$N(Et)_2$ groups, wherein any methyl (Me) or ethyl (Et) group may optionally be substituted with one or more fluoro groups.

Where $L^2$ is substituted, typically it is substituted with one or more substituents (such as one, two or three substituents) independently selected from halo, —CN, —OH, —$NH_2$, oxo (=O) and =NH. More typically, where $L^2$ is substituted, it is substituted with one or more substituents (such as one, two or three substituents) independently selected from halo, —CN, —OH, —$NH_2$ and oxo (=O). Most typically, where $L^2$ is substituted, it is substituted with one or more substituents (such as one, two or three substituents) independently selected from fluoro, chloro, —OH and oxo (=O).

In one embodiment, $R^1$—O-L- is monovalent. In one embodiment, where $R^1$—O-L- is monovalent, $R^1$—O-L- has a saturated structure, wherein the saturated structure is branched or includes a saturated cyclic group, and wherein $R^1$—O-L- contains from 4 to 6 atoms other than hydrogen or halogen.

In an alternate embodiment, $R^1$—O-L- and any two adjacent W, X, Y or Z may together form a 3- to 12-membered saturated or unsaturated cyclic group fused to ring A, wherein the cyclic group fused to ring A may optionally be substituted. Thus, it will be understood that in such an embodiment the group $R^1$—O-L- forms a divalent bridging substituent between two adjacent W, X, Y and Z. In such an embodiment, $R^1$ may be divalent, such that part or all of $R^1$ and part or all of L may together form the fused cyclic group, or L may be trivalent, such that part or all of L forms the fused cyclic group and $R^1$—O— does not form part of the fused cyclic group. Typically in such an embodiment, $R^1$—O-L- and any two adjacent W, X, Y or Z together form a 4- to 7-membered saturated or unsaturated cyclic group fused to ring A, wherein the cyclic group fused to ring A may optionally be substituted, such that the ring A and the fused cyclic group together form a fused bicyclic group.

As stated above, any atom of L or $R^1$ that is directly attached to W, X, Y or Z is not the same atom of L or $R^1$ that is directly attached to the oxygen atom of $R^1$—O-L-. Typically, the oxygen atom of $R^1$—O-L- is directly attached to L at a position β, γ, δ, or ε relative to any ring atom W, X, Y or Z to which the group $R^1$—O-L- is directly attached. For example, where L is —(CH$_2$)$_5$— attached to the ring atom X, $R^1$—O— may be directly attached at any of the β, γ, δ, or ε positions as shown, but may not be directly attached at the α position:

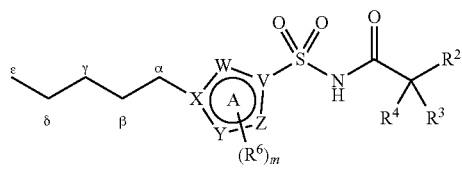

For the avoidance of doubt, heteroatoms O, N or S in the carbon skeleton of L are to be taken into consideration when allocating the nomenclature α, β, γ, etc. For example, where $R^1$—O— is MeO— and L is —(CH$_2$)$_2$—N(Me)-CO— attached to the ring atom X, $R^1$—O— is considered to be directly attached to L at the δ position as shown:

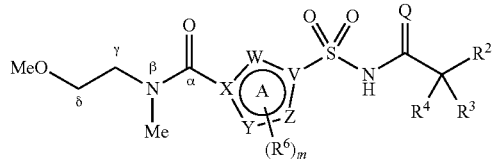

Where $R^1$—O-L- is or includes a cyclic group, it will be understood that the oxygen atom of $R^1$—O-L- may be considered to be directly attached to L at more than one β, γ, δ, or ε position. For example, in the following structure the oxygen atom may be considered to be attached at the β or the γ position:

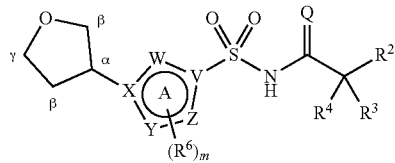

More typically, the oxygen atom of $R^1$—O-L- is directly attached to L at a position β or γ relative to any ring atom W, X, Y or Z to which the group $R^1$—O-L- is directly attached. Most typically, the oxygen atom of $R^1$—O-L- is directly attached to L at a position β relative to any ring atom W, X, Y or Z to which the group $R^1$—O-L- is directly attached.

In one aspect of any of the above embodiments, $R^1$—O-L- is substituted with a group R, wherein $R^{11}$ is directly attached to an atom of $R^1$—O-L- that is directly attached to W, X, Y or Z, and wherein R is selected from the group consisting of halo, —OH, —NH$_2$, —$R^{21}$, —$OR^{21}$, —$NHR^{21}$ and —$N(R^{21})_2$, wherein each $R^{21}$ is independently selected from a $C_1$-$C_4$ alkyl, $C_1$-$C_4$ haloalkyl, $C_3$-$C_4$ cycloalkyl or $C_3$-$C_4$ halocycloalkyl group, or any two $R^{21}$ attached to the same nitrogen atom may together form a $C_2$-$C_5$ alkylene or $C_2$-$C_5$ haloalkylene group. For example, $R^1$—O-L- may be substituted with a group $R^{11}$, wherein $R^{11}$ is attached to L at an a position relative to any ring atom W, X, Y or Z to which the group $R^1$—O-L- is directly attached. More typically, $R^{11}$ is selected from the group consisting of fluoro, chloro, —OH, —NH$_2$, —OMe, —OEt, —NHMe, —NHEt, —N(Me)$_2$, —N(Me)Et and —N(Et)$_2$ groups, wherein any methyl (Me) or ethyl (Et) group may optionally be substituted with one or more fluoro and/or chloro groups. More typically still, $R^{11}$ is selected from the group consisting of —OH, —OMe and —OEt, wherein any methyl (Me) or ethyl (Et) group may optionally be substituted with one or more fluoro groups. Most typically, $R^1$ is —OMe.

In one embodiment, where $R^1$—O-L- has the formula $R^{10}$—, $R^{11}$ is attached to the ring atom of $R^{10}$ that is directly attached to W, X, Y or Z. In such an embodiment, $R^1$—O-L- may have the formula:

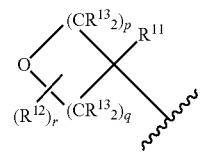

wherein:
$R^{11}$ is as previously defined;
p is 1, 2 or 3 and q is 1, 2 or 3, provided that p+q≤4;
r is 0, 1, 2, 3 or 4;
each $R^{12}$ is independently selected from —CN, —OH, —NH$_2$, —$R^{22}$, —$OR^{22}$, —$NHR^{22}$ and —$N(R^{22})_2$;
each $R^{13}$ is independently selected from hydrogen or halogen; and
each $R^{22}$ is independently selected from a $C_1$-$C_4$ alkyl, $C_1$-$C_4$ haloalkyl, $C_3$-$C_4$ cycloalkyl or $C_3$-$C_4$ halocycloalkyl group, or any two $R^{22}$ directly attached to the same nitrogen atom may together form a $C_2$-$C_5$ alkylene or $C_2$-$C_5$ haloalkylene group.

More typically, p is 1 or 2 and q is 1 or 2, r is 0, 1 or 2, each $R^{12}$ is independently selected from —OH, —NH$_2$, -Me, -Et, —OMe, —OEt, —NHMe, —NHEt, —N(Me)$_2$, —N(Me)Et and —N(Et)$_2$, wherein any methyl (Me) or ethyl (Et) group may optionally be substituted with one or more fluoro and/or chloro groups, and each $R^{13}$ is independently selected from hydrogen, fluoro or chloro groups.

Most typically, p is 1, q is 1 or 2, r is 0, and each $R^{13}$ is hydrogen.

In one embodiment, $R^1$—O-L- is selected from the group consisting of:

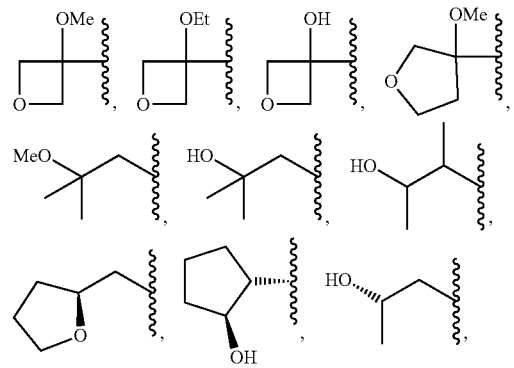

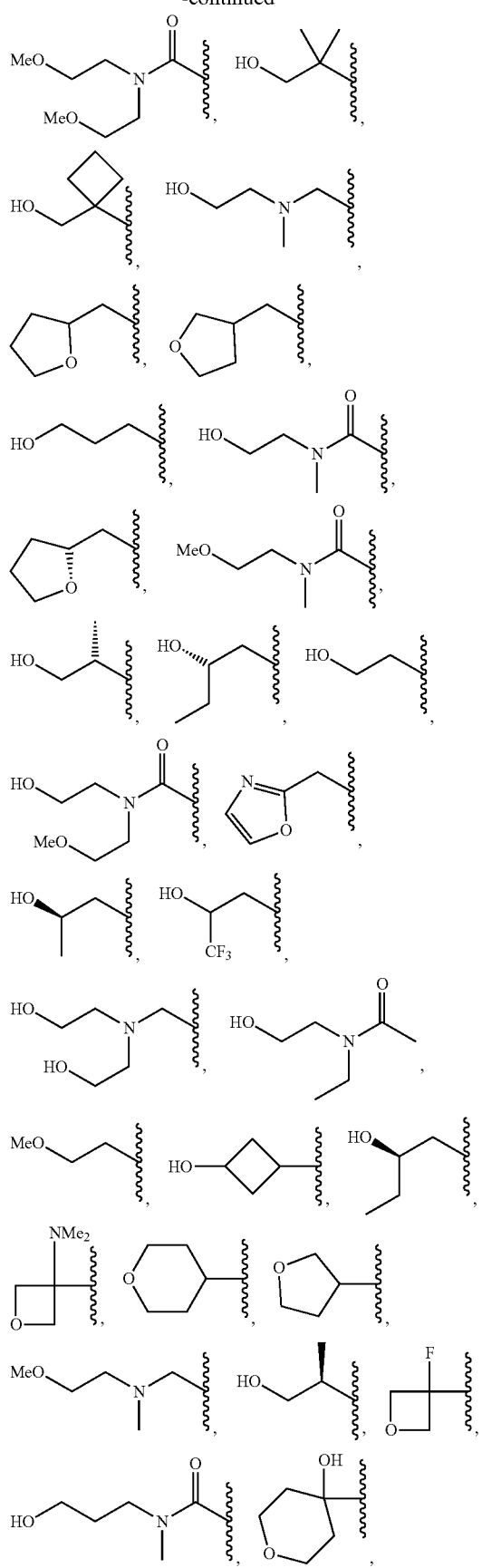

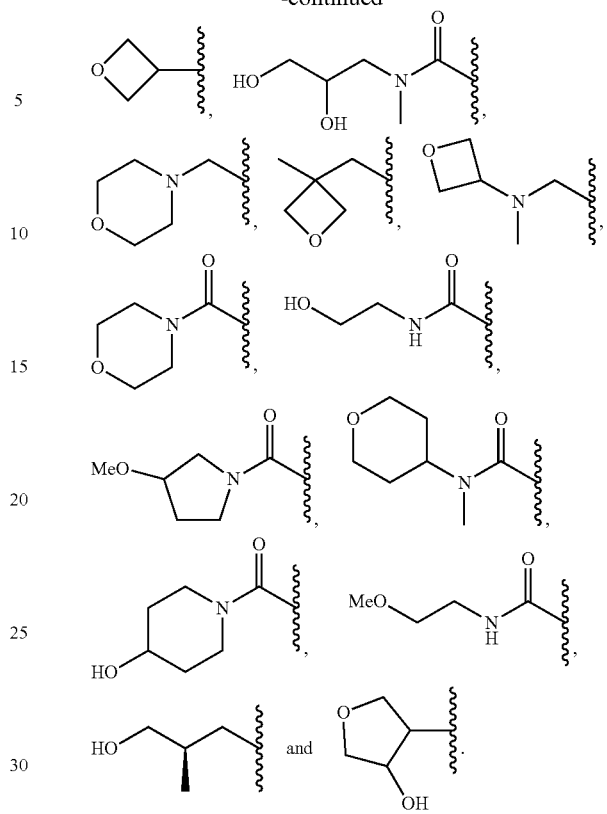

In one embodiment, the group:

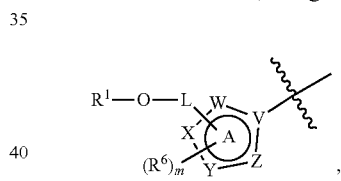

including any optional substituents, contains from 8 to 20 atoms other than hydrogen or halogen. More typically, the group contains from 8 to 16 atoms other than hydrogen or halogen.

As stated above, m is 0, 1, 2 or 3. More typically, m is 0, 1 or 2. Most typically, m is 0 or 1.

As will be understood, each $R^6$—, where present, may be directly attached to any ring atom represented by W, X, Y or Z. Typically, each $R^6$—, where present, is directly attached to X or Y. More typically, where m is 1, $R^1$—O-L- is directly attached to one of X or Y and $R^6$— is directly attached to the other of X or Y.

In any of the above embodiments, each $R^6$ may be independently selected from halo; —CN; —$NO_2$; —$N_3$; —$R^\beta$; —OH; —$OR^\beta$; —$R^\alpha$-halo; —$R^\alpha$—CN; —$R^\alpha$—$NO_2$; —$R^\alpha$—$N_3$; —$R^\alpha$—$R^\beta$; —$R^\alpha$—OH; —$R^\alpha$—$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$R^\alpha$—SH; —$R^\alpha$—$SR^\beta$; —$R^\alpha$—$SOR^\beta$; —$R^\alpha$—$SO_2H$; —$R^\alpha$—$SO_2R^\beta$; —$R^\alpha$—$SO_2NH_2$; —$R^\alpha$—$SO_2NHR^\beta$; —$R^\alpha$—$SO_2N(R^\beta)_2$; —$NH_2$; —$NHR^\beta$; —$N(R)_2$; —$R^\alpha$—$NH_2$; —$R^\alpha$—$NHR^\beta$; —$R^\alpha$—$N(R)_2$; —CHO; —CORP; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; —$R^\alpha$—$OCOR^\beta$; —NH—CHO; —$NR^\beta$—CHO; —NH—$COR^\beta$; —$NR^\beta$—$COR^\beta$; —$CONH_2$; —$CONHR^\beta$;

—CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^1$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; or —NR$^\beta$—R$^\alpha$—N(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_3$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

In one embodiment, each R$^6$ may be independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(RP)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(RP)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —CORP; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_3$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

Alternatively, each R$^6$ may be independently selected from halo; —CN; —R$^\beta$; —OH; —OR$^\beta$; —R$^\alpha$-halo; —R$^\alpha$—CN; —R$^\alpha$—R$^\beta$; —R$^\alpha$—OH; —R$^\alpha$—OR$^\beta$; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_3$-C$_6$ cyclic group, and wherein any —R$^\beta$ may optionally be substituted with one or more C$_1$-C$_4$ alkyl, halo, —OH, or 4- to 6-membered heterocyclic group.

In one embodiment, each R$^6$ is monovalent. Alternatively or in addition, any R$^6$, and any two adjacent W, X, Y or Z, may together form a 3- to 12-membered saturated or unsaturated cyclic group fused to ring A, wherein the cyclic group fused to ring A may optionally be substituted. Thus, it will be understood that in such an embodiment the group —R$^6$— forms a divalent bridging substituent between two adjacent W, X, Y and Z. In such an embodiment, part or all of R$^6$ may form the fused cyclic group. Typically in such an embodiment, —R$^6$— and any two adjacent W, X, Y or Z together form a 4- to 7-membered saturated or unsaturated cyclic group fused to ring A, wherein the cyclic group fused to ring A may optionally be substituted, such that the ring A and the fused cyclic group together form a fused bicyclic group.

More typically, each R$^6$ is independently selected from a C$_1$-C$_6$ alkyl, C$_2$-C$_6$ alkenyl, C$_2$-C$_6$ alkynyl or C$_3$-C$_6$ cyclic group, wherein any C$_1$-C$_6$ alkyl, C$_2$-C$_6$ alkenyl, C$_2$-C$_6$ alkynyl or C$_3$-C$_6$ cyclic group may optionally be substituted with one or more halo groups. More typically still, each R$^6$ is independently selected from a C$_1$-C$_4$ alkyl or C$_3$-C$_4$ cycloalkyl group, wherein any C$_1$-C$_4$ alkyl or C$_3$-C$_4$ cycloalkyl group may optionally be substituted with one or more fluoro and/or chloro groups. Most typically each R$^6$ is independently selected from a methyl, ethyl, isopropyl, cyclopropyl or t-butyl group.

In one aspect of any of the above embodiments, each R$^6$ contains from 1 to 12 atoms other than hydrogen or halogen. More typically, each R$^6$ contains from 1 to 6 atoms other than hydrogen or halogen. Most typically, each R$^6$ contains from 1 to 4 atoms other than hydrogen or halogen.

R$^2$ is a cyclic group substituted at the α and α' positions, wherein R$^2$ may optionally be further substituted. For the avoidance of doubt, it is noted that it is a ring atom of the cyclic group of R$^2$ that is directly attached to the carbon atom of the remainder of the molecule, not any substituent.

As used herein, the nomenclature α, β, α', β' refers to the position of the atoms of a cyclic group, such as —R$^2$, relative to the point of attachment of the cyclic group to the remainder of the molecule. For example, where —R$^2$ is a 1,2,3,5,6,7-hexahydro-s-indacen-4-yl moiety, the α, β, α' and β' positions are as follows:

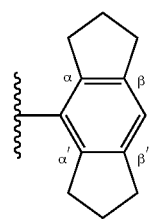

For the avoidance of doubt, where it is stated that a cyclic group, such as an aryl or a heteroaryl group, is substituted at the α and α' positions, it is to be understood that the hydrogen atoms at the α and α' positions respectively are replaced by substituents, such as any optional substituent as defined above. Unless stated otherwise, the term 'substituted' does not include the replacement of one or more ring carbon atoms by one or more ring heteroatoms.

In one embodiment, the α,α'-substituted cyclic group of $R^2$ is a 5- or 6-membered cyclic group, wherein the cyclic group may optionally be further substituted. In one embodiment, the α,α'-substituted cyclic group of $R^2$ is an aryl or a heteroaryl group, all of which may optionally be further substituted. In one embodiment, the α,α'-substituted cyclic group of $R^2$ is a phenyl or a 5- or 6-membered heteroaryl group, all of which may optionally be further substituted. In one embodiment, the α,α'-substituted cyclic group of $R^2$ is phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl or isothiazolyl, all of which may optionally be further substituted. In one embodiment, the α,α'-substituted cyclic group of $R^2$ is phenyl, pyridinyl or pyrazolyl, all of which may optionally be further substituted. In one embodiment, the α,α'-substituted cyclic group of $R^2$ is a phenyl group substituted at the 2- and 6-positions, or substituted at the 2-, 4- and 6-positions, or substituted at the 2-, 3-, 4- and 6-positions.

In another embodiment, $R^2$ is a cycloalkyl, cycloalkenyl or non-aromatic heterocyclic group substituted at the α and α' positions, wherein $R^2$ may optionally be further substituted.

In any of the above embodiments, typical substituents at the α and/or α' positions of the parent cyclic group of $R^2$ comprise a carbon atom. For example, typical substituents at the α and/or α' positions may be independently selected from —$R^7$, —$OR^7$ and —$COR^7$ groups, wherein each $R^7$ is independently selected from a $C_1$-$C_6$ alkyl, $C_2$-$C_6$ alkenyl, $C_2$-$C_6$ alkynyl or $C_3$-$C_6$ cyclic group and wherein each $R^7$ is optionally further substituted with one or more halo groups. More typically, the substituents at the α and/or α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, at least one substituent at the α and/or α' positions comprises a carbon atom. Typically, each substituent at the α and/or α' positions comprises a carbon atom. More typically, $R^2$ is substituted at the α and α' positions and both substituents at the α and α' positions comprise a carbon atom.

Other typical substituents at the α and/or α' positions of the parent cyclic group of $R^2$ may include cycloalkyl, cycloalkenyl, non-aromatic heterocyclic, aryl or heteroaryl rings which are fused to the parent cyclic group across the α,β and/or α', β' positions respectively. Such fused cyclic groups are described in greater detail below.

In one embodiment, $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the aryl or heteroaryl group across the α,β positions, and the aryl or heteroaryl group is further substituted at the α' position, for example with a substituent selected from —$R^7$, —$OR^7$ and —$COR^7$, wherein each $R^7$ is independently selected from a $C_1$-$C_6$ alkyl, $C_2$-$C_6$ alkenyl, $C_2$-$C_6$ alkynyl or $C_3$-$C_6$ cyclic group and wherein each $R^7$ is optionally further substituted with one or more halo groups, and wherein $R^2$ may optionally be further substituted. Typically in such an embodiment, $R^2$ is bicyclic or tricyclic.

More typically, $R^2$ is a fused phenyl or a fused 5- or 6-membered heteroaryl group, wherein the phenyl or the 5- or 6-membered heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the phenyl or the 5- or 6-membered heteroaryl group across the α,β positions so as to form a 4- to 6-membered fused ring structure, and the phenyl or the 5- or 6-membered heteroaryl group is further substituted at the α' position, for example with a substituent selected from —$R^7$, —$OR^7$ and —$COR^7$, wherein each $R^7$ is independently selected from a $C_1$-$C_6$ alkyl, $C_2$-$C_6$ alkenyl, $C_2$-$C_6$ alkynyl or $C_3$-$C_6$ cyclic group and wherein each $R^7$ is optionally further substituted with one or more halo groups, and wherein $R^2$ may optionally be further substituted. Typically in such an embodiment, $R^2$ is bicyclic or tricyclic.

In another embodiment, $R^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically in such an embodiment, $R^2$ is tricyclic.

In yet another embodiment, $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α', β' positions, wherein $R^2$ may optionally be further substituted. Typically in such an embodiment, $R^2$ is tricyclic.

More typically, $R^2$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the phenyl or the 5- or 6-membered heteroaryl group across the α', β' positions so as to form a second 4- to 6-membered fused ring structure, wherein $R^2$ may optionally be further substituted. Typically in such an embodiment, $R^2$ is tricyclic.

In one embodiment. —$R^2$ has a formula selected from:

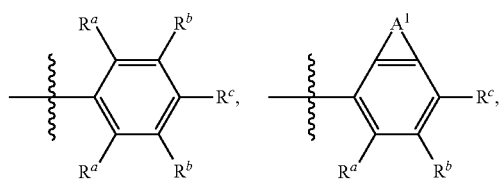

-continued

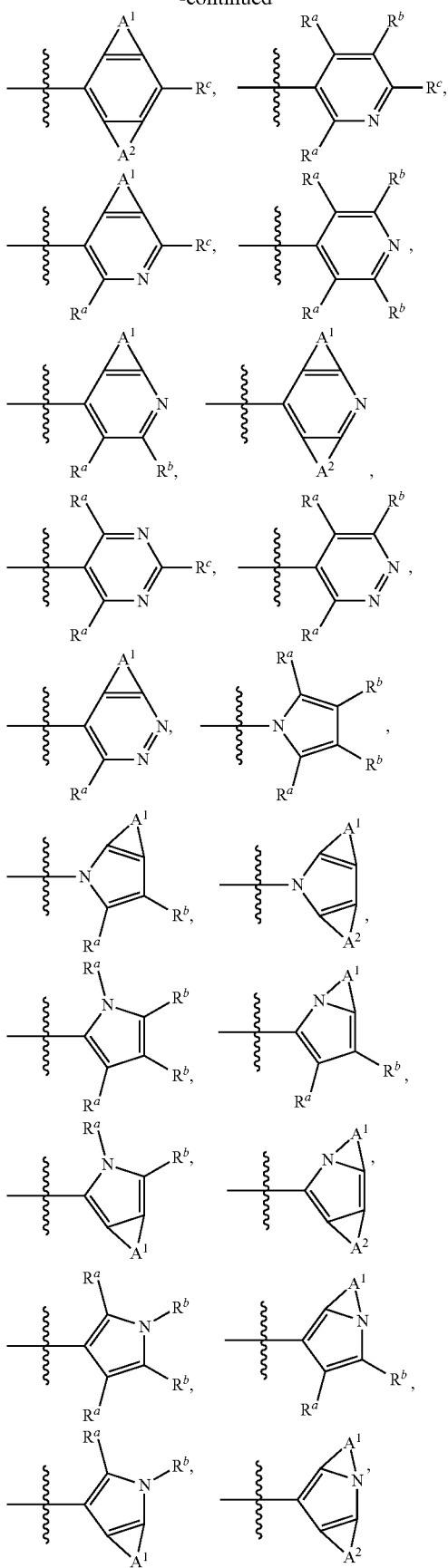
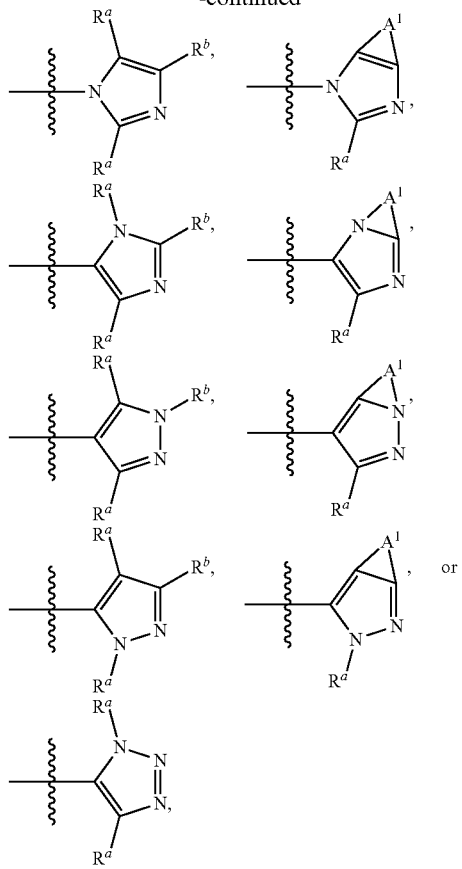

wherein:
A¹ and A² are each independently selected from an optionally substituted alkylene or alkenylene group, wherein one or more carbon atoms in the backbone of the alkylene or alkenylene group may optionally be replaced by one or more heteroatoms N, O or S;

each $R^a$ is independently selected from —$R^{aa}$, —$OR^{aa}$ or —$COR^{aa}$;

each $R^b$ is independently selected from hydrogen, halo, —$NO_2$, —CN, —$R^{aa}$, —$OR^{aa}$ or —$COR^{aa}$;

provided that any $R^a$ or $R^b$ that is directly attached to a ring nitrogen atom is not halo, —$NO_2$, —CN, or —$OR^{aa}$;

each $R^c$ is independently selected from hydrogen, halo, —OH, —$NO_2$, —CN, —$R^e$, —$OR^c$, —$COR^c$, —CO-$OR^c$, —$CONH_2$, —$CONHR^{cc}$ or —$CON(R^{cc})_2$;

each $R^{aa}$ is independently selected from a $C_1$-$C_6$ alkyl, $C_2$-$C_6$ alkenyl, $C_2$-$C_6$ alkynyl or a 3- to 7-membered cyclic group, wherein each $R^{aa}$ is optionally substituted; and each $R^{cc}$ is independently selected from a $C_1$-$C_6$ alkyl, $C_2$-$C_6$ alkenyl, $C_2$-$C_6$ alkynyl or a 3- to 7-membered cyclic group, or any two $R^c$ attached to the same nitrogen atom may, together with the nitrogen atom to which they are attached, form a 3- to 7-membered heterocyclic group, wherein each $R^c$ is optionally substituted.

Typically, any ring containing A¹ or A² is a 5- or 6-membered ring. Typically, A¹ and A² are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, $A^1$ and $A^2$ are each independently selected from an optionally substituted straight-chained alkylene group, wherein one carbon atom in the backbone of the alkylene group may optionally be replaced by an oxygen atom. Typically, no heteroatom in $A^1$ or $A^2$ is directly attached to another ring heteroatom. Typically, $A^1$ and $A^2$ are unsubstituted or substituted with one or more substituents independently selected from halo, —OH, —CN, —NO$_2$, $C_1$-$C_4$ alkyl, $C_1$-$C_4$ haloalkyl, —O($C_1$-$C_4$ alkyl) or —O($C_1$-$C_4$ haloalkyl). More typically, $A^1$ and $A^2$ are unsubstituted or substituted with one or more fluoro and/or chloro groups. Where $R^2$ contains both A and $A^2$ groups, $A^1$ and $A^2$ may be the same or different. Typically, $A^1$ and $A^2$ are the same.

Where $R^{aa}$ is a substituted $C_1$-$C_6$ alkyl, $C_2$-$C_6$ alkenyl or $C_2$-$C_6$ alkynyl group, typically the $C_1$-$C_6$ alkyl, $C_2$-$C_6$ alkenyl or $C_2$-$C_6$ alkynyl group is substituted with one or more (e.g. one or two) substituents independently selected from halo, —OH, —CN, —NO$_2$, —O($C_1$-$C_4$ alkyl) or —O($C_1$-$C_4$ haloalkyl).

Where $R^{aa}$ is a substituted 3- to 7-membered cyclic group, typically the 3- to 7-membered cyclic group is substituted with one or more (e.g. one or two) substituents independently selected from halo, —OH, —NH$_2$, —CN, —NO$_2$, —B$^1$, —OB$^1$, —NHB$^1$, —N(B)$_2$, —CONH$_2$, —CONHB$^1$, —CON(B$^1$)$_2$, —NHCOB$^1$, —NB$^1$COB$^1$, or —B$^{11}$—;
wherein each B$^1$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B$^1$ together with the nitrogen atom to which they are attached may form a 4- to 6-membered heterocyclic group containing one or two ring heteroatoms N and/or O, wherein any B$^1$ may optionally be halo-substituted and/or substituted with one or two substituents independently selected from —OH, —NH$_2$, —OB$^{12}$, —NHB$^{12}$ or —N(B$^{12}$)$_2$;
wherein each B$^{11}$ is independently selected from a $C_1$-$C_8$ alkylene or $C_2$-$C_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{12}$, —NHB$^{12}$ or —N(B$^{12}$)$_2$; and
wherein each B$^{12}$ is independently selected from a $C_1$-$C_3$ alkyl or $C_1$-$C_3$ haloalkyl group. Typically, any divalent group —B$^{11}$— forms a 4- to 6-membered fused ring.

Typically, each $R^a$ is —$R^{aa}$. More typically, each $R^a$ is independently selected from a $C_1$-$C_6$ alkyl (in particular $C_3$-$C_6$ branched alkyl) or $C_3$-$C_6$ cycloalkyl group, wherein each $R^a$ is optionally further substituted with one or more halo groups. More typically, each $R^a$ is independently selected from a $C_1$-$C_4$ alkyl, $C_1$-$C_4$ haloalkyl, $C_3$-$C_4$ cycloalkyl or $C_3$-$C_4$ halocycloalkyl group. Where a group $R^a$ is present at both the α- and α'-positions, each $R^a$ may be the same or different. Typically, each $R^a$ is the same.

Typically, each $R^b$ is independently selected from hydrogen or halo. More typically, each $R^b$ is hydrogen.

Typically, each $R^c$ is independently selected from hydrogen, halo, —OH, —NO$_2$, —CN, —R— or —OR$^{cc}$. More typically, each $R^c$ is independently selected from hydrogen, halo, —CN, $C_1$-$C_3$ alkyl, $C_1$-$C_3$ haloalkyl, cyclopropyl or halocyclopropyl. Most typically, each R is independently selected from hydrogen or halo.

Typically, each $R^c$ is independently selected from a $C_1$-$C_4$ alkyl or $C_3$-$C_6$ cycloalkyl group, or any two $R^{cc}$ attached to the same nitrogen atom may, together with the nitrogen atom to which they are attached, form a 3- to 6-membered saturated heterocyclic group, wherein each $R^{cc}$ is optionally substituted. Where R is substituted, typically $R^{cc}$ is substituted with one or more halo, —OH, —CN, —NO$_2$, —O($C_1$-$C_4$ alkyl) or —O($C_1$-$C_4$ haloalkyl) groups. More typically, each $R^{cc}$ is independently selected from a $C_1$-$C_4$ alkyl, $C_1$-$C_4$ haloalkyl, $C_3$-$C_4$ cycloalkyl or $C_3$-$C_4$ halocycloalkyl group.

In one embodiment, —$R^2$ has a formula selected from:

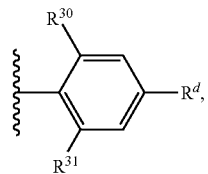

wherein $R^{30}$ and $R^{31}$ are independently selected from $C_1$-$C_4$ alkyl, $C_1$-$C_4$ haloalkyl, $C_3$-$C_4$ cycloalkyl and $C_3$-$C_4$ halocycloalkyl, and $R^d$ is hydrogen, halo, —OH, —NO$_2$, —CN, —$R^{dd}$, —OR$^{dd}$, —COR$^{dd}$, —COOR$^{dd}$, —CONH$_2$, —CONHR$^d$d or —CON($R^{dd}$)$_2$, wherein each —$R^d$d is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^{30}$ and $R^{31}$ are independently selected from $C_1$-$C_4$ alkyl, and $R^d$ is hydrogen, halo, —CN, $C_1$-$C_3$ alkyl, $C_1$-$C_3$ haloalkyl, cyclopropyl or halocyclopropyl. More typically, $R^{30}$ and $R^{31}$ are independently selected from $C_1$-$C_4$ alkyl, and $R^d$ is hydrogen or halo.

In one embodiment, —$R^2$ has a formula selected from:

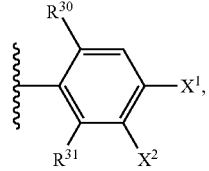

wherein $R^{30}$ and $R^{31}$ are independently selected from $C_1$-$C_4$ alkyl or $C_3$-$C_6$ cycloalkyl, and $X^1$ and $X^2$ are independently selected from hydrogen, halo or —CN.

Typically, —$R^2$ has a formula selected from:

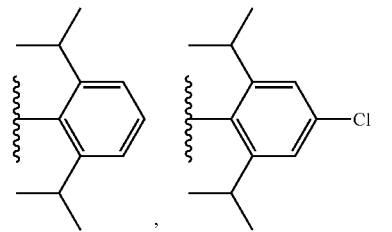

,                or

-continued

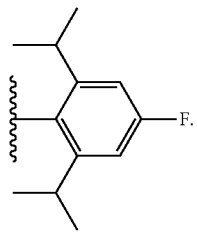

In one embodiment, —$R^2$ has a formula selected from:

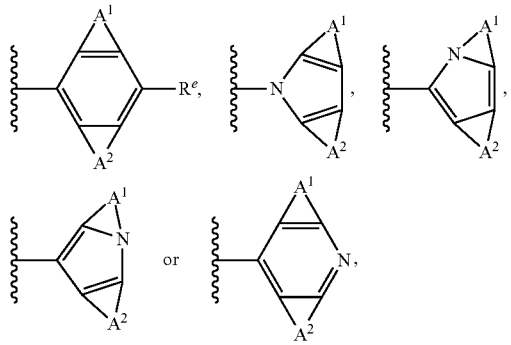

wherein $A^1$ and $A^2$ are each independently selected from an optionally substituted alkylene or alkenylene group, wherein one or more carbon atoms in the backbone of the alkylene or alkenylene group may optionally be replaced by one or more heteroatoms N, O or S, and wherein $R^e$ is hydrogen or any optional substituent. $R^e$ and any optional substituent attached to $A^1$ or $A^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to $A^1$ and any optional substituent attached to $A^2$ may also together with the atoms to which they are attached form a further fused cycloalkyl, cycloalkenyl, non-aromatic heterocyclic, aryl or heteroaryl ring which may itself be optionally substituted.

In one embodiment, $R^e$ is hydrogen, halo, —OH, —$NO_2$, —CN, —$R^{ee}$, —$OR^{ee}$, —$COR^{ee}$, —$COOR^{ee}$, —$CONH_2$, —$CONHR^{ee}$ or —$CON(R^{ee})_2$, wherein each —$R^{ee}$ is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^e$ is hydrogen or a halo, hydroxyl, —CN, —$NO_2$, —$R^{ee}$ or —$OR^{ee}$ group, wherein $R^{ee}$ is a $C_1$-$C_4$ alkyl group which may optionally be halo-substituted. More typically, $R^e$ is hydrogen or halo.

Typically, any ring containing $A^1$ or $A^2$ is a 5- or 6-membered ring.

Typically, $A^1$ and $A^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, $A^1$ and $A^2$ are each independently selected from an optionally substituted straight-chained alkylene group, wherein one carbon atom in the backbone of the alkylene group may optionally be replaced by an oxygen atom. Typically, no heteroatom in $A^1$ or $A^2$ is directly attached to another ring heteroatom. Typically, $A^1$ and $A^2$ are unsubstituted or substituted with one or more halo, hydroxyl, —CN, —$NO_2$, —$B^3$ or —$OB^3$ groups, wherein $B^3$ is a $C_1$-$C_4$ alkyl group which may optionally be halo-substituted. More typically, $A^1$ and $A^2$ are unsubstituted or substituted with one or more fluoro and/or chloro groups. Where $R^2$ contains both $A^1$ and $A^2$ groups, $A^1$ and $A^2$ may be the same or different. Typically, $A^1$ and $A^2$ are the same.

In a further embodiment —$R^2$ has a formula selected from:

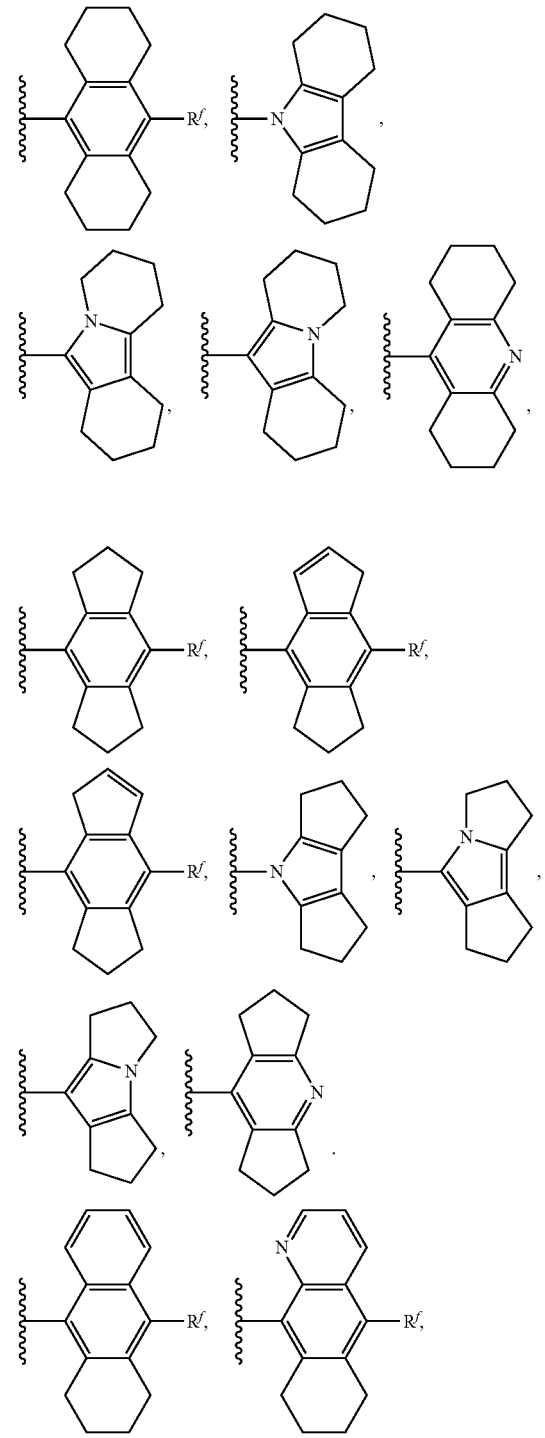

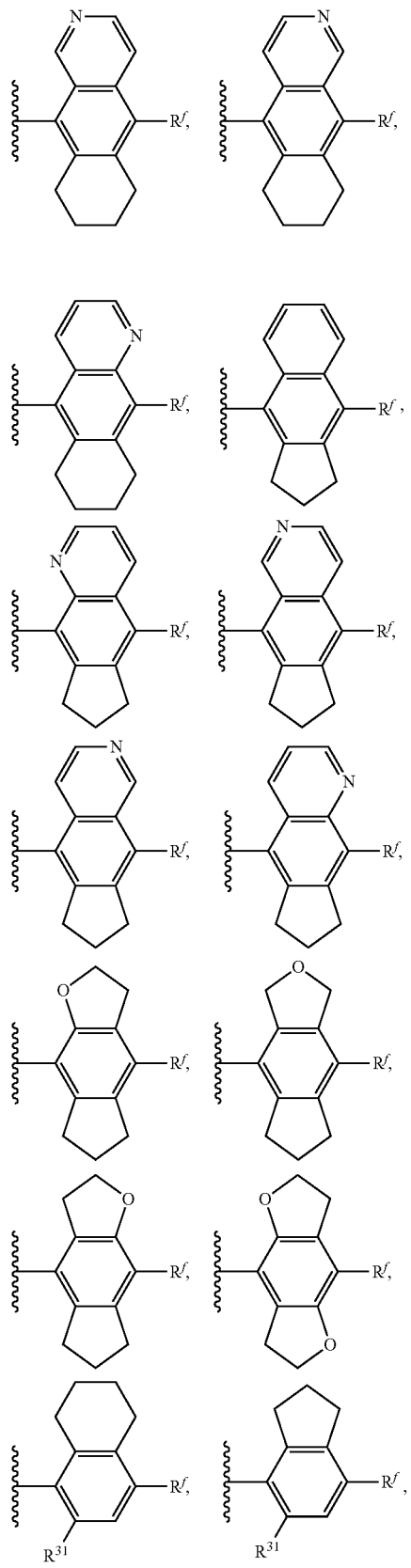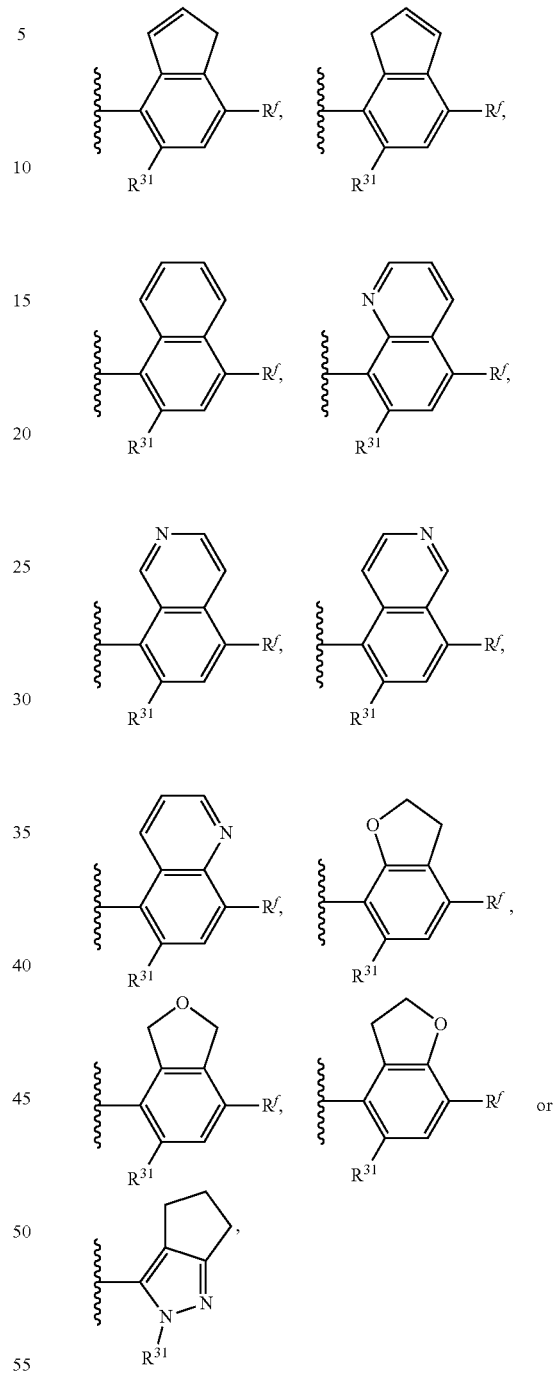

wherein $R^{31}$ is $C_1$-$C_4$ alkyl, $C_1$-$C_4$ haloalkyl, $C_3$-$C_4$ cycloalkyl or $C_3$-$C_4$ halocycloalkyl, and $R^f$ is hydrogen, halo, —OH, —$NO_2$, —CN, —$R^f f$, —$OR^f f$, —$COR^f f$, —$COOR^f f$, —$CONH_2$, —$CONHR^{ff}$ or —$CON(R^{ff})_2$, wherein each —$R^f f$ is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^{31}$ is $C_1$-$C_4$ alkyl, and $R^f$ is hydrogen, halo, —CN, $C_1$-$C_3$ alkyl, $C_1$-$C_3$ haloalkyl, cyclopropyl or halocyclopropyl. Typically, $R^{31}$ is $C_1$-$C_4$ alkyl, and $R^f$ is hydrogen or halo.

Typically, —R² has a formula selected from:

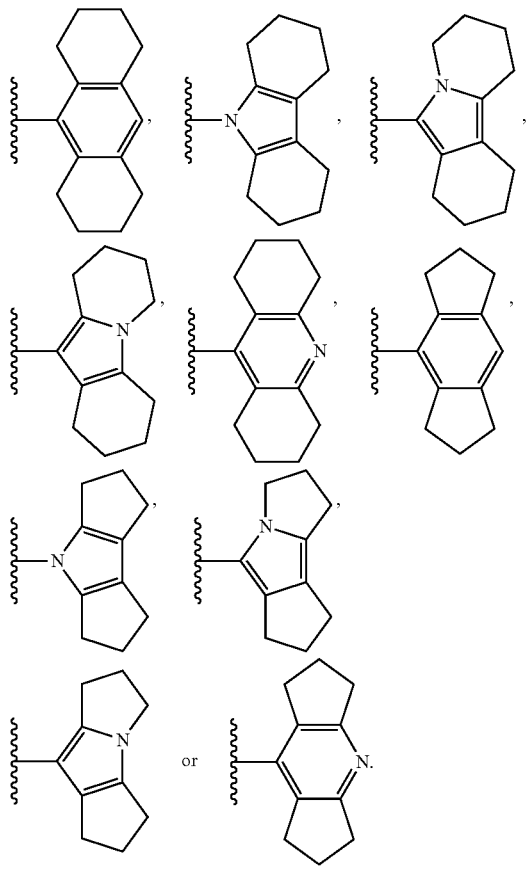

More typically, —R² has the formula:

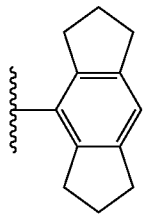

Yet other typical substituents at the α-position of the parent cyclic group of R² may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group is substituted at the α'-position and may optionally be further substituted. Such R² groups are described in greater detail below.

In one embodiment, the α,α'-substituted parent cyclic group of R² is a 5- or 6-membered cyclic group, wherein the cyclic group may optionally be further substituted. In one embodiment, the α,α'-substituted parent cyclic group of R² is an aryl or a heteroaryl group, all of which may optionally be further substituted. In one embodiment, the α,α'-substituted parent cyclic group of R² is a phenyl or a 5- or 6-membered heteroaryl group, all of which may optionally be further substituted. In one embodiment, the α,α'-substituted parent cyclic group of R² is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α,α'-substituted parent cyclic group of R² is a phenyl, pyridinyl or pyrrolyl group, all of which may optionally be further substituted. In one embodiment, the α,α'-substituted parent cyclic group of R² is a phenyl or pyrazolyl group, both of which may optionally be further substituted. In a further embodiment, the α,α'-substituted parent cyclic group of R² is a phenyl group, which may optionally be further substituted. For example, the α,α'-substituted parent cyclic group of R² may be a phenyl group substituted at the 2- and 6-positions, or substituted at the 2-, 4- and 6-positions, or substituted at the 2-, 3-, 4- and 6-positions.

In one embodiment, R² is a parent cyclic group substituted at the α-position with a monovalent heterocyclic group or a monovalent aromatic group, wherein the heterocyclic or aromatic group may optionally be substituted, and wherein the parent cyclic group is substituted at the α'-position and may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, piperidinyl or tetrahydropyranyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl, triazolyl or tetrahydropyranyl group, all of which may optionally be substituted.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH₂, —CN, —NO₂, —B⁴, —OB⁴, —NHB⁴, —N(B⁴)₂, —CONH₂, —CONHB⁴, —CON(B⁴)₂, —NHCOB⁴, —NB⁴COB⁴, or —B⁴⁴—;

wherein each B⁴ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B⁴ together with the nitrogen atom to which they are attached may form a 4- to 6-membered heterocyclic group containing one or two ring heteroatoms N and/or O, wherein any B⁴ may optionally be halo-substituted and/or substituted with one or two substituents independently selected from —OH, —NH₂, —OB⁴⁵, —NHB⁴⁵ or —N(B⁴⁵)₂;

wherein each B⁴⁴ is independently selected from a $C_1$-$C_8$ alkylene or $C_2$-$C_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{45}$, —NHB$^{45}$ or —N(B$^{45}$)$_2$; and wherein each B$^{45}$ is independently selected from a C$_1$-C$_3$ alkyl or C$_1$-C$_3$ haloalkyl group.

Typically, any divalent group —B$^{44}$— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, C$_1$-C$_3$ alkyl, C$_2$-C$_3$ alkenyl, C$_2$-C$_3$ alkynyl, C$_1$-C$_3$ haloalkyl, —O(C$_1$-C$_3$ alkyl), —NH(C$_1$-C$_3$ alkyl) or —N(C$_1$-C$_3$ alkyl)$_2$. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, C$_1$-C$_3$ alkyl, C$_2$-C$_3$ alkenyl, C$_2$-C$_3$ alkynyl, C$_1$-C$_3$ haloalkyl, —O(C$_1$-C$_3$ alkyl), —NH(C$_1$-C$_3$ alkyl) or —N(C$_1$-C$_3$ alkyl)$_2$. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, C$_1$-C$_3$ alkyl, C$_2$-C$_3$ alkenyl, C$_2$-C$_3$ alkynyl, C$_1$-C$_3$ haloalkyl, —O(C$_1$-C$_3$ alkyl), —NH(C$_1$-C$_3$ alkyl) or —N(C$_1$-C$_3$ alkyl)$_2$.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group is substituted at the α'-position and may optionally be further substituted. The substituent at the α' position and any optional further substituents on the α-substituted parent cyclic group of R$^2$ may be independently selected from halo, —CN, —R$^e$, —OR$^e$ or —COR$^e$ groups, wherein each R$^e$ is independently selected from a C$_1$-C$_6$ alkyl, C$_2$-C$_6$ alkenyl, C$_2$-C$_6$ alkynyl or C$_3$-C$_6$ cyclic group and wherein each R$^e$ is optionally further substituted with one or more halo groups. Typically, the substituent at the α' position and any optional further substituents on the α-substituted parent cyclic group of R$^2$ are independently selected from halo, —CN, C$_1$-C$_6$ alkyl (in particular C$_3$-C$_6$ branched alkyl) or C$_3$-C$_6$ cycloalkyl groups, e.g. fluoro, chloro, —CN, isopropyl, cyclopropyl, cyclohexyl or t-butyl groups, wherein the alkyl and cycloalkyl groups are optionally further substituted with one or more fluoro and/or chloro groups.

In one embodiment, —R$^2$ has a formula selected from:

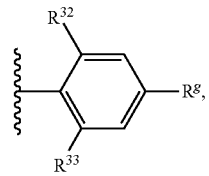

wherein R$^{32}$ is C$_1$-C$_4$ alkyl, C$_1$-C$_4$ haloalkyl, C$_3$-C$_6$ cycloalkyl or C$_3$-C$_6$ halocycloalkyl, R$^{33}$ is a 5- or 6-membered, optionally substituted heterocyclic or aromatic group, and R$^g$ is hydrogen, halo, —OH, —NO$_2$, —CN, —R$^{gg}$, —OR$^{gg}$, —COR$^{gg}$, —COOR$^{gg}$, —CONH$_2$, —CONHR$^{gg}$ or —CON(R$^{gg}$)$_2$, wherein each —R$^{gg}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group of R$^{33}$ are independently selected from halo, —OH, —NH$_2$, —CN, —NO$_2$, —B$^5$, —B$^5$, —NHB$^5$, —N(B$^5$)$_2$, —CONH$_2$, —CONHB$^5$, —CON(B$^5$)$_2$, —NHCOB$^5$, —NB$^5$COB$^5$, or —B$^{55}$—;

wherein each B$^5$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^5$ together with the nitrogen atom to which they are attached may form a 4- to 6-membered heterocyclic group containing one or two ring heteroatoms N and/or O, wherein any B$^5$ may optionally be halo-substituted and/or substituted with one or two substituents independently selected from —OH, —NH$_2$, —OB$^{56}$, —NHB$^{56}$ or —N(B$^{56}$)$_2$;

wherein each B$^{55}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{56}$, —NHB$^{56}$ or —N(B$^{56}$)$_2$; and wherein each B$^{56}$ is independently selected from a C$_1$-C$_3$ alkyl or C$_1$-C$_3$ haloalkyl group.

Typically, any divalent group —B$^{55}$— forms a 4- to 6-membered fused ring. Typically, R$^{32}$ is C$_1$-C$_4$ alkyl, R$^{33}$ is a 5- or 6-membered, optionally substituted heterocyclic or aromatic group, and R$^g$ is hydrogen, halo, —CN, C$_1$-C$_3$ alkyl, C$_1$-C$_3$ haloalkyl, cyclopropyl or halocyclopropyl. More typically, R$^{32}$ is C$_1$-C$_4$ alkyl, R$^{33}$ is a 5- or 6-membered, optionally substituted heterocyclic or aromatic group, and R$^g$ is hydrogen or halo. In one embodiment, the optional substituents on the heterocyclic or aromatic group of R$^{33}$ are independently selected from halo, —OH, —NH$_2$, —CN, —NO$_2$, —B$^5$, —OB$^5$, —NHB$^5$ or —N(B$^5$)$_2$, wherein each B$^5$ is independently selected from a C$_1$-C$_4$ alkyl, C$_2$-C$_4$ alkenyl or $C_2$-$C_4$ alkynyl group all of which may optionally be halo-substituted. In one embodiment, the optional substituents on the heterocyclic or aromatic group of $R^{33}$ are independently selected from halo, —OH, —NH$_2$, —CN, $C_1$-$C_3$ alkyl, $C_2$-$C_3$ alkenyl, $C_2$-$C_3$ alkynyl, $C_1$-$C_3$ haloalkyl, —O($C_1$-$C_3$ alkyl), —NH($C_1$-$C_3$ alkyl) or —N($C_1$-$C_3$ alkyl)$_2$.

In one embodiment, —$R^2$ has a formula selected from:

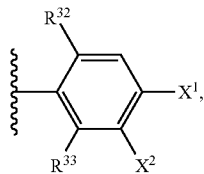

wherein $R^{32}$ is $C_1$-$C_4$ alkyl or $C_3$-$C_6$ cycloalkyl, $R^{33}$ is a 5- or 6-membered, optionally substituted heterocyclic or aromatic group, $X^1$ is hydrogen, halo or —CN, and $X^2$ is hydrogen, halo or —CN. In one embodiment, the optional substituents on the heterocyclic or aromatic group of $R^{33}$ are selected from halo, —OH, —NH$_2$, —CN, $C_1$-$C_3$ alkyl, $C_2$-$C_3$ alkenyl, $C_2$-$C_3$ alkynyl, $C_1$-$C_3$ haloalkyl, —O($C_1$-$C_3$ alkyl), —NH($C_1$-$C_3$ alkyl) or —N($C_1$-$C_3$ alkyl)$_2$.

Typically, —$R^2$ has a formula selected from:

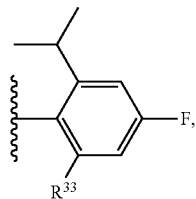

wherein $R^{33}$ is a 5- or 6-membered, optionally substituted heterocyclic or aromatic group. In one embodiment, the optional substituents on the heterocyclic or aromatic group of $R^{33}$ are independently selected from halo, —OH, —NH$_2$, —CN, —NO$_2$, —B$^6$, —OB$^6$, —NHB$^6$, —N(B$^6$)$_2$, —CONH$_2$, —CONHB$^6$, —CON(B$^6$)$_2$, —NHCOB$^6$, —NB$^6$COB$^6$, or —B$^{66}$—;
  wherein each B$^6$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B$^6$ together with the nitrogen atom to which they are attached may form a 4- to 6-membered heterocyclic group containing one or two ring heteroatoms N and/or O, wherein any B$^6$ may optionally be halo-substituted and/or substituted with one or two substituents independently selected from —OH, —NH$_2$, —OB$^{67}$, —NHB$^{67}$ or —N(B$^{67}$)$_2$;
  wherein each B$^{66}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{67}$, —NHB$^{67}$ or —N(B$^{67}$)$_2$; and
  wherein each B$^{67}$ is independently selected from a $C_1$-$C_3$ alkyl or $C_1$-$C_3$ haloalkyl group.

Typically, any divalent group —B$^{66}$— forms a 4- to 6-membered fused ring. In one embodiment, the optional substituents on the heterocyclic or aromatic group of $R^{33}$ are independently selected from halo, —OH, —NH$_2$, —CN, —NO$_2$, —B$^6$, —OB$^6$, —NHB$^6$ or —N(B$^6$)$_2$, wherein each B$^6$ is independently selected from a $C_1$-$C_4$ alkyl, $C_2$-$C_4$ alkenyl or $C_2$-$C_4$ alkynyl group all of which may optionally be halo-substituted. In one embodiment, the optional substituents on the heterocyclic or aromatic group of $R^{33}$ are independently selected from halo, —OH, —NH$_2$, —CN, $C_1$-$C_3$ alkyl, $C_2$-$C_3$ alkenyl, $C_2$-$C_3$ alkynyl, $C_1$-$C_3$ haloalkyl, —O($C_1$-$C_3$ alkyl), —NH($C_1$-$C_3$ alkyl) or —N($C_1$-$C_3$ alkyl)$_2$.

In one embodiment, $R^{33}$ is a pyridin-4-yl group optionally substituted with one or two substituents independently selected from halo, —OH, —NH$_2$, —CN, $C_1$-$C_3$ alkyl, $C_2$-$C_3$ alkenyl, $C_2$-$C_3$ alkynyl, $C_1$-$C_3$ haloalkyl, —O($C_1$-$C_3$ alkyl), —NH($C_1$-$C_3$ alkyl) or —N($C_1$-$C_3$ alkyl)$_2$. In one embodiment, $R^{33}$ is a pyridin-4-yl group optionally substituted with one or two substituents independently selected from halo, —CN, $C_1$-$C_3$ alkyl, $C_1$-$C_3$ haloalkyl, or —O($C_1$-$C_3$ alkyl). In one embodiment, $R^{33}$ is a pyridin-4-yl group substituted with one —O($C_1$-$C_3$ alkyl) group, such as —OMe.

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group is substituted at the α'-position and may optionally be further substituted. The substituent at the α' position and any optional further substituents on the parent cyclic group of $R^2$ may also include cycloalkyl, cycloalkenyl, non-aromatic heterocyclic, aryl or heteroaryl rings which are fused to the parent cyclic group of $R^2$. Typically, the cycloalkyl, cycloalkenyl, non-aromatic heterocyclic, aryl or heteroaryl rings are ortho-fused to the parent cyclic group of $R^2$, i.e. each fused cycloalkyl, cycloalkenyl, non-aromatic heterocyclic, aryl or heteroaryl ring has only two atoms and one bond in common with the parent cyclic group of $R^2$. Typically, the cycloalkyl, cycloalkenyl, non-aromatic heterocyclic, aryl or heteroaryl rings are ortho-fused to the parent cyclic group of $R^2$ across the α',β' positions.

In one embodiment, —$R^2$ has a formula selected from:

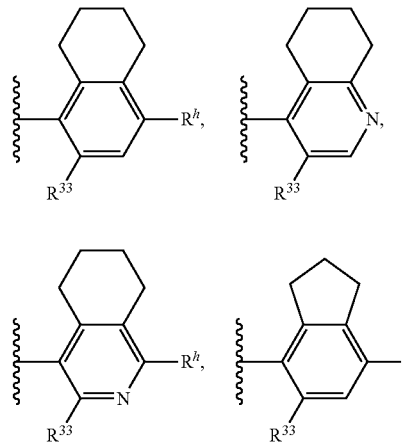

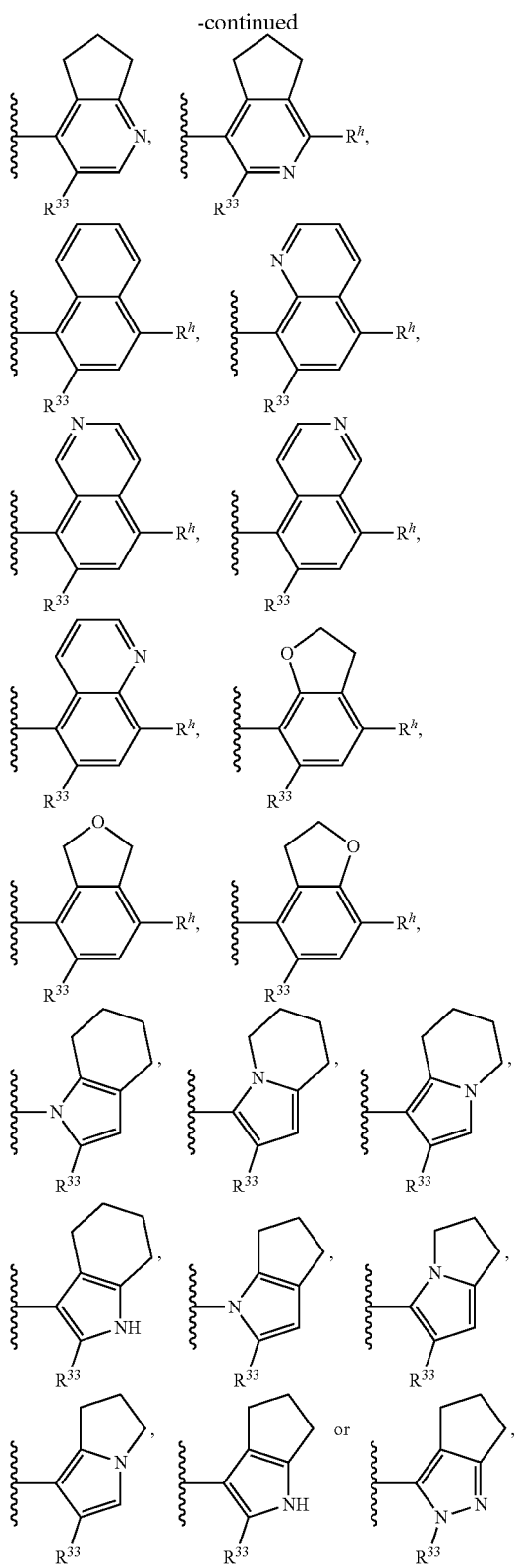

wherein $R^{33}$ is a 5- or 6-membered, optionally substituted heterocyclic or aromatic group, and $R^h$ is hydrogen, halo, —OH, —NO$_2$, —CN, —R$^{hh}$, —OR$^{hh}$, —COR$^{hh}$, —CO-OR$^{hh}$, —CONH$_2$, —CONHR$^{hh}$ or —CON(R$^{hh}$)$_2$, wherein each —R$^{hh}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group of $R^{33}$ are independently selected from halo, —OH, —NH$_2$, —CN, —NO$_2$, —B$^7$, —OB$^7$, —NHB$^7$, —N(B$^7$)$_2$, —CONH$_2$, —CONHB$^7$, —CON (B$^7$)$_2$, —NHCOB$^7$, —NB$^7$COB$^7$, or —B$^{77}$—;

wherein each B$^7$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^7$ together with the nitrogen atom to which they are attached may form a 4- to 6-membered heterocyclic group containing one or two ring heteroatoms N and/or O, wherein any B$^7$ may optionally be halo-substituted and/or substituted with one or two substituents independently selected from —OH, —NH$_2$, —OB$^{78}$, —NHB$^{78}$ or —N(B$^{78}$)

wherein each B$^{77}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{78}$, —NHB$^{78}$ or —N(B$^{78}$)$_2$; and wherein each B$^{78}$ is independently selected from a C$_1$-C$_3$ alkyl or C$_1$-C$_3$ haloalkyl group.

Typically, any divalent group —B$^{77}$— forms a 4- to 6-membered fused ring. Typically, $R^h$ is hydrogen, halo, —CN, C$_1$-C$_3$ alkyl, C$_1$-C$_3$ haloalkyl, cyclopropyl or halocyclopropyl. More typically, $R^h$ is hydrogen or halo. In one embodiment, the optional substituents on the heterocyclic or aromatic group of $R^{33}$ are independently selected from halo, —OH, —NH$_2$, —CN, —NO$_2$, —B$^7$, —OB$^7$, —NHB$^7$ or —N(B$^7$)$_2$, wherein each B$^7$ is independently selected from a C$_1$-C$_4$ alkyl, C$_2$-C$_4$ alkenyl or C$_2$-C$_4$ alkynyl group all of which may optionally be halo-substituted. In one embodiment, the optional substituents on the heterocyclic or aromatic group of $R^{33}$ are independently selected from halo, —OH, —NH$_2$, —CN, C$_1$-C$_3$ alkyl, C$_2$-C$_3$ alkenyl, C$_2$-C$_3$ alkynyl, C$_1$-C$_3$ haloalkyl, —O(C$_1$-C$_3$ alkyl), —NH(C$_1$-C$_3$ alkyl) or —N(C$_1$-C$_3$ alkyl)$_2$.

In one embodiment, —R$^2$ has a formula selected from:

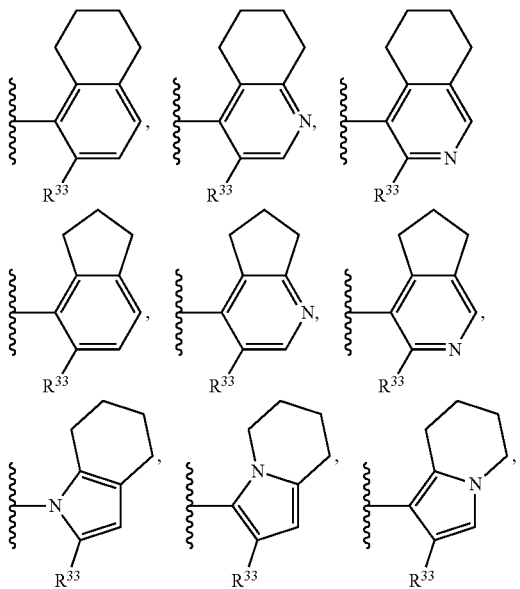

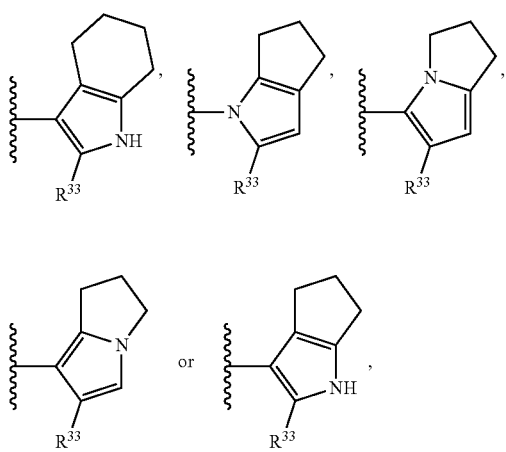

wherein $R^{33}$ is a 5- or 6-membered, optionally substituted heterocyclic or aromatic group. In one embodiment, the optional substituents on the heterocyclic or aromatic group of $R^{33}$ are independently selected from halo, —OH, —NH$_2$, —CN, —NO$_2$, —B$^8$, —OB$^8$, —NHB$^8$, —N(B$^8$)$_2$, —CONH$_2$, —CONHB$^8$, —CON(B$^8$)$_2$, —NHCOB$^8$, —NB$^8$COB$^8$, or —B$^{88}$—;

wherein each $B^8$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^8$ together with the nitrogen atom to which they are attached may form a 4- to 6-membered heterocyclic group containing one or two ring heteroatoms N and/or O, wherein any $B^8$ may optionally be halo-substituted and/or substituted with one or two substituents independently selected from —OH, —NH$_2$, —OB$^{89}$, —NHB$^{89}$ or —N(B$^{89}$)$_2$;

wherein each $B^{88}$ is independently selected from a $C_1$-$C_8$ alkylene or $C_2$-$C_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{89}$, —NHB$^{89}$ or —N(B$^{89}$)$_2$; and wherein each $B^{89}$ is independently selected from a $C_1$-$C_3$ alkyl or $C_1$-$C_3$ haloalkyl group.

Typically, any divalent group —B$^{88}$— forms a 4- to 6-membered fused ring. In one embodiment, the optional substituents on the heterocyclic or aromatic group of $R^{33}$ are independently selected from halo, —OH, —NH$_2$, —CN, —NO$_2$, —B$^8$, —OB$^8$, —NHB$^8$ or —N(B$^8$)$_2$, wherein each $B^8$ is independently selected from a $C_1$-$C_4$ alkyl, $C_2$-$C_4$ alkenyl or $C_2$-$C_4$ alkynyl group all of which may optionally be halo-substituted. In one embodiment, the optional substituents on the heterocyclic or aromatic group of $R^{33}$ are independently selected from halo, —OH, —NH$_2$, —CN, $C_1$-$C_3$ alkyl, $C_2$-$C_3$ alkenyl, $C_2$-$C_3$ alkynyl, $C_1$-$C_3$ haloalkyl, —O($C_1$-$C_3$ alkyl), —NH($C_1$-$C_3$ alkyl) or —N($C_1$-$C_3$ alkyl)$_2$.

Typically, —R$^2$ has a formula selected from:

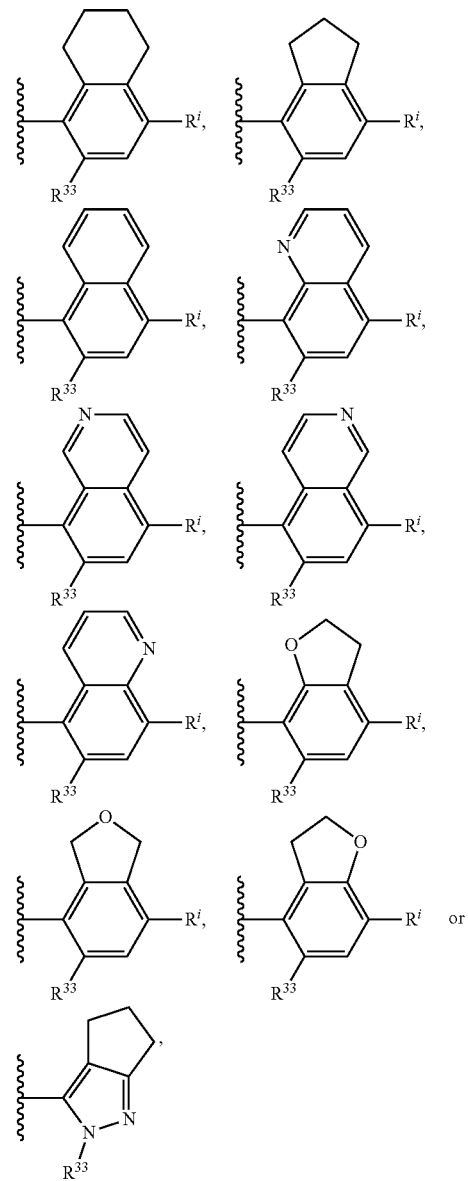

wherein $R^{33}$ is a 5- or 6-membered, optionally substituted heterocyclic or aromatic group, and $R^i$ is hydrogen, halo, —OH, —NO$_2$, —CN, —R$^{ii}$, —COR$^{ii}$, —COOR$^{ii}$, —CONH$_2$, —CONHR$^{ii}$ or —CON(R$^{ii}$)$_2$, wherein each —R$^{ii}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group of $R^{33}$ are independently selected from halo, —OH, —NH$_2$, —CN, —NO$_2$, —B$^9$, —B$^9$, —NHB$^9$, —N(B$^9$)$_2$, —CONH$_2$, —CONHB$^9$, —CON(B$^9$)$_2$, —NHCOB$^9$, —NB$^9$COB$^9$, or —B$^{99}$—;

wherein each $B^9$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^9$ together with the nitrogen atom to which they are attached may form a 4- to 6-membered heterocyclic group containing one or two ring heteroatoms N and/or O, wherein any $B^9$ may optionally be halo-substituted and/or substituted with one or two substituents independently selected from —OH, —NH$_2$, —OB$^{98}$, —NHB$^{98}$ or —N(B$^{98}$) wherein each B$^{99}$ is independently selected from a C$_1$-C$_5$ alkylene or C$_2$-C$_5$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{98}$, —NHB$^{98}$ or —N(B$^{98}$)$_2$; and wherein each B$^{98}$ is independently selected from a C$_1$-C$_3$ alkyl or C$_1$-C$_3$ haloalkyl group.

Typically, any divalent group —B$^{99}$— forms a 4- to 6-membered fused ring. Typically, R$^i$ is hydrogen, halo, —CN, C$_1$-C$_3$ alkyl, C$_1$-C$_3$ haloalkyl, cyclopropyl or halocyclopropyl. More typically, R$^i$ is hydrogen or halo. In one embodiment, the optional substituents on the heterocyclic or aromatic group of R$^{33}$ are independently selected from halo, —OH, —NH$_2$, —CN, —NO$_2$, —B$^9$, —OB$^9$, —NHB$^9$ or —N(B$^9$)$_2$, wherein each B$^9$ is independently selected from a C$_1$-C$_4$ alkyl, C$_2$-C$_4$ alkenyl or C$_2$-C$_4$ alkynyl group all of which may optionally be halo-substituted. In one embodiment, the optional substituents on the heterocyclic or aromatic group of R$^{33}$ are independently selected from halo, —OH, —NH$_2$, —CN, C$_1$-C$_3$ alkyl, C$_2$-C$_3$ alkenyl, C$_2$-C$_3$ alkynyl, C$_1$-C$_3$ haloalkyl, —O(C$_1$-C$_3$ alkyl), —NH(C$_1$-C$_3$ alkyl) or —N(C$_1$-C$_3$ alkyl)$_2$.

In one embodiment, R$^2$ is a phenyl or a 5- or 6-membered heteroaryl group (such as phenyl, pyridinyl, pyridazinyl, pyrimidinyl, pyrazinyl, pyrrolyl, pyrazolyl or imidazolyl); wherein (i) the phenyl or 5- or 6-membered heteroaryl group is substituted at the α position with a substituent selected from —R$^7$, —OR$^7$ and —COR$^7$, wherein R$^7$ is selected from a C$_1$-C$_6$ alkyl, C$_2$-C$_6$ alkenyl, C$_2$-C$_6$ alkynyl or C$_3$-C$_6$ cyclic group and wherein R$^7$ is optionally substituted with one or more halo groups; and the phenyl or 5- or 6-membered heteroaryl group is further substituted at the α' position with a substituent selected from —R$^{17}$, —OR$^{17}$ and —COR$^7$, wherein R$^{17}$ is selected from a C$_1$-C$_6$ alkyl, C$_2$-C$_6$ alkenyl, C$_2$-C$_6$ alkynyl or C$_3$-C$_6$ cyclic group and wherein R$^{17}$ is optionally substituted with one or more halo groups; and optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is further substituted at the α' position with a substituent selected from —R$^7$, —OR$^7$ and —COR$^7$, wherein R$^7$ is selected from a C$_1$-C$_6$ alkyl, C$_2$-C$_6$ alkenyl, C$_2$-C$_6$ alkynyl or C$_3$-C$_6$ cyclic group and wherein R$^7$ is optionally substituted with one or more halo groups; and optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{18}$—OR$^{19}$, —R$^{18}$—N(R$^{19}$)$_2$, —R$^{18}$—CN or —R$^{18}$—C≡CR$^{19}$, and wherein a ring atom of the monovalent heterocyclic or aromatic group is directly attached to the α-ring atom of the parent phenyl or 5- or 6-membered heteroaryl group; wherein R$^{18}$ is independently selected from a bond or a C$_1$-C$_3$ alkylene group; and R$^{19}$ is independently selected from hydrogen or a C$_1$-C$_3$ alkyl or C$_1$-C$_3$ haloalkyl group; and the phenyl or 5- or 6-membered heteroaryl group is further substituted at the α' position with a substituent selected from —R$^7$, —OR$^7$ and —COR$^7$, wherein R$^7$ is selected from a C$_1$-C$_6$ alkyl, C$_2$-C$_6$ alkenyl, C$_2$-C$_6$ alkynyl or C$_3$-C$_6$ cyclic group and wherein R$^7$ is optionally substituted with one or more halo groups; and optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{18}$—OR$^{19}$, —R$^{18}$—N(R$^{19}$)$_2$, —R$^{18}$—CN or —R$^{18}$—C≡CR$^{19}$, and wherein a ring atom of the monovalent heterocyclic or aromatic group is directly attached to the α-ring atom of the parent phenyl or 5- or 6-membered heteroaryl group; wherein R$^{18}$ is independently selected from a bond or a $C_1$-$C_3$ alkylene group; and $R^{19}$ is independently selected from hydrogen or a $C_1$-$C_3$ alkyl or $C_1$-$C_3$ haloalkyl group; and the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group).

In the embodiment directly above, where a group or moiety is optionally substituted with one or more halo groups, it may be substituted for example with one, two, three, four, five or six halo groups.

In one aspect of any of the above embodiments, $R^2$ contains from 10 to 50 atoms other than hydrogen. More typically, $R^2$ contains from 10 to 40 atoms other than hydrogen. More typically, $R^2$ contains from 10 to 35 atoms other than hydrogen. Most typically, $R^2$ contains from 12 to 30 atoms other than hydrogen.

$R^3$ is hydrogen, halogen, —OH, —$NH_2$, —CN, —$R^5$, —$OR^5$, —$NHR^5$ or —$N(R^5)_2$; wherein $R^5$ is independently optionally substituted $C_1$-$C_4$ alkyl. In one embodiment, $R^3$ is hydrogen, halogen, —OH, —$R^5$ or —$OR^5$; wherein $R^5$ is independently optionally substituted $C_1$-$C_4$ alkyl. In another embodiment, $R^3$ is hydrogen, —F, —$CH_3$, —$CH_2F$, —$CHF_2$, —$CF_3$ or cyclopropyl. In another embodiment, $R^3$ is hydrogen or —$CH_3$. In yet another embodiment, $R^3$ is hydrogen.

$R^4$ is hydrogen, halogen, —OH, —$NH_2$, —CN, —$R^5$, —$OR^5$, —$NHR^5$ or —$N(R^5)_2$; wherein $R^5$ is independently optionally substituted $C_1$-$C_4$ alkyl. In one embodiment, $R^4$ is hydrogen, halogen, —OH, —$R^5$ or —$OR^5$; wherein $R^5$ is independently optionally substituted $C_1$-$C_4$ alkyl. In another embodiment, $R^4$ is hydrogen, —F, —$CH_3$, —$CH_2F$, —$CHF_2$, —$CF_3$ or cyclopropyl. In another embodiment, $R^4$ is hydrogen or —$CH_3$. In yet another embodiment, $R^4$ is hydrogen.

Alternatively, $R^3$ and $R^4$ together with the carbon atom to which they are attached may form a 3- to 7-membered saturated or unsaturated cyclic group, wherein the cyclic group may optionally be substituted. In one embodiment, $R^3$ and $R^4$ together with the carbon atom to which they are attached may form a 3- to 6-membered saturated or unsaturated cyclic group, wherein the cyclic group may optionally be substituted. Optional substituents on such a 3- to 7-membered or 3- to 6-membered cyclic group include halogen, —OH, —$NH_2$, —CN, $C_1$-$C_4$ alkyl and $C_1$-$C_4$ alkoxy. In one embodiment, $R^3$ and $R^4$ together with the carbon atom to which they are attached form a $C_3$-$C_6$ cycloalkyl group, such as a cyclopropyl group.

$R^5$ is independently optionally substituted $C_1$-$C_4$ alkyl. Optional substituents on $R^5$ include halogen, —OH, —$NH_2$, —CN and $C_1$-$C_4$ alkoxy.

Q is selected from O or S. In one embodiment, Q is O.

In a first specific embodiment, the invention provides a compound of formula (I):

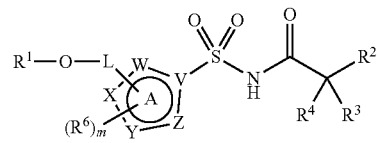

Formula (I)

wherein:
Q is O;
V is selected from N or C, and W, X, Y and Z are each independently selected from N, O, NH or CH, wherein at least one of V, W, X, Y and Z is N or NH;
ring A is a pyrrolyl, imidazolyl, pyrazolyl, triazolyl, tetrazolyl, oxazolyl, isoxazolyl or oxadiazolyl group;
L is a $C_1$-$C_8$ alkylene or a $C_1$-$C_8$ alkenylene group, wherein the alkylene or alkenylene group may be straight-chained or branched, or be or include cyclic groups, wherein the alkylene or alkenylene group may optionally include one or two heteroatoms N or O in its carbon skeleton, and wherein the alkylene or alkenylene group may be optionally be substituted with one, two or three substituents independently selected from halo, —CN, —OH, —$NH_2$, oxo (═O), ═NH, $C_1$-$C_4$ alkyl, —O($C_1$-$C_4$ alkyl), —NH($C_1$-$C_4$ alkyl), —N($C_1$-$C_4$ alkyl)$_2$ or ═NH($C_1$-$C_4$ alkyl);
$R^1$ is hydrogen or a $C_1$-$C_6$ alkyl or $C_3$-$C_6$ cycloalkyl group, wherein the alkyl or cycloalkyl group is optionally substituted with one, two or three substituents independently selected from halo, —CN, —OH, —$NH_2$, oxo (═O), ═NH, $C_1$-$C_4$ alkyl, —O($C_1$-$C_4$ alkyl), —NH($C_1$-$C_4$ alkyl), —N($C_1$-$C_4$ alkyl)$_2$ or ═NH ($C_1$-$C_4$ alkyl);
each $R^6$ is independently selected from a $C_1$-$C_6$ alkyl, $C_2$-$C_6$ alkenyl, $C_2$-$C_6$ alkynyl or $C_3$-$C_6$ cyclic group, wherein the alkyl, alkenyl, alkynyl or cyclic group may optionally be substituted with one, two, three, four or five halo groups;
m is 0, 1 or 2;
$R^2$ is an aryl or a heteroaryl group, wherein the aryl or the heteroaryl group is substituted at the α and α' positions, and wherein $R^2$ may optionally be further substituted;
$R^3$ is hydrogen, halogen, —OH, —$NH_2$, —CN, —$R^5$, —$OR^5$, —$NHR^5$ or —$N(R^5)_2$;
$R^4$ is hydrogen, halogen, —OH, —$NH_2$, —CN, —$R^5$, —$OR^5$, —$NHR^5$ or —$N(R^5)_2$; or
$R^3$ and $R^4$ together with the carbon atom to which they are attached may form a 3- to 7-membered saturated or unsaturated cyclic group optionally substituted with halogen or —OH;
$R^5$ is independently $C_1$-$C_4$ alkyl optionally substituted with halogen or —OH;
provided that any atom of L or $R^1$ that is directly attached to W, X, Y or Z is not the same atom of L or $R^1$ that is directly attached to the oxygen atom of $R^1$—O-L-.

In a second specific embodiment, the invention provides a compound of formula (II):

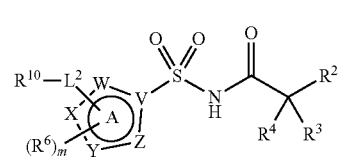

Formula (II)

wherein:

Q is O;

V is selected from N or C, and W, X, Y and Z are each independently selected from N, O, NH or CH, wherein at least one of V, W, X, Y and Z is N or NH;

ring A is a pyrrolyl, imidazolyl, pyrazolyl, triazolyl, tetrazolyl, oxazolyl, isoxazolyl or oxadiazolyl group;

$L^2$ is a bond or a $C_1$-$C_6$ alkylene group, wherein the alkylene may be straight-chained or branched, wherein the alkylene group may optionally include one or two heteroatoms N or O in its carbon skeleton, and wherein the alkylene group may optionally be substituted with one, two or three substituents independently selected from halo, —CN, —OH, —$NH_2$, oxo (=O), =NH, $C_1$-$C_4$ alkyl, —O($C_1$-$C_4$ alkyl), —NH($C_1$-$C_4$ alkyl), —N($C_1$-$C_4$ alkyl)$_2$ or =NH($C_1$-$C_4$ alkyl);

$R^{10}$ is a 4- to 6-membered saturated monocyclic group, wherein $R^{10}$ includes at least one oxygen atom in the ring structure, wherein $R^{10}$ optionally includes one or two additional heteroatoms N or O in the ring structure, and wherein $R^{10}$ may optionally be substituted with one, two or three substituents independently selected from halo, —CN, —OH, —$NH_2$, oxo (=O), =NH, $C_1$-$C_4$ alkyl, —O($C_1$-$C_4$ alkyl), —NH($C_1$-$C_4$ alkyl), —N($C_1$-$C_4$ alkyl)$_2$ or =NH($C_1$-$C_4$ alkyl);

each $R^6$ is independently selected from a $C_1$-$C_6$ alkyl, $C_2$-$C_6$ alkenyl, $C_2$-$C_6$ alkynyl or $C_3$-$C_6$ cyclic group, wherein the alkyl, alkenyl, alkynyl or cyclic group may optionally be substituted with one, two, three, four or five halo groups;

m is 0, 1 or 2;

$R^2$ is an aryl or a heteroaryl group, wherein the aryl or the heteroaryl group is substituted at the α and α' positions, and wherein $R^2$ may optionally be further substituted;

$R^3$ is hydrogen, halogen, —OH, —$NH_2$, —CN, —$R^5$, —$OR^5$, —$NHR^5$ or —N($R^5$)$_2$;

$R^4$ is hydrogen, halogen, —OH, —$NH_2$, —CN, —$R^5$, —$OR^5$, —$NHR^5$ or —N($R^5$)$_2$; or $R^3$ and $R^4$ together with the carbon atom to which they are attached may form a 3- to 7-membered saturated or unsaturated cyclic group optionally substituted with halogen or —OH;

$R^5$ is independently $C_1$-$C_4$ alkyl optionally substituted with halogen or —OH;

provided that at least one oxygen atom in the ring structure of $R^{10}$ is not directly attached to the same atom of $R^{10}$-$L^2$- that is directly attached to W, X, Y or Z.

In a third specific embodiment, the invention provides a compound of formula (II):

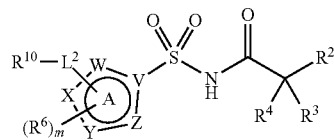

Formula (II)

wherein:

Q is O;

V is selected from N or C, and W, X, Y and Z are each independently selected from N, O, NH or CH, wherein at least one of V, W, X, Y and Z is N or NH;

ring A is a pyrrolyl, imidazolyl, pyrazolyl, triazolyl, tetrazolyl, oxazolyl, isoxazolyl or oxadiazolyl group;

$L^2$ is a bond or a $C_1$-$C_6$ alkylene group, wherein the alkylene may be straight-chained or branched, wherein the alkylene group may optionally include one or two heteroatoms N or O in its carbon skeleton, and wherein the alkylene group may optionally be substituted with one, two or three substituents independently selected from halo, —CN, —OH, —$NH_2$, oxo (=O), =NH, $C_1$-$C_4$ alkyl, —O($C_1$-$C_4$ alkyl), —NH($C_1$-$C_4$ alkyl), —N($C_1$-$C_4$ alkyl)$_2$ or =NH($C_1$-$C_4$ alkyl);

$R^{10}$ is a 4- to 6-membered saturated monocyclic group, wherein $R^{10}$ includes at least one oxygen atom in the ring structure, wherein $R^{10}$ optionally includes one or two additional heteroatoms N or O in the ring structure, and wherein $R^{10}$ may optionally be substituted with one, two or three substituents independently selected from halo, —CN, —OH, —$NH_2$, oxo (=O), =NH, $C_1$-$C_4$ alkyl, —O($C_1$-$C_4$ alkyl), —NH($C_1$-$C_4$ alkyl), —N($C_1$-$C_4$ alkyl)$_2$ or =NH($C_1$-$C_4$ alkyl);

each $R^6$ is independently selected from a $C_1$-$C_6$ alkyl, $C_2$-$C_6$ alkenyl, $C_2$-$C_6$ alkynyl or $C_3$-$C_6$ cyclic group, wherein the alkyl, alkenyl, alkynyl or cyclic group may optionally be substituted with one, two, three, four or five halo groups;

m is 0, 1 or 2;

$R^2$ is an aryl or a heteroaryl group, wherein the aryl or the heteroaryl group is substituted at the α and α' positions, and wherein $R^2$ may optionally be further substituted;

$R^3$ is hydrogen, halogen, —OH, —$R^5$ or —$OR^5$;

$R^4$ is hydrogen, halogen, —OH, —$R^5$ or —$OR^5$; or $R^3$ and $R^4$ together with the carbon atom to which they are attached may form a $C_3$-$C_6$ cycloalkyl group optionally substituted with halogen or —OH;

$R^5$ is independently $C_1$-$C_4$ alkyl optionally substituted with halogen or —OH;

provided that at least one oxygen atom in the ring structure of $R^{10}$ is not directly attached to the same atom of $R^{10}$-$L^2$- that is directly attached to W, X, Y or Z.

In a fourth specific embodiment, the invention provides a compound of formula (II):

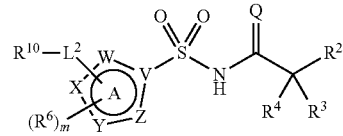

Formula (II)

wherein:

Q is O;

V is selected from N or C, and W, X, Y and Z are each independently selected from N, O, NH or CH, wherein at least one of V, W, X, Y and Z is N or NH;

ring A is a pyrrolyl, imidazolyl, pyrazolyl, triazolyl, tetrazolyl, oxazolyl, isoxazolyl or oxadiazolyl group;

$L^2$ is a bond or a $C_1$-$C_6$ alkylene group, wherein the alkylene may be straight-chained or branched, wherein the alkylene group may optionally include one or two heteroatoms N or O in its carbon skeleton, and wherein the alkylene group may optionally be substituted with one, two or three substituents independently selected from halo, —CN, —OH, —$NH_2$, oxo (=O), =NH, $C_1$-$C_4$ alkyl, —O($C_1$-$C_4$ alkyl), —NH($C_1$-$C_4$ alkyl), —N($C_1$-$C_4$ alkyl)$_2$ or =NH($C_1$-$C_4$ alkyl);

$R^{10}$ is a 4- to 6-membered saturated monocyclic group, wherein $R^{10}$ includes at least one oxygen atom in the ring structure, wherein $R^{10}$ optionally includes one or two additional heteroatoms N or O in the ring structure, and wherein $R^{10}$ may optionally be substituted with one, two or three substituents independently selected from halo, —CN, —OH, —NH$_2$, oxo (=O), =NH, $C_1$-$C_4$ alkyl, —O($C_1$-$C_4$ alkyl), —NH($C_1$-$C_4$ alkyl), —N($C_1$-$C_4$ alkyl)$_2$ or =NH($C_1$-$C_4$ alkyl); provided that at least one oxygen atom in the ring structure of $R^{10}$ is not directly attached to the same atom of $R^0$-$L^2$- that is directly attached to W, X, Y or Z;

each $R^6$ is independently selected from a $C_1$-$C_6$ alkyl, $C_2$-$C_6$ alkenyl, $C_2$-$C_6$ alkynyl or $C_3$-$C_6$ cyclic group, wherein the alkyl, alkenyl, alkynyl or cyclic group may optionally be substituted with one, two, three, four or five halo groups;

m is 0, 1 or 2;

$R^3$ and $R^4$ are hydrogen; and $R^2$ is a phenyl or a 5- or 6-membered heteroaryl group (such as phenyl, pyridinyl, pyridazinyl, pyrimidinyl, pyrazinyl, pyrrolyl, pyrazolyl or imidazolyl); wherein (i) the phenyl or 5- or 6-membered heteroaryl group is substituted at the α position with a substituent selected from —$R^7$, —$OR^7$ and —$COR^7$, wherein $R^7$ is selected from a $C_1$-$C_6$ alkyl, $C_2$-$C_6$ alkenyl, $C_2$-$C_6$ alkynyl or $C_3$-$C_6$ cyclic group and wherein $R^7$ is optionally substituted with one or more halo groups; and the phenyl or 5- or 6-membered heteroaryl group is further substituted at the α' position with a substituent selected from —$R^{17}$, —$OR^{17}$ and —$COR^{17}$, wherein $R^{17}$ is selected from a $C_1$-$C_6$ alkyl, $C_2$-$C_6$ alkenyl, $C_2$-$C_6$ alkynyl or $C_3$-$C_6$ cyclic group and wherein $R^{17}$ is optionally substituted with one or more halo groups; and optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is further substituted at the α' position with a substituent selected from —$R^7$, —$OR^7$ and —$COR^7$, wherein $R^7$ is selected from a $C_1$-$C_6$ alkyl, $C_2$-$C_6$ alkenyl, $C_2$-$C_6$ alkynyl or $C_3$-$C_6$ cyclic group and wherein $R^7$ is optionally substituted with one or more halo groups; and optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —R$^{18}$—OR$^{19}$, —R$^{18}$—N(R$^{19}$)$_2$, —R$^{18}$—CN or —R$^{18}$—C≡CR$^{19}$, and wherein a ring atom of the monovalent heterocyclic or aromatic group is directly attached to the α-ring atom of the parent phenyl or 5- or 6-membered heteroaryl group; wherein $R^{18}$ is independently selected from a bond or a $C_1$-$C_3$ alkylene group; and $R^{19}$ is independently selected from hydrogen or a $C_1$-$C_3$ alkyl or $C_1$-$C_3$ haloalkyl group; and the phenyl or 5- or 6-membered heteroaryl group is further substituted at the α' position with a substituent selected from —$R^7$, —$OR^7$ and —$COR^7$, wherein $R^7$ is selected from a $C_1$-$C_6$ alkyl, $C_2$-$C_6$ alkenyl, $C_2$-$C_6$ alkynyl or $C_3$-$C_6$ cyclic group and wherein $R^7$ is optionally substituted with one or more halo groups; and optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a $C_1$-$C_4$ alkyl or $C_1$-$C_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —R$^{18}$—OR$^{19}$, —R$^{18}$—N(R$^{19}$)$_2$, —R$^{18}$—CN or —R$^{18}$—C≡CR$^{19}$, and wherein a ring atom of the monovalent heterocyclic or aromatic group is directly attached to the α-ring atom of the parent phenyl or 5- or 6-membered heteroaryl group; wherein $R^{18}$ is independently selected from a bond or a $C_1$-$C_3$ alkylene group; and $R^{19}$ is independently selected from hydrogen or a $C_1$-$C_3$ alkyl or $C_1$-$C_3$ haloalkyl group; and the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group).

In one aspect of any of the above embodiments, the compound of formula (I) has a molecular weight of from 250 to 2,000 Da. Typically, the compound of formula (I) has a molecular weight of from 300 to 1,000 Da. Typically, the compound of formula (I) has a molecular weight of from 330 to 800 Da. More typically, the compound of formula (I) has a molecular weight of from 350 to 650 Da.

A second aspect of the invention provides a compound selected from the group consisting of:

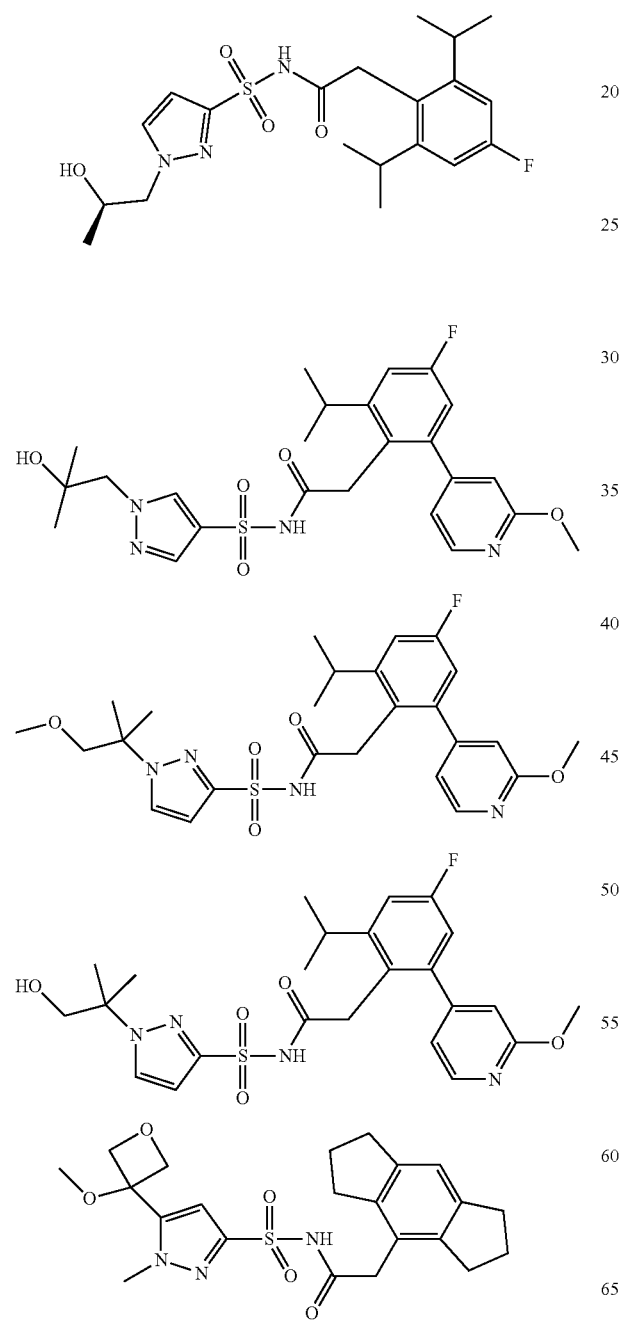

-continued

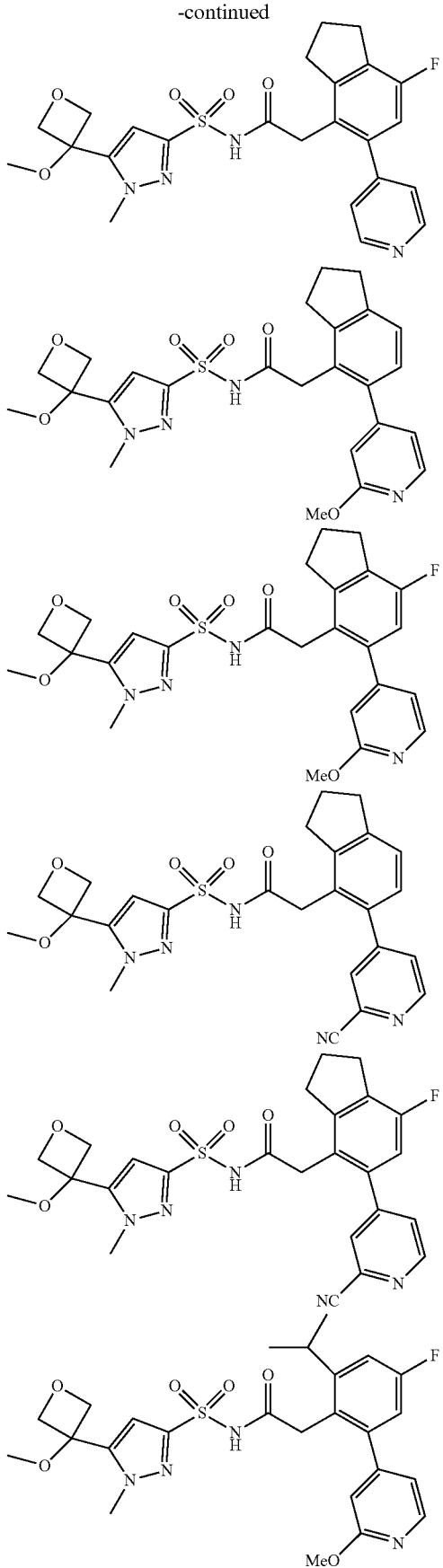

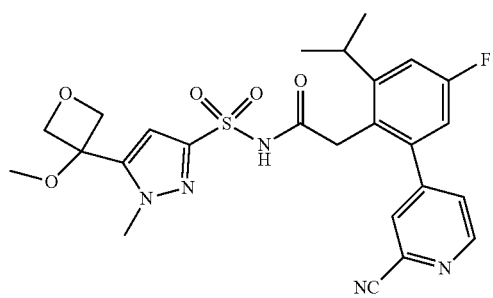
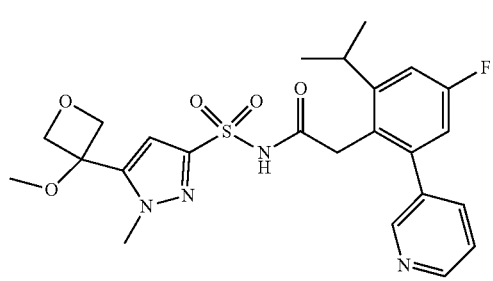
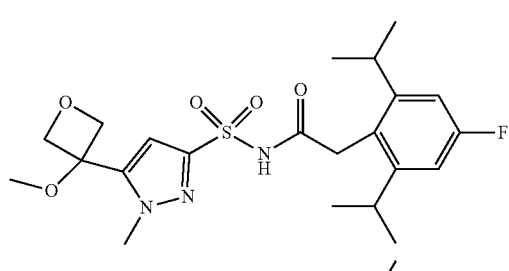
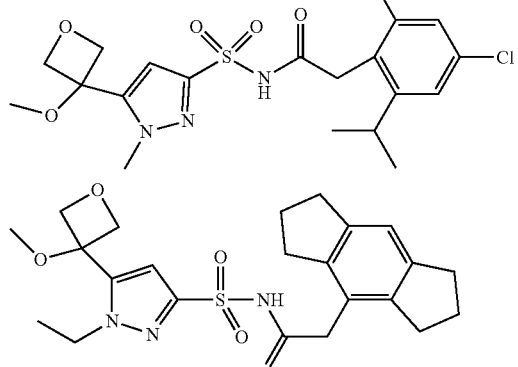
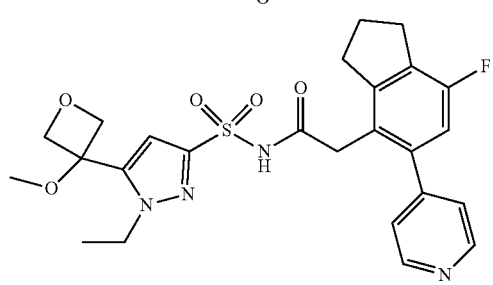
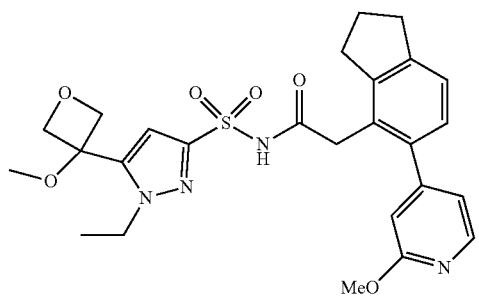
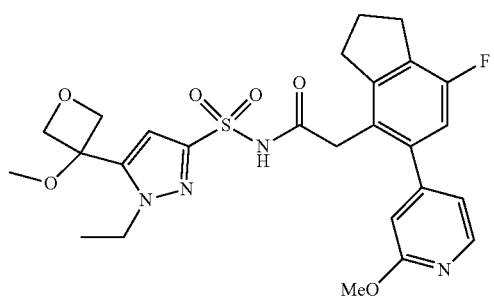
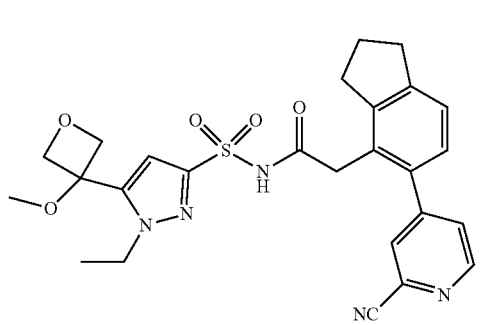
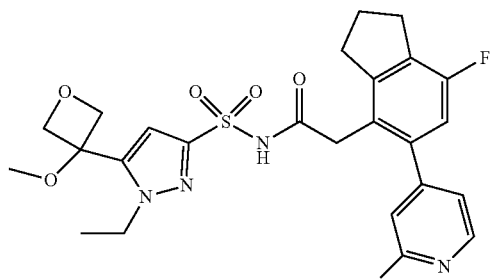
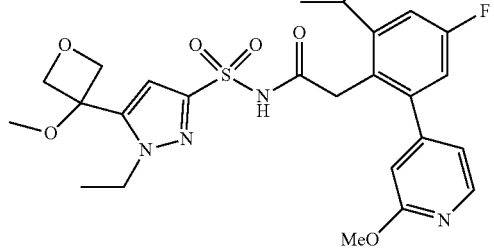

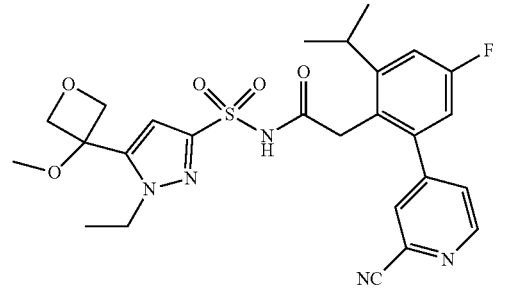
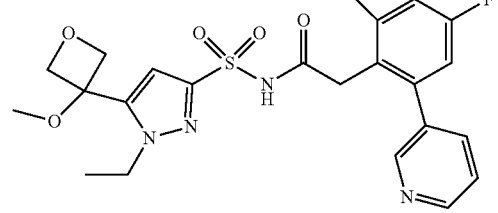
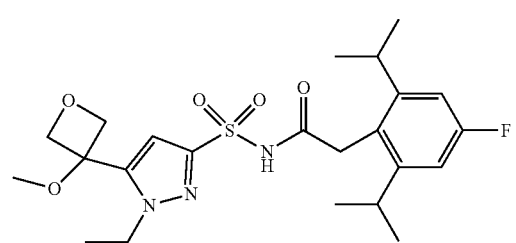
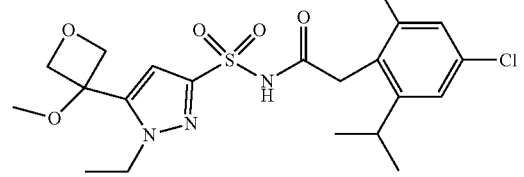
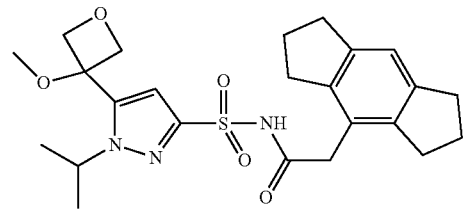
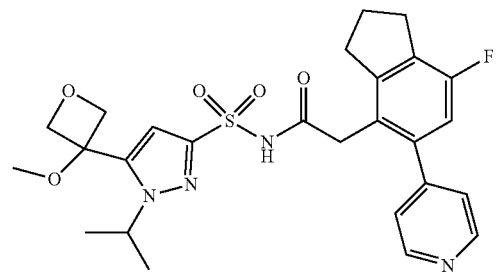
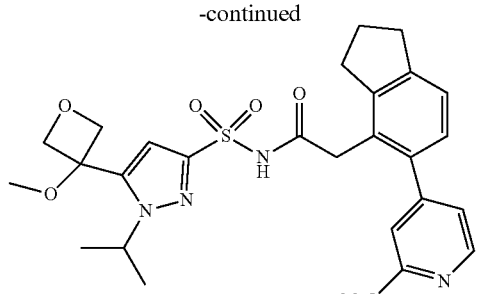
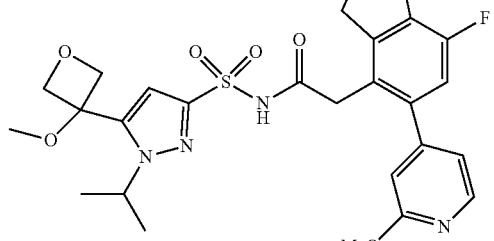
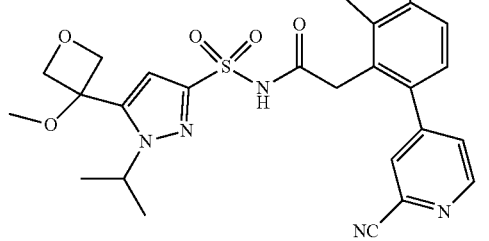
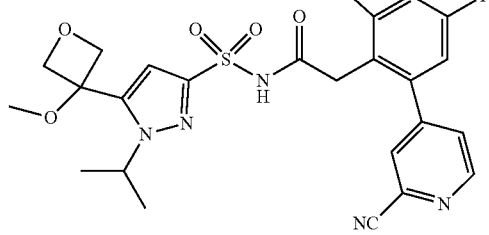
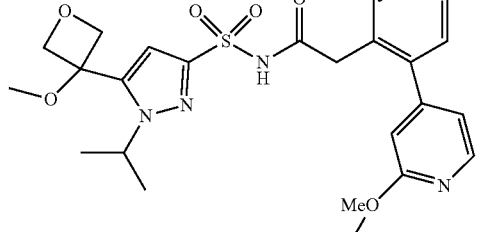
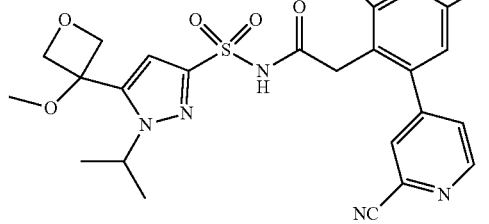

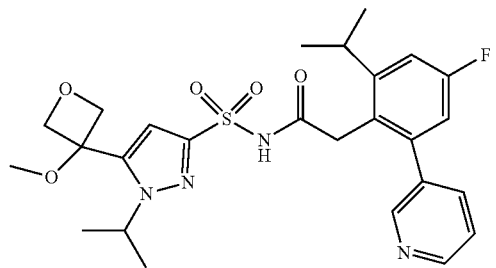
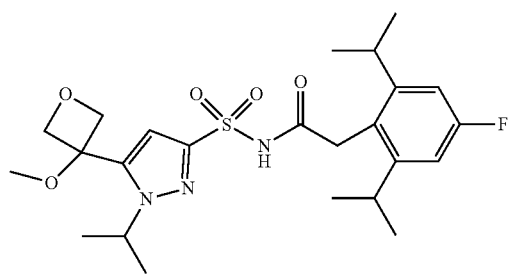
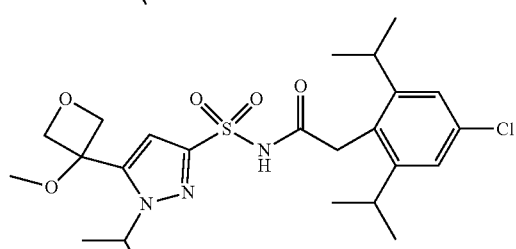
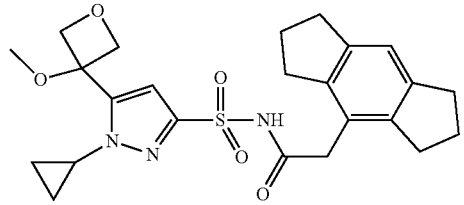
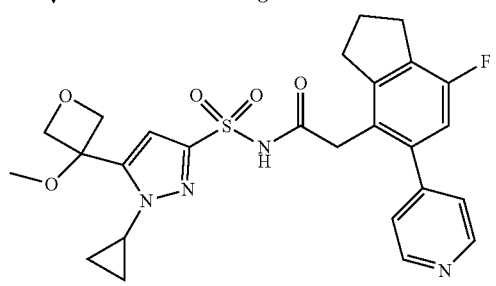
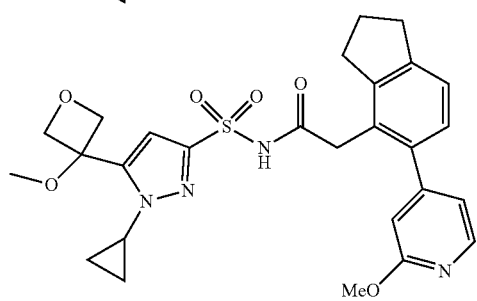
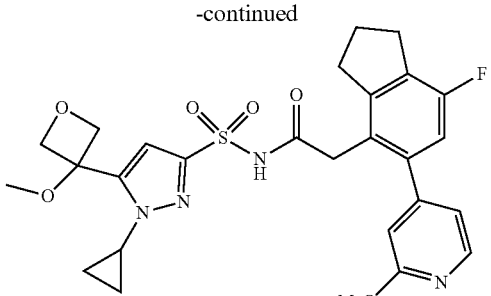
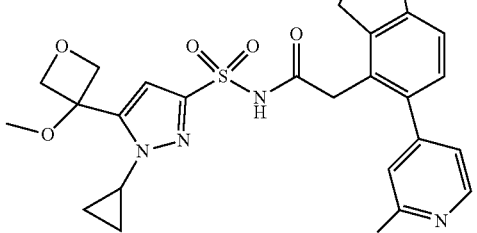
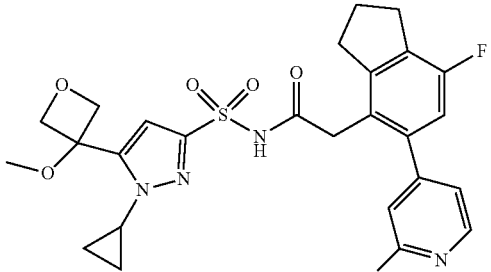
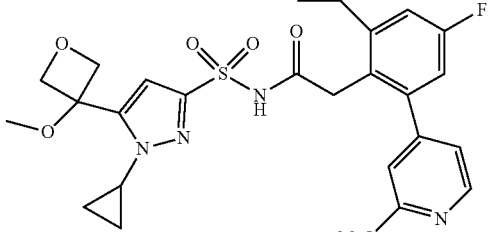
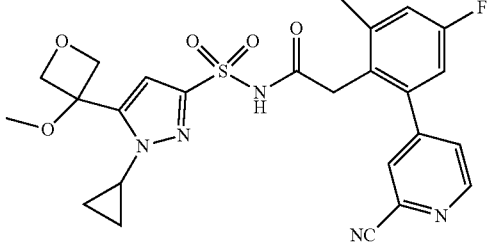
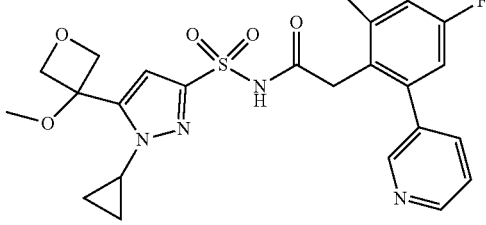

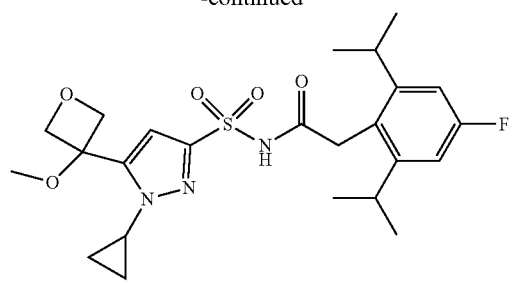
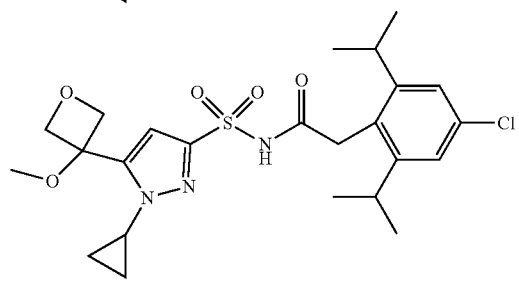
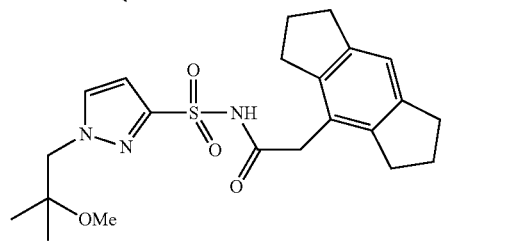
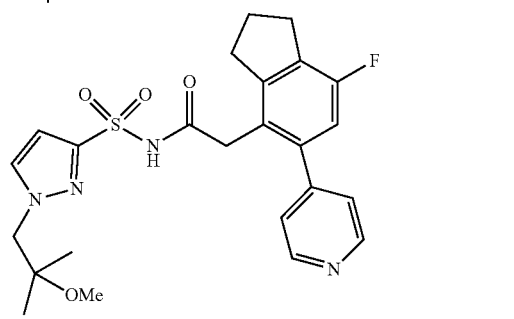
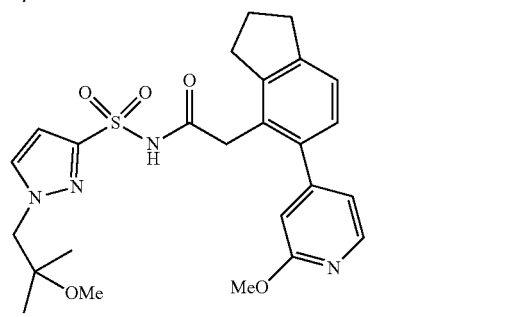
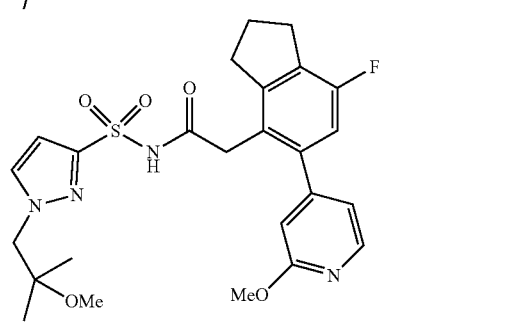
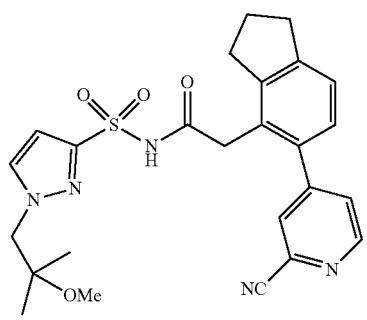
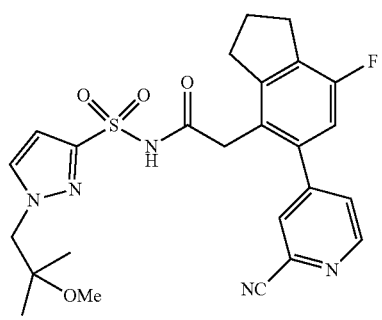
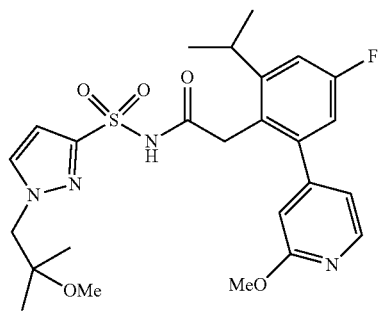
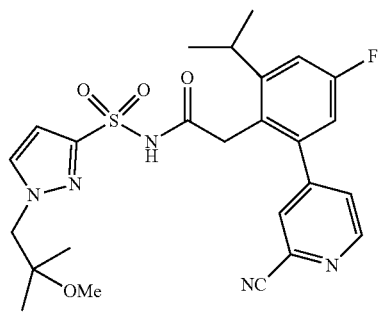
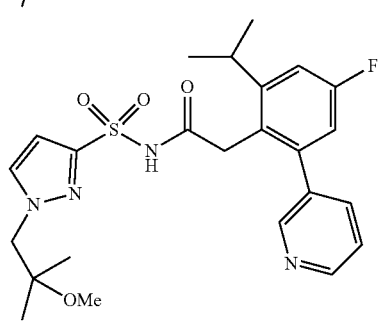

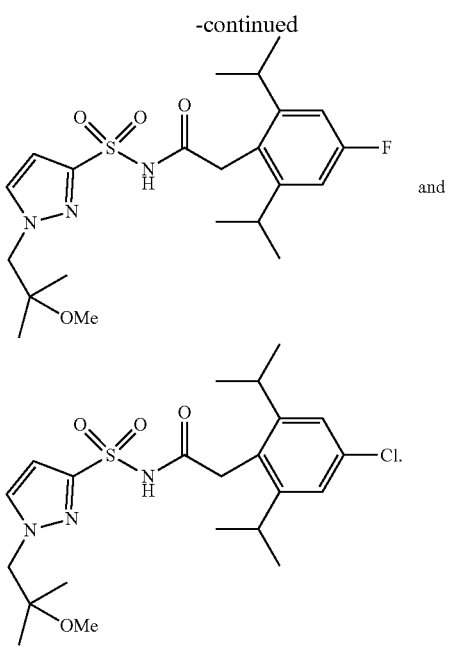

and

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such other solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention is a topical pharmaceutical composition. For example, the topical pharmaceutical composition may be a dermal pharmaceutical composition or an ocular pharmaceutical composition.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1p has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012149(4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014);

chronic kidney disease (Granata et al. PLoS One 2015 10(3): e0122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1p in cancer invasiveness, growth and metastasis, and inhibition of IL-1p with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13:1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), antisynthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;

(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuber-* culosis, *Mycobacterium leprae*, *Mycoplasma pneumoniae*, *Mycoplasma hominis*, *Neisseria meningitidis*, *Neisseria gonorrhoeae*, *Rickettsia rickettsii*, *Legionella pneumophila*, *Klebsiella pneumoniae*, *Pseudomonas aeruginosa*, *Propionibacterium acnes*, *Treponema pallidum*, *Chlamydia trachomatis*, *Vibrio cholerae*, *Salmonella typhimurium*, *Salmonella typhi*, *Borrelia burgdorferi* or *Yersinia pestis*), fungal infections (e.g. from *Candida* or *Aspergillus* species), protozoan infections (e.g. from *Plasmodium*, *Babesia*, *Giardia*, *Entamoeba*, *Leishmania* or Trypanosomes), helminth infections (e.g. from *Schistosoma*, roundworms, tapeworms or flukes) and prion infections;
- (v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;
- (vi) metabolic diseases such as type 2 diabetes (T2D), atherosclerosis, obesity, gout, and pseudo-gout;
- (vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;
- (viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;
- (ix) liver diseases including non-alcoholic fatty liver disease (NAFLD) and non-alcoholic steatohepatitis (NASH) including advanced fibrosis stages F3 and F4, alcoholic fatty liver disease (AFLD), and alcoholic steatohepatitis (ASH);
- (x) renal diseases including chronic kidney disease, oxalate nephropathy, nephrocalcinosis, glomerulonephritis, and diabetic nephropathy;
- (xi) ocular diseases including those of the ocular epithelium, age-related macular degeneration (AMD) (dry and wet), uveitis, corneal infection, diabetic retinopathy, optic nerve damage, dry eye, and glaucoma;
- (xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;
- (xiii) lymphatic conditions such as lymphangitis and Castleman's disease;
- (xiv) psychological disorders such as depression and psychological stress;
- (xv) graft versus host disease;
- (xvi) allodynia including mechanical allodynia; and
- (xvii) any disease where an individual has been determined to carry a germline or somatic non-silent mutation in NLRP3.

In one embodiment, the disease, disorder or condition is selected from:
- (i) cancer;
- (ii) an infection;
- (iii) a central nervous system disease;
- (iv) a cardiovascular disease;
- (v) a liver disease;
- (vi) an ocular disease; or
- (vii) a skin disease.

More typically, the disease, disorder or condition is selected from:
- (i) cancer;
- (ii) an infection;
- (iii) a central nervous system disease; or
- (iv) a cardiovascular disease.

In one embodiment, the disease, disorder or condition is selected from:
- (i) acne conglobata;
- (ii) atopic dermatitis;
- (iii) Alzheimer's disease;
- (iv) amyotrophic lateral sclerosis;
- (v) age-related macular degeneration (AMD);
- (vi) anaplastic thyroid cancer;
- (vii) cryopyrin-associated periodic syndromes (CAPS);
- (viii) contact dermatitis;
- (ix) cystic fibrosis;
- (x) congestive heart failure;
- (xi) chronic kidney disease;
- (xii) Crohn's disease;
- (xiii) familial cold autoinflammatory syndrome (FCAS);
- (xiv) Huntington's disease;
- (xv) heart failure;
- (xvi) heart failure with preserved ejection fraction;
- (xvii) ischemic reperfusion injury;
- (xviii) juvenile idiopathic arthritis;
- (xix) myocardial infarction;
- (xx) macrophage activation syndrome;
- (xxi) myelodysplastic syndrome;
- (xxii) multiple myeloma;
- (xxiii) motor neuron disease;
- (xxiv) multiple sclerosis;
- (xxv) Muckle-Wells syndrome;
- (xxvi) non-alcoholic steatohepatitis (NASH);
- (xxvii) neonatal-onset multisystem inflammatory disease (NOMID);
- (xxviii) Parkinson's disease;
- (xxix) systemic juvenile idiopathic arthritis;
- (xxx) systemic lupus erythematosus;
- (xxxi) traumatic brain injury;
- (xxxii) transient ischemic attack; and
- (xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:
- (i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
- (ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);
- (iii) a muscular condition such as polymyositis or myasthenia gravis;
- (iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure; and/or (xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

In one embodiment of the fifth, sixth, seventh, eighth, ninth or tenth aspect of the invention, the disease, disorder or condition is not a metabolic disease such as diabetes, or a disease that is treatable with an estrogen-related receptor-α (ERR-α) modulator, or a disease that is treatable with a muscle stimulant.

In one embodiment of the fifth, sixth, seventh, eighth, ninth or tenth aspect of the present invention, the treatment or prevention comprises topically administering a compound of the first or second aspect, or a pharmaceutically acceptable salt, solvate or prodrug of the third aspect, or a pharmaceutical composition of the fourth aspect. For example, the disease, disorder or condition may be a skin disease or condition, wherein the treatment or prevention comprises topically administering a compound of the first or second aspect, or a pharmaceutically acceptable salt, solvate or prodrug of the third aspect, or a pharmaceutical composition of the fourth aspect to the skin. Alternatively, the disease, disorder or condition may be an ocular disease or condition, wherein the treatment or prevention comprises topically administering a compound of the first or second aspect, or a pharmaceutically acceptable salt, solvate or prodrug of the third aspect, or a pharmaceutical composition of the fourth aspect to the eye.

In one embodiment, where the treatment or prevention comprises topically administering a compound of the first or second aspect, or a pharmaceutically acceptable salt, solvate or prodrug of the third aspect, or a pharmaceutical composition of the fourth aspect of the invention, one or more further active agents may be co-administered. The one or more further active agents may also be topically administered, or may be administered via a non-topical route. Typically, the one or more further active agents are also topically administered. For example, where the pharmaceutical composition of the fourth aspect of the invention is a topical pharmaceutical composition, the pharmaceutical composition may further comprise one or more further active agents.

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
(i) chemotherapeutic agents;
(ii) antibodies;
(iii) alkylating agents;
(iv) anti-metabolites;
(v) anti-angiogenic agents;
(vi) plant alkaloids and/or terpenoids;
(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulfonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositomomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a vinca alkaloid, a podophyllotoxin and/or a taxane. In some embodiments, the one or more vinca alkaloids may be derived from the Madagascar periwinkle, Catharanthus roseus (formerly known as Vinca rosea), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic dinucleotides, such as cAMP, cGMP, and cGAMP, and/or modified cyclic di-nucleotides that may include one or more of the following modification features: 2'-0/3'-0 linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCB024360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations. For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disease, disorder or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES—COMPOUND SYNTHESIS

All solvents, reagents and compounds were purchased and used without further purification unless stated otherwise.

Abbreviations

2-MeTHF 2-methyltetrahydrofuran
$Ac_2O$ acetic anhydride
AcOH acetic acid
aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DAST diethylaminosulfur trifluoride
DCE 1,2-dichloroethane, also called ethylene dichloride
DCM dichloromethane
DIPEA N,N-diisopropylethylamine, also called Hünig's base
DMA dimethylacetamide
DMAP 4-dimethylaminopyridine, also called N,N-dimethylpyridin-4-amine
DME dimethoxyethane
DMF N,N-dimethylformamide
DMSO dimethyl sulfoxide
EDC 1-ethyl-3-(3-dimethylaminopropyl)carbodiimide
eq or equiv equivalent
(ES$^+$) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)$^+$ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaHMDS sodium hexamethyldisilazide, also called sodium bis(trimethylsilyl)amide
NaO$^t$Bu sodium tert-butoxide
NBS 1-bromopyrrolidine-2,5-dione, also called N-bromosuccinimide
NCS 1-chloropyrrolidine-2,5-dione, also called N-chlorosuccinimide NMP N-methylpyrrolidine
NMR nuclear magnetic resonance (spectroscopy)
Pd(OAc)$_2$ palladium acetate
Pd(dba)$_2$ bis(dibenzylideneacetone) palladium(0)
Pd$_2$(dba)$_3$ tris(dibenzylideneacetone) dipalladium(0)
Pd(dppf)Cl$_2$ [1,1'-bis(diphenylphosphino)ferrocene] dichloropalladium(II)
PE petroleum ether
Ph phenyl
PMB p-methoxybenzyl, also called 4-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
sat saturated
SCX solid supported cation exchange (resin)
SEM 2-(trimethylsilyl)ethoxymethyl
sept septuplet
t triplet
T3P propylphosphonicanhydride
TBME tert-butyl methyl ether, also called methyl tert-butyl ether
TBSCl tert-butyldimethylsilyl chloride
TEA triethylamine
TFAA 2,2,2-trifluoroacetic acid anhydride
TFA 2,2,2-trifluoroacetic acid
THF tetrahydrofuran
TLC thin layer chromatography
TMSCl trimethylsilyl chloride
wt % weight percent or percent by weight
XantPhos® 4,5-bis(diphenylphosphino)-9,9-dimethylxanthene
Xphos® 2-dicyclohexylphosphino-2',4',6'-triisopropylbiphenyl
XtalFluor-E® (diethylamino)difluorosulfonium tetrafluoroborate Experimental Methods
Analytical Methods NMR spectra were recorded at 300, 400 or 500 MHz with chemical shifts reported in parts per million. Spectra were measured at 298 K, unless indicated otherwise, and were referenced relative to the solvent resonance. Spectra were collected using one of the machines below:—
  An Agilent VNMRS 300 instrument fitted with a 7.05 Tesla magnet from Oxford instruments, indirect detection probe and direct drive console including PFG module.
  An Agilent MercuryPlus 300 instrument fitted with a 7.05 Tesla magnet from Oxford instruments, 4 nuclei auto-switchable probe and Mercury plus console.
  A Bruker Avance III spectrometer at 400 MHz fitted with a BBO 5 mm liquid probe.
  A Bruker 400 MHz spectrometer using ICON-NMR, under TopSpin program control.
  A Bruker Avance III HD spectrometer at 500 MHz, equipped with a Bruker 5 mm SmartProbe™.

HPLC and LC-MS were recorded on an Agilent 1290 series with UV detector and HP 6130 MSD mass detector. Mobile phase A: ammonium acetate (10 mM); water/MeOH/acetonitrile (900:60:40); mobile phase B: ammonium acetate (10 mM); water/MeOH/acetonitrile (100:540:360); column, Waters XBridge BEH C18 XP (2.1×50 mm, 2.5 µm).

Pump flow: 0.6 mL/min
Injection volume: 0.2 µL
Column temperature: 35° C.
UV detection: 215, 238 nm
Run time: 4.0 min
Mass detection: API-ES +ve and −ive Pump Program:

| Gradient Time (min) | % A | % B |
|---|---|---|
| 0.0 | 80 | 20 |
| 0.5 | 80 | 20 |
| 2.0 | 0 | 100 |

Alternatively LC-MS were recorded using SHIMADZU LCMS-2020, Agilent 1200 LC/G1956A MSD and Agilent 1200\G6110A, or Agilent 1200 LC & Agilent 6110 MSD. Mobile Phase: A: 0.025% NH$_3$·H$_2$O in water (v/v); B: Acetonitrile. Column: Kinetex EVO C18 2.1×30 mm, 5 µm.

Reversed Phase HPLC Conditions for the LCMS Analytical Methods

Methods 1a and 1b: Waters Xselect CSH C18 XP column (4.6×30 mm, 2.5 µm) at 40° C.; flow rate 2.5-4.5 mL min-1 eluted with a H$_2$O-MeCN gradient containing either 0.1% v/v formic acid (Method 1a) or 10 mM NH$_4$HCO$_3$ in water (Method 1b) over 4 min employing UV detection at 254 nm.

Method 1c: Agilent 1290 series with UV detector and HP 6130 MSD mass detector using Waters XBridge BEH C18 XP column (2.1×50 mm, 2.5 µm) at 35° C.; flow rate 0.6 mL/min; mobile phase A: ammonium acetate (10 mM); water/MeOH/acetonitrile (900:60:40); mobile phase B: ammonium acetate (10 mM); water/MeOH/acetonitrile (100:540:360); over 4 min employing UV detection at 215 and 238 nm.

Reversed Phase HPLC Conditions for the UPLC Analytical Methods

Methods 2a and 2b: Waters BEH C18 (2.1×30 mm, 1.7 µm) at 40° C.; flow rate 0.77 mL min$^{-1}$ eluted with a H$_2$O-MeCN gradient containing either 0.1% v/v formic acid (Method 2a) or 10 mM NH$_4$HCO$_3$ in water (Method 2b) over 3 min employing UV detection at 254 nm.

Purification Method 1

Automated reversed phase column chromatography was carried out using a Buchi Sepracore® X50 system driven by a C-605 pump module, C-620 Sepracore control package, C-640 UV photometer detection unit and C-660 fraction collector.

Revelis C18 Reversed-Phase 12 g Cartridge

| | |
|---|---|
| Carbon loading | 18% |
| Surface area | 568 m$^2$/g |
| Pore diameter | 65 Angstrom |
| pH (5% slurry) | 5.1 |
| Average particle size | 40 µm |

The column was conditioned before use with MeOH (5 min), then brought to H$_2$O (in 5 min) and kept 5 min at H$_2$O. Flow rate=30 mL/min.

Separation runs:

| Time (min) | A: water (%) | B: MeOH (%) |
|---|---|---|
| 0 | 100 | 0 |
| 5 | 100 | 0 |
| 30 | 30 | 70 |

-continued

| Time (min) | A: water (%) | B: MeOH (%) |
|---|---|---|
| 30.1 | 0 | 100 |
| 35 | 0 | 100 |

Detection wavelength: 215, 235, 254 and 280 nm. Before each new run, the cartridge was cleaned using the conditioning method.

Purification Method 2

Preparative column chromatography was carried out using a Waters prep system driven by a 2767 Sample Manager, SFO System Fluidics Organizer, 515 HPLC Pumps, 2545 Binary Gradient Module, 2998 Photodiode Array Detector, SQD Detector 2 with ESI mass. Mobile phase ACD: acetonitrile; mobile phase A: ammonium acetate (10 mM); mobile phase B: acetonitrile; column, XSelect CSH Prep C18 OBD (100×30 mm; 5 μm).

| Pump flow: 40 mL/min | Injection volume: 1.5 mL |
|---|---|
| Run time: 15.0 min | Column temperature: not controlled |
| Mass detection: API-ES +ve and −ive | |

Pump Program:

| Time (min) | Flow (ml/min) Bin. pump | Flow (ml/min) ACD pump | % A | % B |
|---|---|---|---|---|
| 0.0 | 22 | 4 | 85 | 15 |
| 2.0 | 38 | 2 | 85 | 15 |
| 2.5 | 38 | 2 | 85 | 15 |
| 10.0 | 38 | 2 | 65 | 35 |
| 10.1 | 38 | 2 | 5 | 95 |
| 12.0 | 38 | 2 | 5 | 95 |
| 12.1 | 38 | 2 | 85 | 15 |
| 15.0 | 38 | 2 | 85 | 15 |

Purification Method 3 (Acidic Prep)

Preparative reversed phase HPLC was carried out using a Waters X-Select CSH column C18, 5 μm (19×50 mm), flow rate 28 mL min-1 eluting with a H₂O-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Purification Method 4 (Basic Prep)

Preparative reversed phase HPLC was carried out using a Waters X-Bridge Prep column C18, 5 μm (19×50 mm), flow rate 28 mL min-1 eluting with a 10 mM NH₄HCO₃-MeCN gradient over 6.5 min using UV detection at 254 nm. Gradient information: 0.0-0.2 min, 10% MeCN; 0.2-5.5 min, ramped from 10% MeCN to 40% MeCN; 5.5-5.6 min, ramped from 40% MeCN to 95% MeCN; 5.6-6.5 min, held at 95% MeCN.

Alternatively automated reversed phase HPLC column chromatography purification was carried out using:
(i) a Gilson GX-281 system driven by a Gilson-322 pump module, Gilson-156 UV photometer detection unit and Gilson-281 fraction collector. Detection wavelength: 220 nm and 254 nm and 215 nm.
(ii) a Gilson GX-215 system driven by a LC-20AP pump module, SPD-20A UV photometer detection unit and Gilson-215 fraction collector. Detection wavelength: 220 nm and 254 nm and 215 nm.
(iii) a TELEDYNE ISCO CombiFlash Rf+150. Detection wavelength: 220 nm and 254 nm and 215 nm.
(iv) a Shimadzu CBM-20A system driven by LC-20AP pump module, SPD-20A UV photometer detection unit and FRC-10A fraction collector. Detection wavelength: 220 nm and 254 nm and 215 nm.

Synthesis of Intermediates

Intermediate A1: 2-(5-(2-Cyanopyridin-4-yl)-2,3-dihydro-1H-inden-4-yl)acetyl chloride Step A: 5-(Benzyloxy)-4-bromo-2,3-dihydro-1H-indene

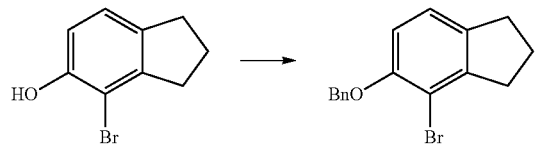 [SMILES: Oc1ccc2c(c1Br)CCC2 ; Brc1c(OCc2ccccc2)ccc2c1CCC2]

To a solution of 4-bromo-2,3-dihydro-1H-inden-5-ol (1.36 g, 6.38 mmol, 1 eq) (Hunsberger et al., JACS, 1955, vol. 77(9), pages 2466-2475) in dimethylformamide (35 mL) was added potassium carbonate (1.76 g, 12.8 mmol, 2 eq) and benzyl bromide (0.83 mL, 7.02 mmol, 1.1 eq). The reaction mixture was heated to 60° C. After stirring for 1.5 hours, the mixture was cooled to room temperature and diluted with diethyl ether. The organic layer was washed 4 times with water, once with brine, dried over sodium sulfate and then concentrated in vacuo to afford the title compound (1.83 g, 6.04 mmol, 94%).

¹H NMR (300 MHz, CDCl₃) δ 7.52-7.46 (m, 2H), 7.42-7.29 (m, 3H), 7.03 (d, 1H), 6.72 (d, 1H), 5.13 (s, 2H), 2.96 (t, 4H), 2.10 (p, 2H).

Step B: tert-Butyl 2-(5-(benzyloxy)-2,3-dihydro-1H-inden-4-yl)acetate

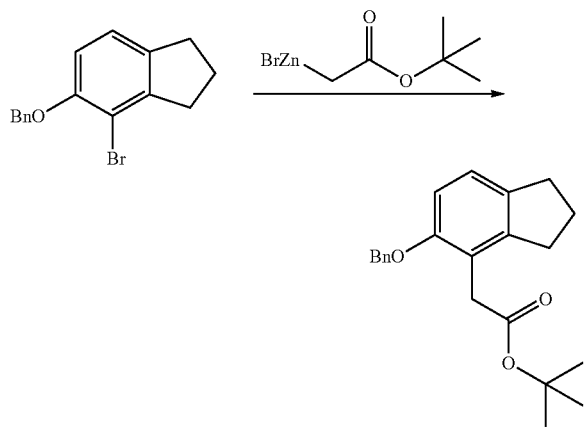

A solution of 5-(benzyloxy)-4-bromo-2,3-dihydro-1H-indene (1.83 g, 6.04 mmol, 1 eq) in anhydrous tetrahydrofuran (50 mL) was bubbled through with nitrogen for 20 minutes. To the degassed solution was added tris(dibenzylideneacetone)dipalladium(0)-chloroform adduct (312 mg, 302 μmol, 0.05 eq) and dicyclohexyl(2',4',6'-triisopropyl-[1,1'- biphenyl]-2-yl)phosphane (288 mg, 604 µmol, 0.1 eq). The reaction mixture was stirred for 30 minutes at room temperature. After that, (2-(tert-butoxy)-2-oxoethyl) zinc (II) bromide (Intermediate A2, Step D) in THF (0.55 molar, 22 mL, 12.1 mmol, 2 eq) was added and the reaction mixture was heated in a sand bath at 70° C. After stirring for 1 hour, the reaction mixture was cooled to room temperature and then diluted with diethyl ether. The reaction mixture was washed twice with saturated ammonium chloride, once with brine, dried over sodium sulfate, filtered and then concentrated in vacuo. The crude product was submitted to normal phase flash chromatography using heptane and ethyl acetate as eluent to afford the title compound (1.82 g, 5.38 mmol, 89%).

$^1$H NMR (300 MHz, CDCl$_3$) 7.44 (d, 2H), 7.40-7.29 (m 3H), 7.05 (d, 1H), 6.72 (d, 1H), 5.06 (s, 2H), 3.62 (s, 2H), 2.87 (t, 4H), 2.08 (p, 2H), 1.40 (s, 9H).

Step C: tert-Butyl 2-(5-hydroxy-2,3-dihydro-1H-inden-4-yl)acetate

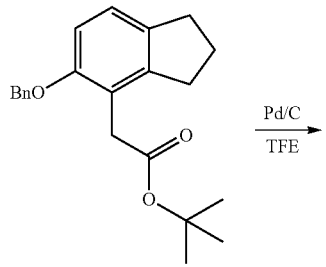

A solution of tert-butyl 2-(5-(benzyloxy)-2,3-dihydro-1H-inden-4-yl)acetate (1.82 g, 5.38 mmol, 1 eq) in 2,2,2-trifluoroethanol (50 mL) was bubbled through with nitrogen for 20 minutes. After that, Pd/C (10 wt % loading, matrix activated carbon support, 0.57 g, 538 µmol, 0.1 eq) was added and the flask was charged with hydrogen. The reaction mixture was stirred under a hydrogen atmosphere. After 1.5 hours of stirring, another batch of Pd/C (10 wt % loading, matrix activated carbon support, 0.57 g, 538 µmol, 0.1 eq) was added. After stirring over the weekend, the reaction mixture was filtered over Celite®, and the residue was washed extensively with ethyl acetate. The filtrates were combined and concentrated in vacuo to afford the title compound (1.28 g, 5.15 mmol, 95%).

$^1$H NMR (300 MHz, CDCl$_3$) δ 7.33 (bs, 1H), 7.01 (d, 1H), 6.76 (d, 1H), 3.57 (s, 2H), 2.88 (td, 4H), 2.15-1.96 (m, 2H), 1.46 (s, 9H).

Step D: tert-Butyl 2-(5-(((trifluoromethyl)sulfonyl)oxy)-2,3-dihydro-1H-inden-4-yl)acetate

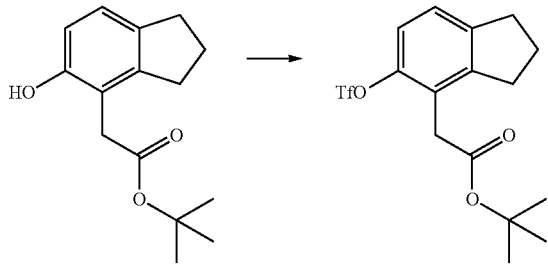 [SMILES: CC(C)(C)OC(=O)Cc1c(O)ccc2c1CCC2 ; CC(C)(C)OC(=O)Cc1c(OS(=O)(=O)C(F)(F)F)ccc2c1CCC2]

A solution of tert-butyl 2-(5-hydroxy-2,3-dihydro-1H-inden-4-yl)acetate (1.28 g, 5.15 mmol, 1 eq) and triethylamine (1.4 mL, 10.3 mmol, 2 eq) in dichloromethane (50 mL) was cooled in an ice bath. To the cooled greenish solution was added dropwise triflic anhydride (0.87 mL, 5.15 mmol, 1 eq). After complete addition, the cooling bath was removed and the reaction mixture was allowed to reach room temperature. After 1 hour of stirring, the reaction mixture was washed three times with saturated sodium bicarbonate solution, once with brine, dried over sodium sulfate, filtered and then concentrated in vacuo to afford the title compound (1.74 g, 4.57 mmol, 88%).

$^1$H NMR (300 MHz, CDCl$_3$) δ 7.17 (d, 1H), 7.07 (d, 1H), 3.63 (s, 2H), 2.92 (dt, 4H), 2.14 (p, 2H), 1.44 (s, 9H).

Step E: tert-Butyl 2-(5-(4,4,5,5-tetramethyl-1,3,2-dioxaborolan-2-yl)-2,3-dihydro-1H-inden-4-yl)acetate

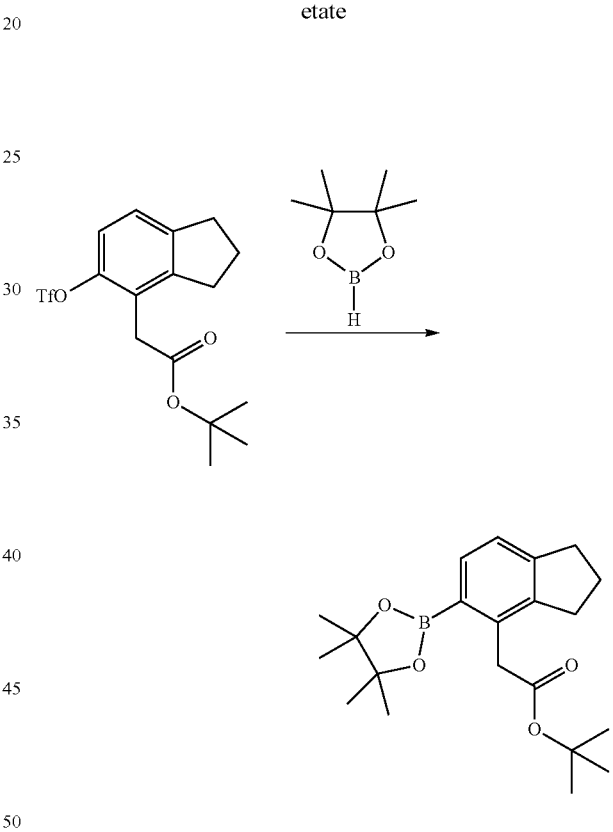

A solution of tert-butyl 2-(5-(((trifluoromethyl)sulfonyl)oxy)-2,3-dihydro-1H-inden-4-yl)acetate (4.64 g, 12.2 mmol, 1 eq) in 1,4-dioxane (61 mL) was degassed with nitrogen. After that, 4,4,5,5-tetramethyl-1,3,2-dioxaborolane (5.3 mL, 36.6 mmol, 3.9 eq), triethylamine (10 mL, 73.2 mmol, 6.0 eq) and [1,1'-bis(diphenylphosphino)ferrocene]dichloropalladium(II) adduct (498 mg, 610 µmol, 0.05 eq) was added. The reaction mixture was heated in a sand bath set at 100° C. After stirring overnight, the reaction mixture was concentrated in vacuo. The crude product was submitted to normal phase flash chromatography using heptane and ethyl acetate as eluent to afford the title compound (3.79 g, 10.5 mmol, 86%).

$^1$H NMR (300 MHz, CDCl$_3$) δ 7.63 (d, 1H), 7.13 (d, 1H), 3.92 (d, 2H), 2.90 (dt, 4H), 2.04 (p, 2H), 1.42 (s, 9H), 1.32 (s, 12H).

Step F: tert-Butyl 2-(5-(2-cyanopyridin-4-yl)-2,3-dihydro-1H-inden-4-yl)acetate

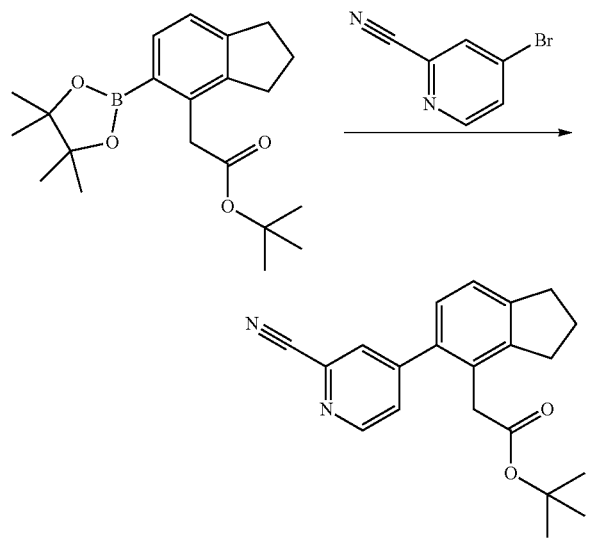

A solution of tert-butyl 2-(5-(4,4,5,5-tetramethyl-1,3,2-dioxaborolan-2-yl)-2,3-dihydro-1H-inden-4-yl)acetate (3.74 g, 10.4 mmol, 1 eq) and 4-bromopicolinonitrile (2.29 g, 12.5 mmol, 1.2 eq) in acetonitrile (74 mL) and water (30 mL) was degassed with nitrogen. Then sodium carbonate (1.77 g, 16.7 mmol, 1.6 eq) and [1,1'-bis(diphenylphosphino)ferrocene]dichloropalladium(II) adduct (852 mg, 1.04 mmol, 0.1 eq) were added. The reaction mixture was heated in a sand bath set at 80° C. After 50 minutes, the reaction mixture was cooled to room temperature, diluted with water and then extracted with ethyl acetate. The organic layer was washed with brine, dried over sodium sulfate, filtered and then concentrated in vacuo. The crude product was submitted to normal phase flash chromatography using ethyl acetate and heptane as eluent to afford the title compound (2.63 g, 7.86 mmol, 75%).

$^1$H NMR (300 MHz, CDCl$_3$) δ 8.71 (dd, 1H), 7.72 (dd, 1H), 7.52 (dd, 1H), 7.24 (d, 1H), 7.01 (d, 1H), 3.42 (s, 2H), 3.01 (t, 2H), 2.92 (t, 2H), 2.15 (p, 2H), 1.43 (s, 9H).

Step G: 2-(5-(2-Cyanopyridin-4-yl)-2,3-dihydro-1H-inden-4-yl)acetic acid TFA Salt and 2-(5-(2-carbamoylpyridin-4-yl)-2,3-dihydro-1H-inden-4-yl)acetic acid TFA Salt in Ratio ~7:3

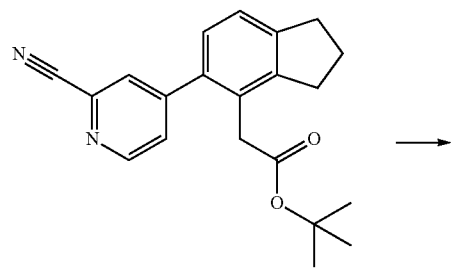

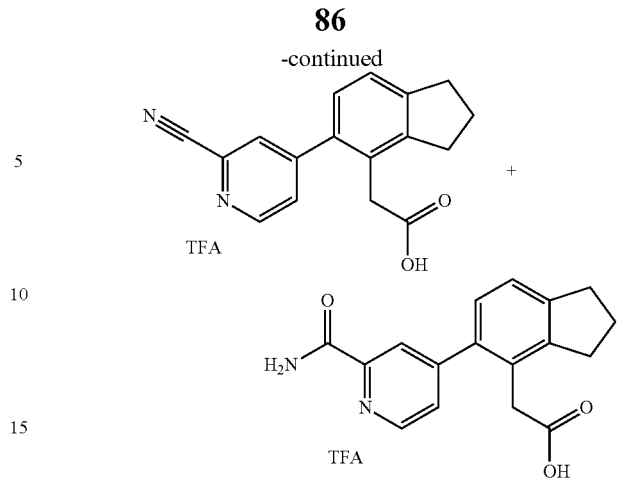

To a solution of tert-butyl 2-(5-(2-cyanopyridin-4-yl)-2,3-dihydro-1H-inden-4-yl)acetate (2.63 g, 7.86 mmol, 1 eq) in dichloromethane (20 mL) was added trifluoroacetic acid (20 mL, 0.26 mol, 33 eq). The reaction mixture was stirred at room temperature for 2.5 hours and then toluene (40 mL) was added. The reaction mixture was concentrated to about 40 mL, and then again toluene (40 mL) was added; this process was done twice. Then all solvents were evaporated in vacuo to afford 2-(5-(2-cyanopyridin-4-yl)-2,3-dihydro-1H-inden-4-yl)acetic acid (2.92 g, 94%) as a ~7:3 mixture with 2-(5-(2-carbamoylpyridin-4-yl)-2,3-dihydro-1H-inden-4-yl)acetic acid both as the TFA salt.

$^1$H NMR (of 2-(5-(2-cyanopyridin-4-yl)-2,3-dihydro-1H-inden-4-yl)acetic acid) (300 MHz, CDCl$_3$) δ 8.78 (d, 1H), 7.74 (d, 1H), 7.58 (dd, 1H), 7.34-7.25 (m, 1H), 7.03 (d, 1H), 3.58 (d, 2H), 3.04 (d, 2H), 2.94 (t, 2H), 2.17 (p, 2H).

Step H: 2-(5-(2-Cyanopyridin-4-yl)-2,3-dihydro-1H-inden-4-yl)acetyl chloride

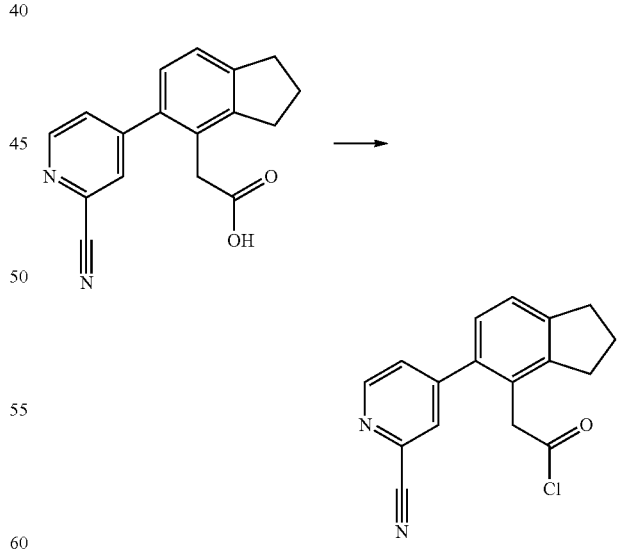

To a solution of 2-(5-(2-cyanopyridin-4-yl)-2,3-dihydro-1H-inden-4-yl)acetic acid (non salt form) (34 mg, 0.12 mmol, 1 eq) in anhydrous dichloromethane (2 mL) was added one drop of dimethylformamide and after that dropwise oxalyl chloride (32 µL, 0.37 mmol, 3 eq) at room temperature. After stirring for 1 hour, the volatiles were removed in vacuo and the crude product was used for the following step without any purification.

Intermediate A2:
2-(4-Fluoro-2,6-diisopropylphenyl)acetic acid Step A: 4-Fluoro-2,6-di(prop-1-en-2-yl)aniline

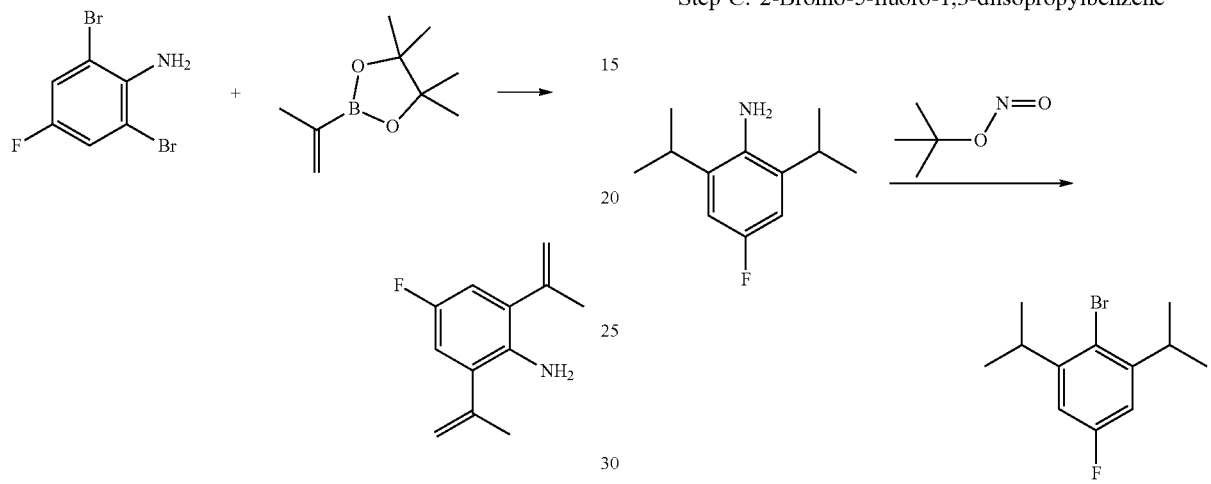

A solution of 2,6-dibromo-4-fluoroaniline (10 g, 1 eq), 4,4,5,5-tetramethyl-2-(prop-1-en-2-yl)-1,3,2-dioxaborolane (16.67 g, 2.67 eq), Cs$_2$CO$_3$ (36.35 g, 3 eq) and Pd(dppf)Cl$_2$ (2.72 g, 3.72 mmol, 0.1 eq) in dioxane (100 mL) and H$_2$O (10 mL) was degassed under reduced pressure. The reaction mixture was heated to 100° C. for 3 hours under nitrogen. Then the reaction mixture was quenched by addition of H$_2$O (200 mL), diluted with EtOAc (150 mL), and extracted with EtOAc (2×150 mL). The combined organic layers were washed with brine (2×200 mL), dried over anhydrous Na$_2$SO$_4$, filtered and concentrated under reduced pressure. The residue was purified by column chromatography (SiO$_2$, petroleum ether:ethyl acetate, 1:0 to 100:1) to give the title compound (8 g, 89% yield, 78.9% purity on LCMS) as a yellow oil.

$^1$H NMR (400 MHz, CDCl$_3$) δ 6.68 (d, 2H), 5.32-5.31 (m, 2H), 5.08 (d, 2H), 3.84 (s, 2H) and 2.07 (d, 6H).

LCMS: m/z 192.2 (M+H)$^+$ (ES$^+$).

Step B: 4-Fluoro-2,6-diisopropylaniline

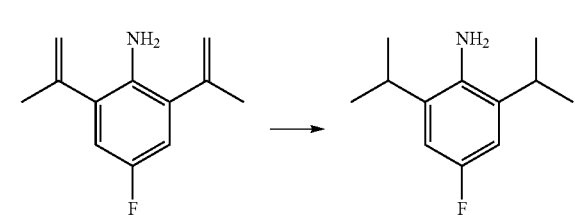

To a solution of 4-fluoro-2,6-di(prop-1-en-2-yl)aniline (8 g, 1 eq) in MeOH (150 mL) was added Pd/C (624 mg, 10 wt % loading on activated carbon). The reaction mixture was degassed and purged with H$_2$ (20 psi). The reaction mixture was stirred at 25° C. for 12 hours under H$_2$ (20 psi), and then filtered. The filtrate was concentrated in vacuo. The residue was purified by column chromatography (SiO$_2$, only eluting with petroleum ether) to give the title compound (4 g, 63% yield, 100% purity on LCMS) as a colourless oil.

1H NMR (400 MHz, CDCl$_3$) δ 6.76 (d, 2H), 3.56 (s, 2H), 2.99-2.89 (m, 2H) and 1.26 (d, 12H).

LCMS: m/z 196.2 (M+H)$^+$ (ES$^+$).

Step C: 2-Bromo-5-fluoro-1,3-diisopropylbenzene

To a solution of 4-fluoro-2,6-diisopropylaniline (3.7 g, 18.95 mmol, 1 eq) in MeCN (180 mL) was added CuBr (4.08 g, 1.5 eq). Then tert-butyl nitrite (2.93 g, 1.5 eq) was added dropwise at 0° C. The resulting mixture was stirred at 60° C. for 1.5 hours, and then concentrated in vacuo. The residue was purified by column chromatography (SiO$_2$, only eluting with petroleum ether) to give the title compound (2.02 g, 41%) as a white solid.

$^1$H NMR (400 MHz, CDCl$_3$) δ 6.85 (d, 2H), 3.55-3.48 (m, 2H) and 1.24 (d, 12H).

Step D: (2-(tert-Butoxy)-2-oxoethyl) zinc (II) bromide

A mixture of zinc (80 g) in HCl (1 M, 308 mL) was stirred at 25° C. for 30 minutes. Then the mixture was filtered and the filter cake was dried in vacuo. To a mixture of the above Zn (55 g, 841.11 mmol, 2.98 eq) in THF (550 mL) was added TMSCl (3.06 g, 28.20 mmol, 0.1 eq) and 1,2-dibromoethane (5.30 g, 28.20 mmol, 0.1 eq) at 20° C. under N$_2$ atmosphere. Then tert-butyl 2-bromoacetate (55 g, 281.97 mmol, 1 eq) was added at 50° C. under N$_2$ atmosphere. The reaction mixture was stirred at 50° C. for 2 hours. Then the reaction mixture (theory amount: 0.5 M, 550 mL, in THF solution) was cooled and used into the next step without further purification.

Step E: tert-Butyl 2-(4-fluoro-2,6-diisopropylphenyl)acetate

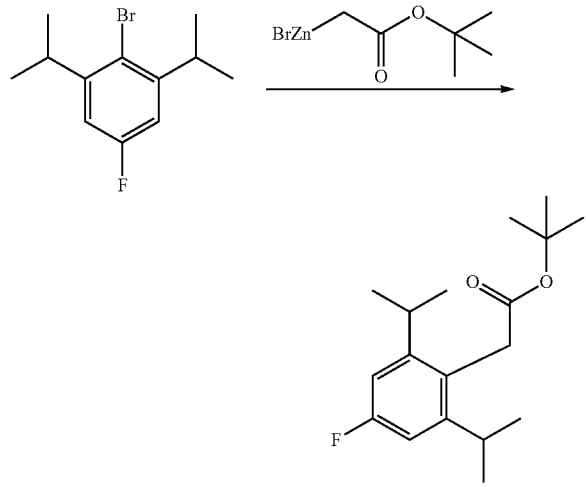

A solution of 2-bromo-5-fluoro-1,3-diisopropylbenzene (16 g, 61.74 mmol, 1 eq) in THF (100 mL) was cooled to 0° C. Then Pd$_2$(dba)$_3$ (2.83 g, 3.09 mmol, 0.05 eq), Xphos (2.94 g, 6.17 mmol, 0.1 eq) and (2-(tert-butoxy)-2-oxoethyl) zinc (II) bromide (0.5 M, 246.95 mL, in THF solution, 2 eq) were added. The reaction mixture was stirred at 70° C. for 12 hours, and then concentrated in vacuo. The residue was purified by column chromatography (SiO$_2$, petroleum ether: ethyl acetate, 100:0 to 10:1) to give the title compound (12 g, 59% yield, 90% purity on $^1$H NMR) as a red oil.

$^1$H NMR (400 MHz, CDCl$_3$) δ 6.83 (d, 2H), 3.66 (s, 2H), 3.21-3.14 (m, 2H), 1.43 (s, 9H) and 1.21 (d, 12H).

Step F: 2-(4-Fluoro-2,6-diisopropylphenyl)acetic acid

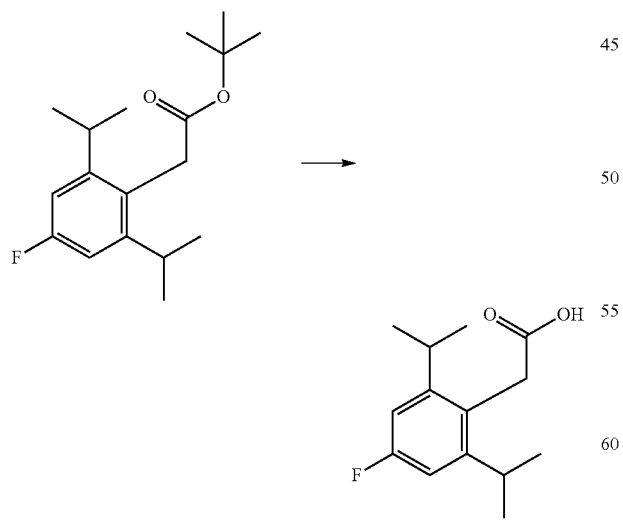

To a solution of tert-butyl 2-(4-fluoro-2,6-diisopropylphenyl)acetate (12 g, 40.76 mmol, 1 eq) in DCM (120 mL) was added TFA (184.80 g, 39.76 eq). The reaction mixture was stirred at 25° C. for 3 hours. Most of the solvents were evaporated under reduced pressure. The residue was diluted with H$_2$O (300 mL) and the mixture was adjusted to pH 10 with 2M aqueous NaOH solution. The mixture was washed with EtOAc (3×500 mL) and the organic phases were discarded. Then the aqueous layer was adjusted to pH 3 with 1M aqueous HCl solution and extracted with EtOAc (3×500 mL). The combined organic layers were washed with brine (2×200 mL), dried over Na$_2$SO$_4$, filtered and concentrated under reduced pressure to give the title compound (8 g, 82%) as a yellow solid.

$^1$H NMR (400 MHz, DMSO-d$_6$) δ 12.24 (br s, 1H), 6.91 (d, 2H), 3.78 (s, 2H), 3.16-3.06 (m, 2H) and 1.18 (d, 12H).

Intermediate P1: 1-Isopropyl-5-(3-methoxyoxetan-3-yl)-1H-pyrazole-3-sulfonamide

Step A: 1-Isopropyl-3-nitro-1H-pyrazole

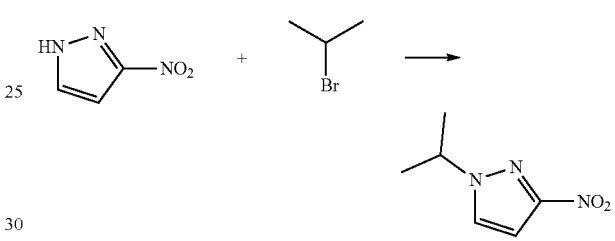

To a mixture of 3-nitro-1H-pyrazole (30 g, 265.31 mmol, 1 eq) in DMF (300 mL) was added NaH (11.14 g, 278.58 mmol, 60% purity in mineral oil, 1.05 eq) in portions at 0° C. Then the reaction mixture was stirred at 0° C. for 0.5 hour. 2-Bromopropane (39.16 g, 318.37 mmol, 1.2 eq) was added and the resulting mixture was warmed to 25° C. for 12 hours. The reaction mixture was quenched with water (500 mL) and extracted with EtOAc (3×300 mL). The combined organic layers were washed with brine (100 mL), dried over anhydrous Na$_2$SO$_4$, filtered and concentrated in vacuo. The residue was purified by chromatography (SiO$_2$, petroleum ether:ethyl acetate, 50:1 to 2:1) to give the title compound (29.2 g, 71%) as a yellow oil.

$^1$H NMR (400 MHz, CDCl$_3$) δ 7.49 (d, 1H), 6.90 (d, 1H), 4.63-4.56 (m, 1H) and 1.58 (d, 6H).

Step B: 1-Isopropyl-1H-pyrazol-3-amine

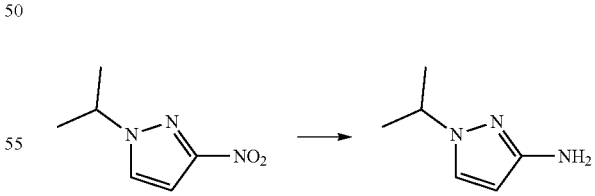

To a solution of 1-isopropyl-3-nitro-1H-pyrazole (29.2 g, 188.20 mmol, 1 eq) in MeOH (400 mL) was added Pd/C (3 g, 10 wt % loading on activated carbon) under N$_2$. The suspension was degassed in vacuo and purged with H$_2$ several times. The reaction mixture was stirred at 25° C. for 2 hours under H$_2$ (30 psi). The reaction mixture was filtered and the filtrate was concentrated in vacuo to give the title compound (15.81 g, 66% yield, 98.2% purity on LCMS) as a brown oil.

¹H NMR (400 MHz, CDCl₃) δ 7.15 (d, 1H), 5.55 (d, 1H), 4.30-4.20 (m, 1H), 3.61 (s, 2H) and 1.43 (d, 6H).
LCMS: m/z 126.2 (M+H)⁺ (ES⁺).

Step C: 1-Isopropyl-1H-pyrazole-3-sulfonyl chloride

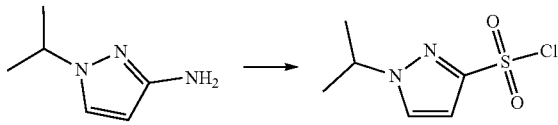

To a solution of 1-isopropyl-1H-pyrazol-3-amine (15.8 g, 126.23 mmol, 1 eq) in MeCN (600 mL) at 0° C. was added a solution of HCl (116.57 mL, 11.08 eq, 36 wt % in aqueous solution) in H₂ (50 mL). Then an aqueous solution of NaNO₂ (10.45 g, 151-47 mmol, 1.2 eq) in H₂O (50 mL) was added slowly. The resulting mixture was stirred at 0° C. for 0.75 hour. AcOH (50 mL), CuCl (625 mg, 6.31 mmol, 0.05 eq) and CuCl₂ (8.49 g, 63.11 mmol, 0.5 eq) were added. Then SO₂ gas (15 psi) was bubbled into the mixture at 0° C. for 0.25 hour. The reaction mixture was stirred at 0° C. for 1 hour, and then poured into ice water (500 mL) and extracted with DCM (2×700 mL). The combined organic layers were washed with brine (2×700 mL), dried over anhydrous Na₂SO₄, filtered and concentrated in vacuo. The residue was purified by chromatography (SiO₂, petroleum ether:ethyl acetate, 1:0 to 10:1) to give the title compound (18.36 g, 70%) as a colourless oil.
¹H NMR (400 MHz, CDCl₃) δ 7.56 (d, 1H), 6.88 (d, 1H), 4.70-4.60 (m, 1H) and 1.59 (d, 6H).

Step D: 1-Isopropyl-N,N-bis(4-methoxybenzyl)-1H-pyrazole-3-sulfonamide

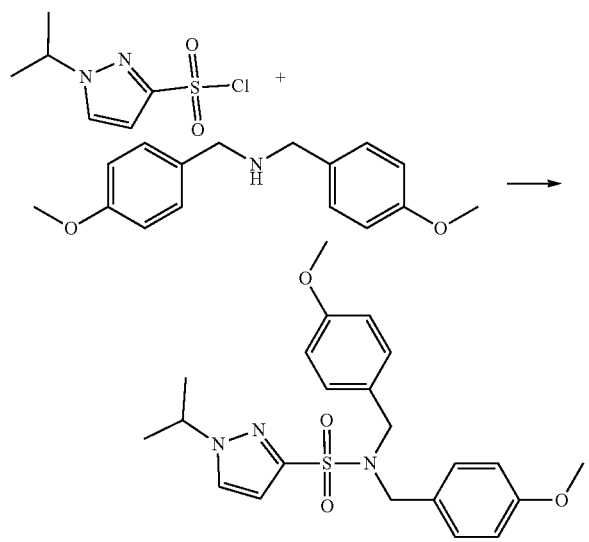

To a mixture of 1-isopropyl-1H-pyrazole-3-sulfonyl chloride (17.3 g, 82.91 mmol, 1 eq) and TEA (10.91 g, 107.78 mmol, 1.3 eq) in THF (200 mL) was added bis(4-methoxybenzyl)amine (14.93 g, 58.04 mmol, 0.7 eq). The reaction mixture was stirred at 20° C. for 3 hours, and then poured into water (500 mL) and extracted with DCM (2×500 mL). The combined organic layers were washed with brine (2×500 mL), dried over anhydrous Na₂SO₄ filtered and concentrated in vacuo. The residue was purified by column chromatography (SiO₂, petroleum ether:ethyl acetate, 20:1 to 4:1) to give the title compound (21.13 g, 59% yield, 100% purity on LCMS) as a colourless oil.
¹H NMR (400 MHz, CDCl₃) δ 7.46 (d, 1H), 7.09-7.04 (m, 4H), 6.80-6.74 (m, 4H), 6.65 (d, 1H), 4.62-4.54 (m, 1H), 4.32 (s, 4H), 3.79 (s, 6H) and 1.53 (d, 6H).
LCMS: m/z 452.2 (M+Na)⁺ (ES⁺).

Step E: 5-(3-Hydroxyoxetan-3-yl)-1-isopropyl-N,N-bis(4-methoxybenzyl)-1H-pyrazole-3-sulfonamide

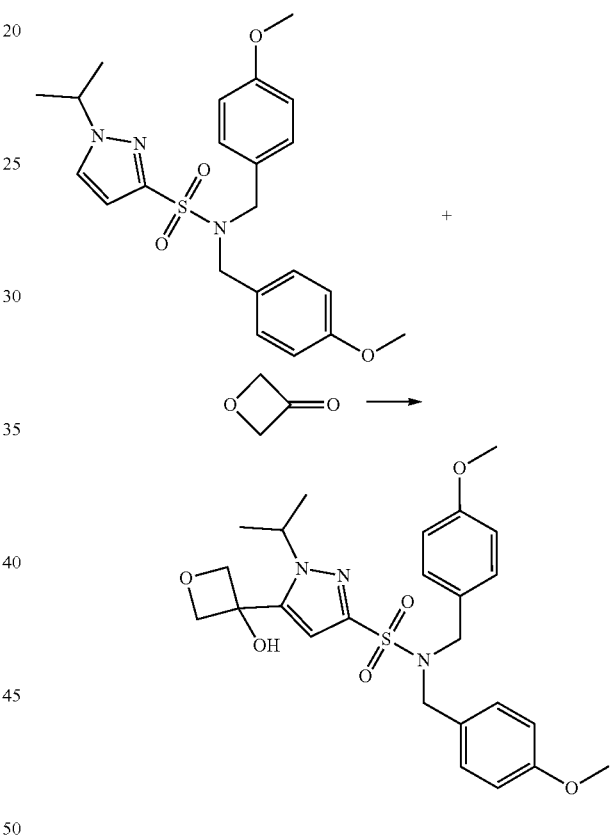

To a solution of 1-isopropyl-N,N-bis(4-methoxybenzyl)-1H-pyrazole-3-sulfonamide (12 g, 27.94 mmol, 1 eq) in THF (200 mL) was added dropwise n-BuLi (2.5 M, 12.07 mL, in THF, 1.08 eq) at −78° C. Then the reaction mixture was stirred at −78° C. for 1 hour. A solution of oxetan-3-one (2.07 g, 28.78 mmol, 1.03 eq) in THF (50 mL) was added and the resulting mixture was stirred at −78° C. for 1 hour. The reaction mixture was quenched with saturated aqueous NH₄Cl solution (10 mL), poured into water (500 mL) and extracted with ethyl acetate (2×500 mL). The combined organic layers were washed with brine (2×500 mL), dried over anhydrous Na₂SO₄, filtered and concentrated in vacuo. The residue was purified by chromatography (SiO₂, petroleum ether:ethyl acetate, 10:1 to 2:1) to give the title compound (5-11 g, 35% yield, 96.7% purity on LCMS) as a white solid.

¹H NMR (400 MHz, DMSO-d₆) δ 7.05 (d, 4H), 6.88 (s, 1H), 6.84-6.80 (m, 4H), 6.79 (s, 1H), 4.88 (d, 2H), 4.77 (d, 2H), 4.46-4.38 (m, 1H), 4.23 (s, 4H), 3.72 (s, 6H) and 1.36 (d, 6H).

LCMS: m/z 502.3 (M+H)⁺ (ES⁺).

Step F: 1-Isopropyl-N,N-bis(4-methoxybenzyl)-5-(3-methoxyoxetan-3-yl)-1H-pyrazole-3-sulfonamide

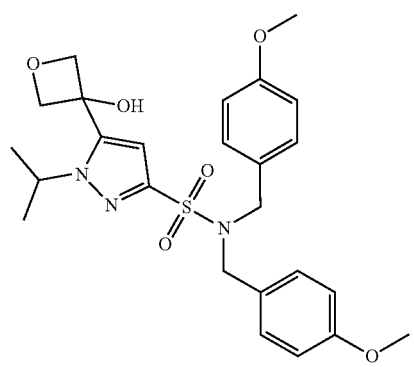

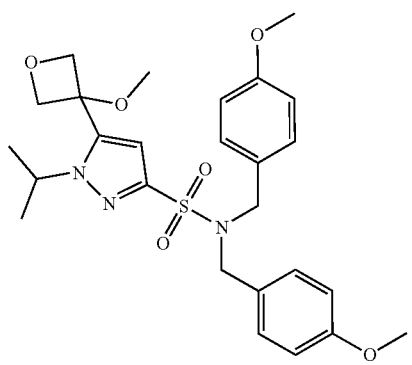

To a solution of 5-(3-hydroxyoxetan-3-yl)-1-isopropyl-N,N-bis(4-methoxybenzyl)-1H-pyrazole-3-sulfonamide (9.6 g, 19.14 mmol, 1 eq) in DMF (150 mL) was added portionwise NaH (919 mg, 22.97 mmol, 60 wt % in mineral oil, 1.2 eq) at 0° C. The reaction mixture was stirred at 0° C. for 0.5 hour. Then MeI (10.87 g, 76.56 mmol, 4 eq) was added. The reaction mixture was stirred at 0° C. for 13.5 hours, and then warmed to 20° C. The reaction mixture was quenched with saturated aqueous NH₄Cl solution (10 mL) slowly, poured into water (800 mL) and extracted with ethyl acetate (2×500 mL). The combined organic layers were washed with brine (3×500 mL), dried over anhydrous Na₂SO₄, filtered and concentrated in vacuo to give the title compound (9.87 g, 94% yield, 94.3% purity on LCMS) as a white solid.

¹H NMR (400 MHz, CDCl₃) δ 7.14-7.11 (m, 4H), 6.81-6.77 (m, 4H), 6.60 (s, 1H), 4.91 (d, 2H), 4.80 (d, 2H), 4.36 (s, 4H), 4.32-4.25 (m, 1H), 3.79 (s, 6H), 3.05 (s, 3H) and 1.43 (d, 6H).

LCMS: m/z 516.3 (M+H)⁺ (ES⁺).

Step G: 1-Isopropyl-5-(3-methoxyoxetan-3-yl)-1H-pyrazole-3-sulfonamide

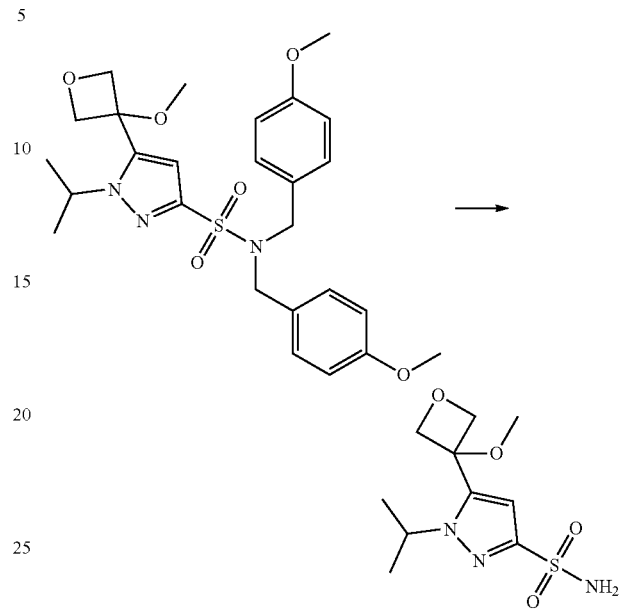

A solution of 1-isopropyl-N,N-bis(4-methoxybenzyl)-5-(3-methoxyoxetan-3-yl)-1H-pyrazole-3-sulfonamide (9.8 g, 19.01 mmol, 1 eq) in TFA (40 mL) and DCM (40 mL) was stirred at 16° C. for 20 hours. Then the reaction mixture was concentrated in vacuo. The residue was redissolved in THF (80 mL). Hexane (200 mL) was added to the mixture and some solid was precipitated. The colourless precipitate was collected by filtration, washing with hexane (100 ml) and dried in vacuo to give the title compound (3.5 g, 63% yield, 93.7% purity on LCMS) as a light yellow solid.

¹H NMR (400 MHz, DMSO-d₆) δ 7.46 (s, 2H), 6.86 (s, 1H), 4.86-4.82 (m, 4H), 4.30-4.20 (m, 1H), 3.00 (s, 3H) and 1.37 (d, 6H).

LCMS: m/z 276.1 (M+H)⁺ (ES⁺).

Intermediate P2: (R)-1-(2-Hydroxypropyl)-1H-pyrazole-3-sulfonamide

Step A: Lithium 1-(tetrahydro-2H-pyran-2-yl)-1H-pyrazole-5-sulfinate

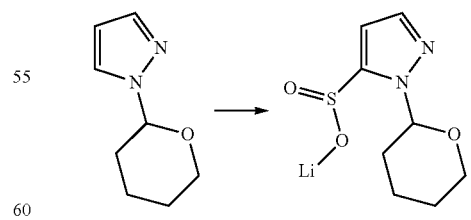

To a solution of 1-(tetrahydro-2H-pyran-2-yl)-1H-pyrazole (100 g, 657.06 mmol, 1 eq) in THF (1.38 L) was added n-BuLi (2.5 M, 276 mL, in THF, 1.05 eq) slowly while keeping the temperature at −70° C. The reaction mixture was stirred for 1.5 hours. Then SO₂ (15 psi) was bubbled into the mixture for 15 minutes. After the reaction mixture was heated to 25° C., a solid was formed. The reaction mixture was concentrated in vacuo. The residue was triturated with tert-butyl methyl ether (400 mL) and the mixture was filtered. The filter cake was washed with tert-butyl methyl ether (50 mL), n-hexane (50 mL) and dried to afford the title compound (142 g, crude) as a white solid.

$^1$H NMR (400 MHz, DMSO-d$_6$) δ 7.28 (d, 1H), 6.16 (d, 1H), 5.97 (dd, 1H), 3.92-3.87 (m, 1H), 3.61-3.53 (m, 1H), 2.25-2.18 (m, 1H), 1.98-1.93 (m, 1H), 1.78-1.74 (m, 1H) and 1.52-1.49 (m, 3H).

LCMS: m/z 215 (M-Li)$^-$ (ES$^-$).

Step B: 1-(Tetrahydro-2H-pyran-2-yl)-1H-pyrazole-5-sulfonyl chloride

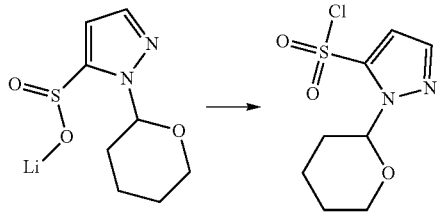

To a suspension of lithium 1-(tetrahydro-2H-pyran-2-yl)-1H-pyrazole-5-sulfinate (20 g, 90.01 mmol, 1 eq) in DCM (250 mL) was added NCS (12.02 g, 90.01 mmol, 1 eq) while cooling in an ice bath. The reaction mixture was stirred at 0° C. for 2 hours. Then the reaction mixture was quenched with water (100 mL) and partitioned between DCM (300 mL) and water (200 mL). The organic layer was washed with water (200 mL), dried over anhydrous magnesium sulfate, filtered and concentrated in vacuo to give the title compound (15.8 g, 63.02 mmol, 70%) as a yellow oil, which was used directly in the next step.

Step C: N,N-bis(4-Methoxybenzyl)-1-(tetrahydro-2H-pyran-2-yl)-1H-pyrazole-5-sulfonamide

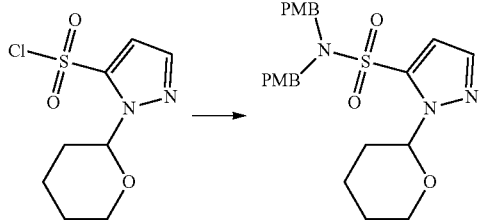

To a mixture of bis(4-methoxybenzyl)amine (16.01 g, 62.23 mmol, 1.04 eq) and TEA (19.33 g, 190.99 mmol, 3.19 eq) in DCM (300 mL) was added a solution of 1-(tetrahydro-2H-pyran-2-yl)-1H-pyrazole-5-sulfonyl chloride (15 g, 59.83 mmol, 1 eq) in DCM (50 mL) at 0° C. The reaction mixture was stirred at 0° C. for 1 hour and then quenched with water (250 mL). The organic layer was washed with water (250 mL), 1M aqueous HCl solution (2×250 mL), water (250 mL), and then dried over anhydrous MgSO$_4$, filtered, and concentrated in vacuo to give the title compound (25.5 g, 83% yield, 92% purity on LCMS) as a brown oil.

LCMS: m/z 494 (M+Na)$^+$ (ES$^+$).

Step D: N,N-bis(4-Methoxybenzyl)-1H-pyrazole-5-sulfonamide

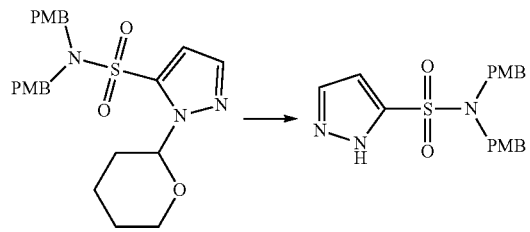

To a solution of N,N-bis(4-methoxybenzyl)-1-(tetrahydro-2H-pyran-2-yl)-1H-pyrazole-5-sulfonamide (25 g, 53.01 mmol, 1 eq) in THF (183 mL) and MeOH (37 mL) was added a 1M aqueous HCl solution (18.29 mL). The reaction mixture was stirred at 25° C. for 1 hour. Then the reaction mixture was concentrated in vacuo and the residue was partitioned between DCM (200 mL) and H$_2$O (100 mL). The organic layer was washed with brine (100 mL), dried over anhydrous MgSO$_4$, filtered and concentrated in vacuo. The residue was triturated with tert-butyl methyl ether (100 mL), filtered and dried to give the title compound (12.2 g, 8% yield, 97% purity on LCMS) as a white solid.

$^1$H NMR (400 MHz, CDCl$_3$) δ 13.82-13.70 (br s, 1H), 7.92 (d, 1H), 7.07-7.01 (m, 4H), 6.78-6.75 (m, 4H), 6.61 (d, 1H), 4.34 (s, 4H) and 3.80 (s, 6H).

LCMS: m/z 410 (M+Na)$^+$ (ES$^+$).

Step E: (R)-1-(2-Hydroxypropyl)-N,N-bis(4-methoxybenzyl)-1H-pyrazole-3-sulfonamide

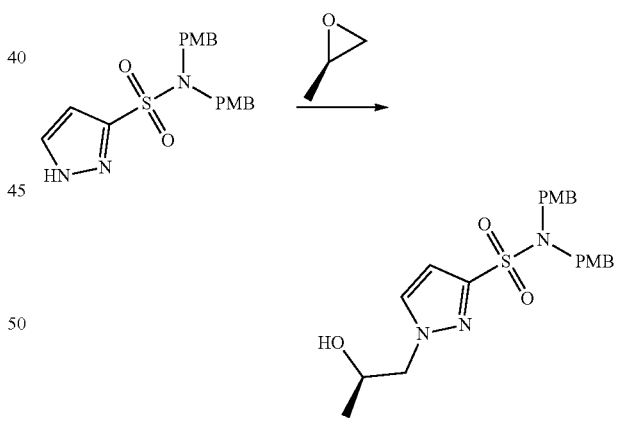

To a mixture of N,N-bis(4-methoxybenzyl)-1H-pyrazole-3-sulfonamide (20 g, 51.62 mmol, 1 eq) and (R)-2-methyloxirane (17.99 g, 309.72 mmol, 6 eq) in MeCN (150 mL) was added K$_2$CO$_3$ (14.27 g, 103.24 mmol, 2 eq). The reaction mixture was stirred at 50° C. for 20 hours, and then poured into water (500 mL) and extracted with ethyl acetate (2×500 mL). The combined organic layers were washed with brine (2×500 mL), dried over anhydrous Na$_2$SO$_4$, filtered and concentrated in vacuo. The residue was purified by column chromatography (SiO$_2$, petroleum ether:ethyl acetate, 10:1 to 2:1) to give the title compound (12.77 g, 55% yield, 99.5% purity on LCMS) as a light yellow oil.

¹H NMR (400 MHz, DMSO-d₆) δ 7.90 (d, 1H), 7.02-6.99 (m, 4H), 6.82-6.80 (m, 4H), 6.70 (d, 1H), 5.02 (d, 1H), 4.18 (s, 4H), 4.14-4.00 (m, 3H), 3.71 (s, 6H) and 1.07-1.06 (d, 3H).

LCMS: m/z 446.2 (M+H)⁺ (ES⁺).

Step F: (R)-1-(2-Hydroxypropyl)-1H-pyrazole-3-sulfonamide

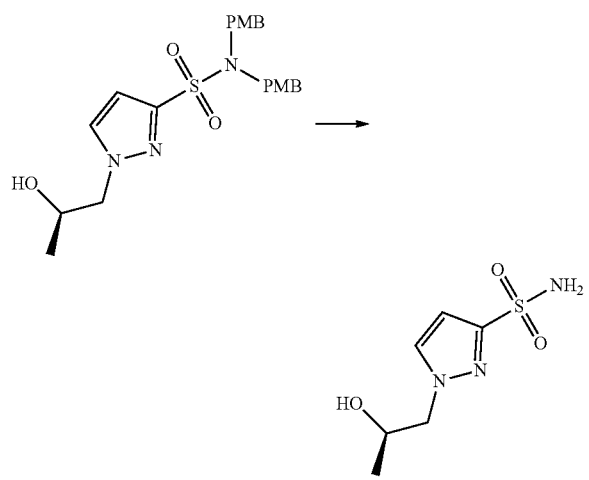

A mixture of (R)-1-(2-hydroxypropyl)-N,N-bis(4-methoxybenzyl)-1H-pyrazole-3-sulfonamide (5.4 g, 12.12 mmol, 1 eq) in TFA (16 mL) and DCM (32 mL) was stirred at 30° C. for 16 hours. Then the reaction mixture was poured into MeOH (100 mL) and the resulting mixture was stirred for 30 minutes. The mixture was filtered and the filtrate was concentrated in vacuo. The residue was dissolved in MeOH (100 mL) and the resulting mixture was adjusted to pH 8 by treating with resin (Amberlyst® A-21, ion exchange resin). The mixture was filtered and the filtrate was concentrated in vacuo to give the title compound (2.38 g, crude) as a light yellow oil.

¹H NMR (400 MHz, DMSO-d₆) δ 7.80-7.79 (d, 1H), 7.36 (s, 2H), 6.56-6.55 (d, 1H), 4.97 (d, 1H), 4.10-4.03 (m, 2H), 4.02-3.93 (m, 1H) and 1.06-1.05 (d, 3H).

LCMS: m/z 228.1 (M+Na)⁺ (ES⁺).

SYNTHESIS OF EXAMPLES

Example 1: 2-(1,2,3,5,6,7-Hexahydro-s-indacen-4-yl)-N-((1-isopropyl-5-(3-methoxyoxetan-3-yl)-1H-pyrazol-3-yl)sulfonyl)acetamide

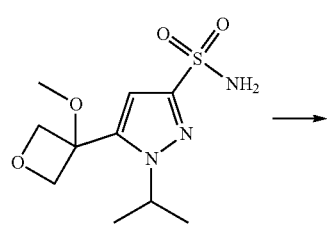

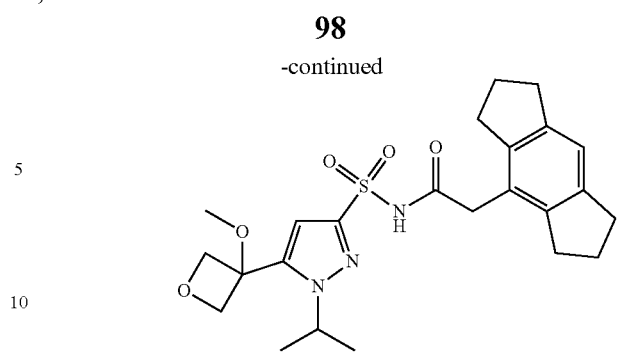

Et₃N (0.67 mL, 4.80 mmol) and 1-isopropyl-5-(3-methoxyoxetan-3-yl)-1H-pyrazole-3-sulfonamide (Intermediate P1) (84 mg, 0.31 mmol) were added to a solution of 2-(1,2,3,5,6,7-hexahydro-s-indacen-4-yl)acetyl chloride (60 mg, 0.26 mmol) in DCM (5 mL). The mixture was stirred for 48 hours at room temperature and then concentrated. Purification by column chromatography (SiO₂, 0-6% MeOH in DCM) afforded the title compound.

The product was recrystallized from a heptane/DCM mixture, washed with pentane and dried in vacuo to afford the title compound (48 mg, 39%) as a white solid.

¹H NMR (300 MHz, CDCl₃) δ 7.91 (s, 1H), 7.09 (s, 1H), 6.96 (s, 1H), 4.96-4.81 (m, 4H), 4.34 (m, 1H), 3.63 (s, 2H), 3.06 (s, 3H), 2.90 (t, 4H), 2.72 (t, 4H), 2.08 (m, 4H), 1.45 (d, 6H).

LCMS: m/z 474 (M+H)⁺ (ES⁺); 472 (M–H)⁻ (ES⁻).

Example 2: 2-(5-(2-Cyanopyridin-4-yl)-2,3-dihydro-1H-inden-4-yl)-N-((1-isopropyl-5-(3-methoxyoxetan-3-yl)-1H-pyrazol-3-yl)sulfonyl)acetamide, potassium Salt

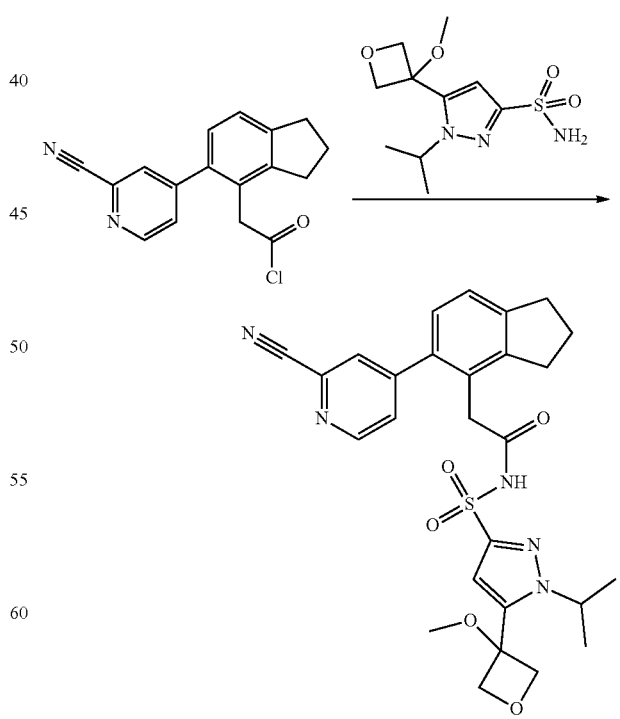

To a solution of 1-isopropyl-5-(3-methoxyoxetan-3-yl)-1H-pyrazole-3-sulfonamide (Intermediate P1) (49 mg, 0.18 mmol, 1.8 eq) in anhydrous tetrahydrofuran (2 mL) was added potassium tert-butoxide (20 mg, 0.18 mmol, 1.8 eq). The suspension was cooled in an ice bath. A solution of 2-(5-(2-cyanopyridin-4-yl)-2,3-dihydro-H-inden-4-yl)acetyl chloride (Intermediate A1) (30 mg, 0.10 mmol, 1 eq) in anhydrous tetrahydrofuran (2 mL) was added dropwise. After complete addition, the cooling bath was removed and the reaction mixture was allowed to stir at room temperature. After 2 hours, the reaction mixture was concentrated in vacuo. The residue was dissolved in DMSO (0.5 mL) and submitted for purification by reversed phase column chromatography (see "Experimental Methods", "Purification Method 1") to afford the title compound (6.0 mg, 0.011 mmol, 11%) as a white solid.

$^1$H NMR (CD$_3$OD) δ 8.66 (d, 1H), 7.85 (s, 1H), 7.62 (dd, 1H), 7.21 (d, 1H), 7.04 (d, 1H), 6.90 (s, 1H), 4.84 (d, 4H), 4.41-4.26 (m, 1H), 3.52 (s, 2H), 3.05 (s, 3H), 2.94 (t, 2H), 2.79 (t, 2H), 2.13-1.99 (m, 2H), 1.42 (dd, 6H).

LCMS: m/z 536 (M+H)$^+$ (ES$^+$).

Example 3: N-((1-Cyclopropyl-5-(3-methoxyoxetan-3-yl)-1H-pyrazol-3-yl)sulfonyl)-2-(1,2,3,5,6,7-hexahydro-s-indacen-4-yl)acetamide

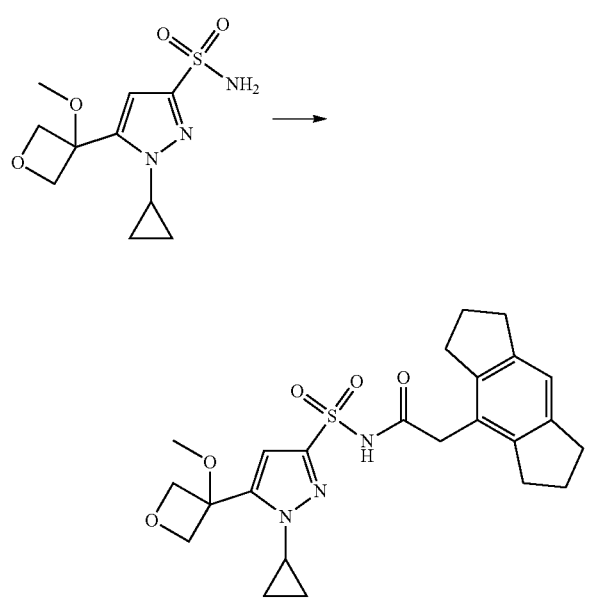

Prepared as described for 2-(1,2,3,5,6,7-hexahydro-s-indacen-4-yl)-N-((1-isopropyl-5-(3-methoxyoxetan-3-yl)-1H-pyrazol-3-yl)sulfonyl)acetamide (Example 1) using 1-cyclopropyl-5-(3-methoxyoxetan-3-yl)-1H-pyrazole-3-sulfonamide (78 mg, 0.28 mmol) and 2-(1,2,3,5,6,7-hexahydro-s-indacen-4-yl)acetyl chloride (80 mg, 0.34 mmol) to afford the title compound (71 mg, 53%) as a white solid.

$^1$H NMR (300 MHz, CDCl$_3$) δ 7.82 (s, 1H), 7.09 (s, 1H), 7.00 (s, 1H), 4.93 (s, 4H), 3.67-3.54 (m, 3H), 3.09 (s, 3H), 2.91 (t, 4H), 2.71 (t, 4H), 2.09 (m, 4H), 1.28 (m, 2H), 1.02 (m, 2H).

LCMS: m/z 472 (M+H)$^+$ (ES$^+$); 470 (M−H)$^-$ (ES$^-$).

Example 4: 2-(1,2,3,5,6,7-Hexahydro-s-indacen-4-yl)-N-((1-(2-methoxy-2-methylpropyl)-1H-pyrazol-3-yl)sulfonyl)acetamide

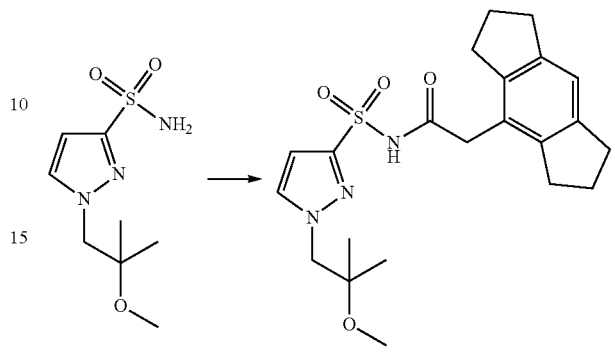

Triethylamine (0.67 mL, 4.80 mmol) and 1-(2-methoxy-2-methylpropyl)-1H-pyrazole-3-sulfonamide (60 mg, 0.26 mmol) were added to a solution of 2-(1,2,3,5,6,7-hexahydro-s-indacen-4-yl)acetyl chloride (60 mg, 0.26 mmol) in DCM (5 mL). The mixture was stirred for 48 hours at room temperature and then concentrated. Purification by column chromatography (SiO$_2$, 0-6% MeOH in DCM) afforded the title compound (67 mg, 60%) as a white solid.

$^1$H NMR (300 MHz, CDCl$_3$) δ 7.83 (s, 1H), 7.59 (d, 1H), 7.07 (s, 1H), 6.93 (d, 1H), 4.16 (s, 2H), 3.60 (s, 2H), 3.22 (s, 3H), 2.89 (t, 4H), 2.71 (t, 4H), 2.07 (m, 4H), 1.11 (s, 6H).

LCMS: m/z 432 (M+H)$^+$ (ES$^+$); 430 (M−H)$^-$ (ES$^-$).

Example 5: 2-(4-Fluoro-2,6-diisopropylphenyl)-N-((1-isopropyl-5-(3-methoxyoxetan-3-yl)-1H-pyrazol-3-yl)sulfonyl)acetamide

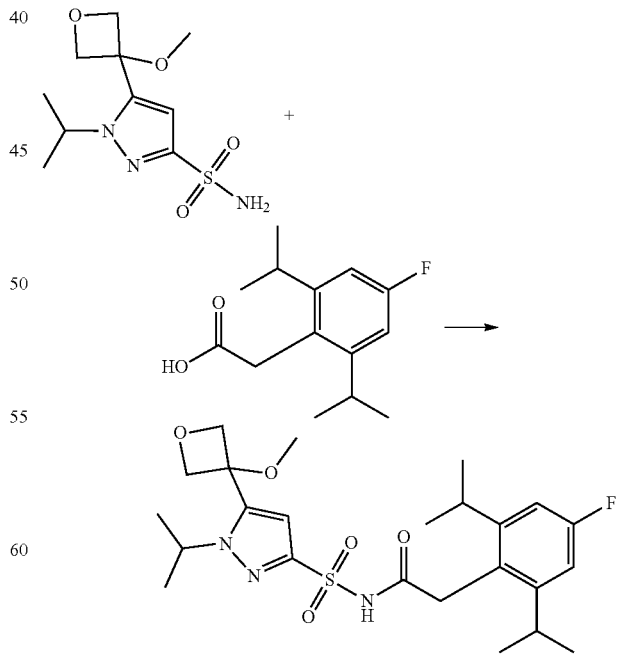

To a mixture of 1-isopropyl-5-(3-methoxyoxetan-3-yl)-1H-pyrazole-3-sulfonamide (Intermediate P1) (69 mg, 251.79 µmol, 1 eq) and 2-(4-fluoro-2,6-diisopropylphenyl) acetic acid (Intermediate A2) (60 mg, 251.79 µmol, 1 eq) in DMF (2 mL) were added EDC (97 mg, 503.57 µmol, 2 eq) and DMAP (62 mg, 503.57 µmol, 2 eq) in one portion at 16° C. The reaction mixture was stirred at 16° C. for 1 hour, and then poured into saturated aqueous citric acid solution (10 mL) and extracted with DCM (2×10 mL). The combined organic layers were washed with brine (2×10 mL), dried over anhydrous $Na_2SO_4$, filtered and concentrated in vacuo. The residue was purified by prep-HPLC (Column: Waters Xbridge C18, 150 mm*25 mm*5 µm; mobile phase [A: water (0.05% ammonium hydroxide v/v); B: MeCN]; B %: 16%-36%, 10 min) to give the title compound (34 mg, 27% yield, 100% purity on LCMS) as a white solid.

$^1$H NMR (400 MHz, DMSO-$d_6$) δ 6.93 (s, 1H), 6.85 (d, 2H), 4.81-4.77 (m, 4H), 4.26-4.19 (m, 1H), 3.69 (s, 2H), 2.97-2.93 (m, 5H), 1.34 (d, 6H) and 1.04 (d, 12H). LCMS: m/z 496.2 (M+H)$^+$ (ES$^+$).

Example 6: (R)-2-(4-Fluoro-2,6-diisopropylphenyl)-N-((1-(2-hydroxypropyl)-1H-pyrazol-3-yl)sulfonyl) acetamide Step A: (R)-1-(2-((tert-Butyldimethylsilyl)oxy)propyl)-1H-pyrazole-3-sulfonamide

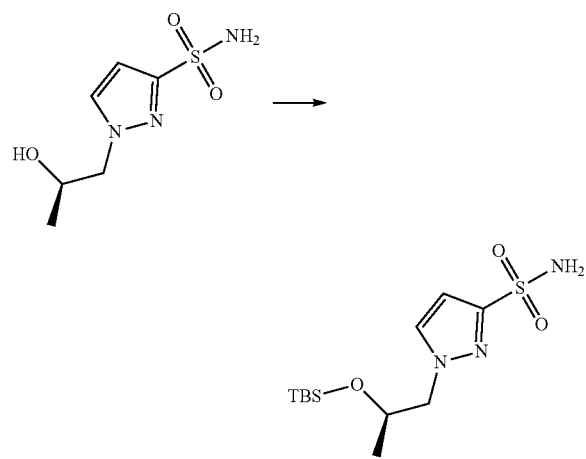

To a solution of (R)-1-(2-hydroxypropyl)-1H-pyrazole-3-sulfonamide (Intermediate P2) (200 mg, 974.50 µmol, 1 eq) and imidazole (199 mg, 2.92 mmol, 3 eq) in DMF (2 mL) was added TBSCl (154 mg, 1.02 mmol, 1.05 eq) at 0° C. The mixture was stirred at 20° C. for 2 hours, and then poured into water (10 mL) and extracted with ethyl acetate (3×10 mL). The combined organic layers were washed with brine (10 mL), dried over anhydrous sodium sulfate, filtered and concentrated in vacuo. The residue was purified by reversed phase flash chromatography (0.1% $NH_3·H_2O$-MeCN) to give the title compound (120 mg, 30% yield, 77.5% purity on LCMS) as a white solid.

$^1$H NMR (400 MHz, CDCl$_3$) δ 7.46 (d, 1H), 6.70 (d, 1H), 5.04 (s, 2H), 4.25-4.20 (m, 2H), 4.03-3.99 (m, 1H), 1.29 (d, 3H), 0.82 (s, 9H), -0.03 (s, 3H), -0.22 (s, 3H).

LCMS: m/z 320.1 (M+H)$^+$ (ES$^+$).

Step B: (R)—N-((1-(2-((tert-Butyldimethylsilyl)oxy)propyl)-1H-pyrazol-3-yl)sulfonyl)-2-(4-fluoro-2,6-diisopropylphenyl)acetamide

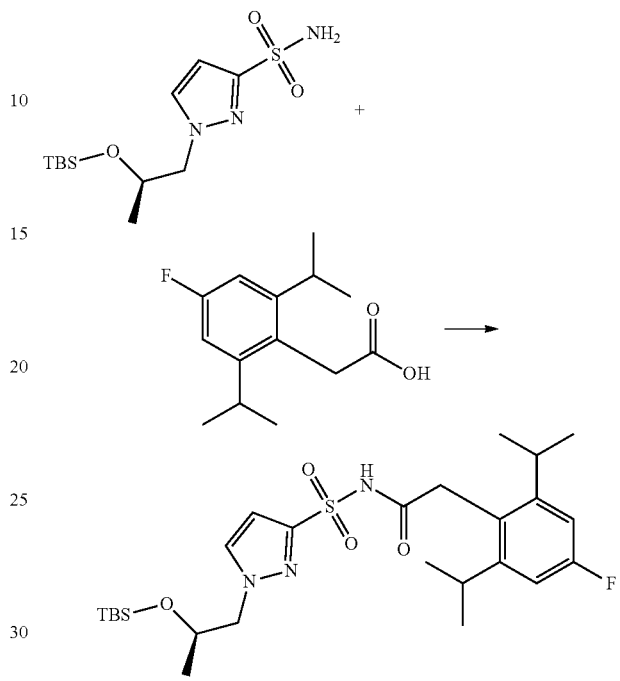

To a mixture of 2-(4-fluoro-2,6-diisopropylphenyl)acetic acid (Intermediate A2) (90 mg, 375.59 µmol, 1 eq), EDC (144 mg, 751.19 µmol, 2 eq) and DMAP (92 mg, 751.19 µmol, 2 eq) in DMF (2 mL) was added (R)-1-(2-((tert-butyldimethylsilyl)oxy)propyl)-1H-pyrazole-3-sulfonamide (120 mg, 375.59 µmol, 1 eq) at 20° C. The reaction mixture was stirred at 20° C. for 2 hours, and then poured into 0.5 M aqueous HCl solution (20 mL). The mixture was extracted with ethyl acetate (3×10 mL). The combined organic layers were washed with brine (3×10 mL), dried over anhydrous sodium sulfate, filtered and concentrated in vacuo to give the title compound (150 mg, crude) as a white solid.

$^1$H NMR (400 MHz, CDCl$_3$) δ 7.43 (d, 1H), 6.82 (d, 2H), 6.67 (d, 1H), 4.12-4.01 (m, 1H), 3.99-3.87 (m, 2H), 3.76 (s, 2H), 3.04-2.89 (m, 2H), 1.27-1.07 (m, 15H), 0.84 (s, 9H), -0.04 (s, 3H) and -0.18 (s, 3H).

LCMS: m/z 540.3 (M+H)$^+$ (ES$^+$).

Step C: (R)-2-(4-Fluoro-2,6-diisopropylphenyl)-N-((1-(2-hydroxypropyl)-1H-pyrazol-3-yl)sulfonyl) acetamide

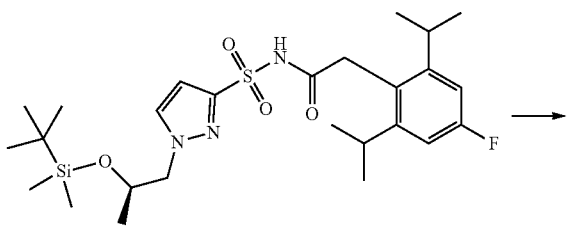

-continued

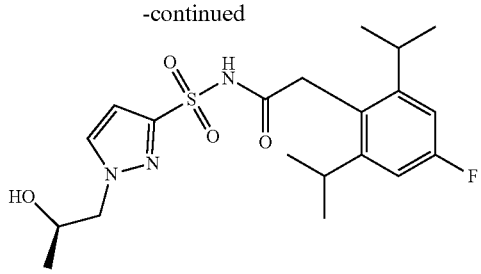

A solution of (R)—N-((1-(2-((tert-butyldimethylsilyl)oxy)propyl)-1H-pyrazol-3-yl)sulfonyl)-2-(4-fluoro-2,6-diisopropylphenyl)acetamide (150 mg, 277.89 μmol, 1 eq) in HCl/dioxane (5 mL, 4M) was stirred at 20° C. for 2 hours. The mixture was concentrated in vacuo. The residue was purified by prep-HPLC (Column: Phenomenex Synergi C18, 150 mm*25 mm*10 μm; mobile phase [A: water (0.225% formic acid); B: MeCN]; B %: 40%-70%, 2 min) to give the title compound (35.91 mg, 30% yield, 99.4% purity on LCMS) as a white solid.

$^1$H NMR (400 MHz, DMSO-$d_6$) δ 12.34 (br s, 1H), 7.83 (s, 1H), 6.87 (d, 2H), 6.69 (s, 1H), 5.00 (d, 2H), 4.12-4.05 (m, 2H), 3.98-3.92 (m, 1H), 3.74 (s, 2H), 2.92-2.88 (m, 2H) and 1.04-1.01 (m, 15H).

LCMS: m/z 426.1 (M+H)$^+$ (ES$^+$).

SFC: retention time: 0.770 min. ee value: 100%.

The compounds of examples 7-9 were synthesised by methods analogous to those outlined above.

TABLE 1

$^1$H NMR and MS data

| Ex | Structure and Name | 1H NMR spectrum | MS | MW |
|---|---|---|---|---|
| 7 | 2-(4-Fluoro-2-isopropyl-6-(2-methoxypyridin-4-yl)phenyl)-N-((1-(2-hydroxy-2-methylpropyl)-1H-pyrazol-4-yl)sulfonyl)acetamide, potassium salt | $^1$H NMR (300 MHz, Methanol-$d_4$) δ 8.04 (d, 2H), 7.77 (s, 1H), 7.02 (dd, 1H), 6.89 (dd, 1H), 6.80-6.70 (m, 2H), 4.08 (s, 2H), 3.90 (s, 3H), 3.42 (s, 2H), 3.08 (m, 1H), 1.20-1.09 (m, 12H). | m/z 505.2 (M + H)$^+$ (ES$^+$); 503.2 (M − H)$^−$ (ES$^−$). | 504.58 |
| 8 | 2-(4-Fluoro-2-isopropyl-6-(2-methoxypyridin-4-yl)phenyl)-N-((1-(1-methoxy-2-methylpropan-2-yl)-1H-pyrazol-3-yl)sulfonyl)acetamide, potassium salt | $^1$H NMR (300 MHz, Methanol-$d_4$) δ 8.05 (d, 1H), 7.70 (d, 1H), 7.02 (dd, 1H), 6.92 (dd, 1H), 6.80 (s, 1H), 6.72 (dd, 1H), 6.61 (d, 1H), 3.91 (s, 3H), 3.58 (s, 2H), 3.45 (s, 2H), 3.22 (s, 3H), 3.16-3.00 (m, 1H), 1.56 (s, 6H), 1.14 (d, 6H). | m/z 519.2 (M + H)$^+$ (ES$^+$); 517.2 (M − H)$^−$ (ES$^−$). | 518.60 |
| 9 | 2-(4-Fluoro-2-isopropyl-6-(2-methoxypyridin-4-yl)phenyl)-N-((1-(1-methoxy-2-methylpropan-2-yl)-1H-pyrazol-3-yl)sulfonyl)acetamide, potassium salt | $^1$H NMR (300 MHz, Methanol-$d_4$) δ 8.08 (d, 1H), 7.72 (d, 1H), 7.07-6.98 (m, 1H), 6.94 (d, 1H), 6.80 (s, 1H), 6.76-6.69 (m, 1H), 6.59 (d, 1H), 3.91 (s, 3H), 3.74 (s, 2H), 3.47 (s, 2H), 3.14-2.99 (m, 1H), 1.54 (s, 6H), 1.15 (d, 6H). | m/z 505.2 (M + H)$^+$ (ES$^+$); 503.2 (M − H)$^−$ (ES$^−$). | 504.58 |

Further compounds of the invention may be synthesised by methods analogous to those outlined above.

EXAMPLES—BIOLOGICAL STUDIES

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~$10^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C., 5% $CO_2$
4. Add 5 μl nigericin (Sigma #N7143) (FAC 5 μM) to all wells
5. Incubate for 1 hr at 37° C., 5% $CO_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% $CO_2$
8. Plates were read in an Envision reader at Ex 560 nm and Em 590 nm
9. $IC_{50}$ data is fitted to a non-linear regression equation (log inhibitor vs response-variable slope 4-parameters)

96-Well Plate Map

|   | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High = High
Low = Low
MCC950(10 uM) = Drug free control
Compound 8-point half-log dilution The results of the pyroptosis assay are summarised in Table 2 below as THP $IC_{50}$.

TABLE 2

NLRP3 inhibitory activity (≤5 μM = '++', ≤10 μM = '+').

| Example No | THP $IC_{50}$ |
|---|---|
| 1 | ++ |
| 2 | + |
| 3 | ++ |
| 4 | ++ |
| 5 | ++ |
| 6 | ++ |
| 7 | ++ |
| 8 | ++ |
| 9 | ++ |

As is evident from the results presented in Table 2, surprisingly in spite of the structural differences versus the prior art compounds, the compounds of the invention show high levels of NLRP3 inhibitory activity.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

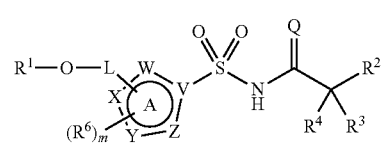

Formula (I)

or a pharmaceutically acceptable salt or solvate thereof, wherein:
ring A is monocyclic;
Q is selected from O or S;
V is selected from N or C, and W, X, Y and Z are each independently selected from N, O, NH or CH, wherein at least one of V, W, X, Y and Z is N or NH;

L is a saturated or unsaturated hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;

$R^1$ is hydrogen or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

optionally L and $R^1$ together with the oxygen atom to which they are attached may form a 3- to 12-membered saturated or unsaturated cyclic group, wherein the cyclic group may optionally be substituted;

$R^2$ is a cyclic group substituted at the α and α' positions, wherein $R^2$ may optionally be further substituted;

$R^3$ is hydrogen, halogen, —OH, —NH$_2$, —CN, —R$^5$, —OR$_5$, —NHR$_5$ or —N(R$^5$)$_2$;

$R^4$ is hydrogen, halogen, —OH, —NH$_2$, —CN, —R$^5$, —OR$_5$, —NHR$_5$ or —N(R$^5$)$_2$; or $R^3$ and $R^4$ together with the carbon atom to which they are attached may form a 3- to 7-membered saturated or unsaturated cyclic group, wherein the cyclic group may optionally be substituted;

each $R^5$ is independently an optionally substituted $C_1$-$C_4$ alkyl group;

each $R^6$ is independently halogen, —OH, —NO$_2$, —NH$_2$, —N$_3$, —SH, —SO$_2$H, —SO$_2$NH$_2$, or a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and m is 0, 1, 2 or 3;

provided that any atom of L or $R^1$ that is directly attached to W, X, Y or Z is not the same atom of L or $R^1$ that is directly attached to the oxygen atom of $R^1$—O-L-.

2. The compound or the pharmaceutically acceptable salt or solvate thereof as claimed in claim 1, wherein W, X, Y and Z are each independently N, NH or CH.

3. The compound or the pharmaceutically acceptable salt or solvate thereof as claimed in claim 1, wherein at least two of V, W, X, Y and Z are N or NH.

4. The compound or the pharmaceutically acceptable salt or solvate thereof as claimed in claim 1, wherein the group $R^1$—O-L-, including any optional substituents, contains only atoms selected from the group consisting of carbon, hydrogen, oxygen and halogen atoms.

5. The compound or the pharmaceutically acceptable salt or solvate thereof as claimed in claim 1, wherein the group

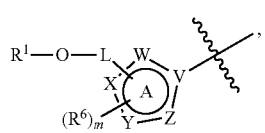

including any optional substituents, contains from 8 to 16 atoms other than hydrogen or halogen.

6. The compound or the pharmaceutically acceptable salt or solvate thereof as claimed in claim 1, wherein each $R^6$ is independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a $C_1$-$C_6$ alkyl, $C_2$-$C_6$ alkenyl, $C_2$-$C_7$ alkynyl or $C_3$-$C_6$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —C≡CH, oxo (=O), or 4- to 6-membered heterocyclic group.

7. The compound or the pharmaceutically acceptable salt or solvate thereof as claimed in claim 1, wherein $R^2$ is an aryl or a heteroaryl group, wherein the aryl or the heteroaryl group is substituted at the α and α' positions, and wherein $R^2$ may optionally be further substituted.

8. The compound or the pharmaceutically acceptable salt or solvate thereof as claimed in claim 7, wherein $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein $R^2$ may optionally be further substituted.

9. The compound or the pharmaceutically acceptable salt or solvate thereof as claimed in claim 1, wherein $R^2$ is a cyclic group substituted at the α-position with a monovalent heterocyclic group or a monovalent aromatic group, wherein a ring atom of the heterocyclic or aromatic group is directly attached to the α-ring atom of the cyclic group, wherein the heterocyclic or aromatic group may optionally be substituted, and wherein the cyclic group is substituted at the α'-position and may optionally be further substituted.

10. The compound or the pharmaceutically acceptable salt or solvate thereof as claimed in claim 1, wherein $R^3$ and $R^4$ are hydrogen.

11. The compound or the pharmaceutically acceptable salt or solvate thereof as claimed in claim 1, wherein Q is O.

12. The compound or the pharmaceutically acceptable salt or solvate thereof as claimed in claim 1, wherein the compound is selected from the group consisting of:

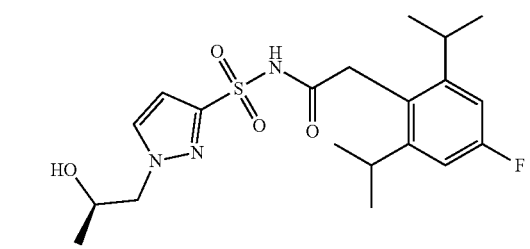
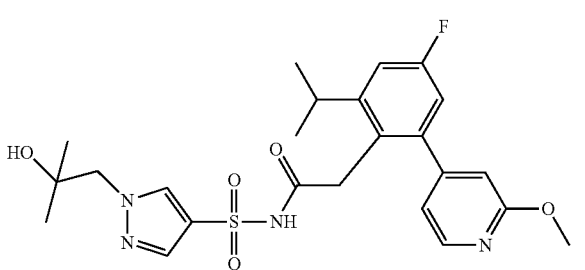
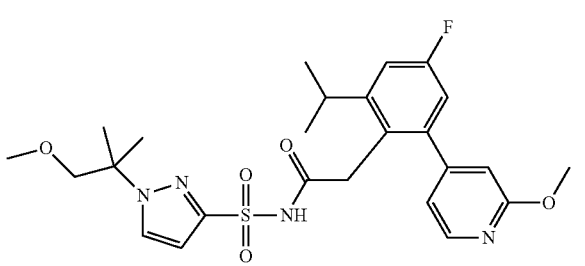
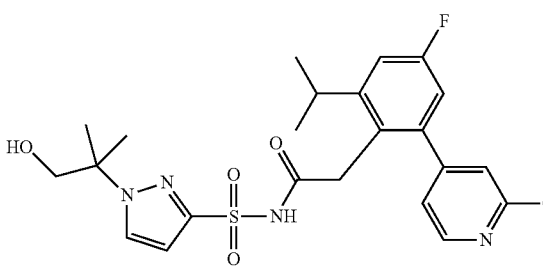
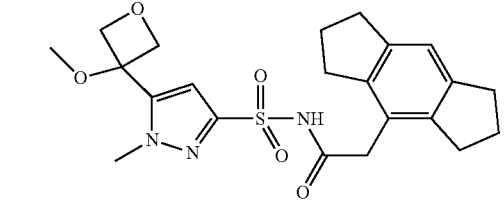
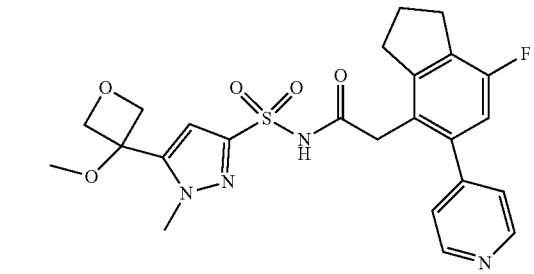
-continued
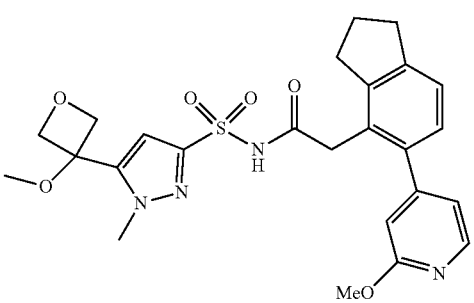
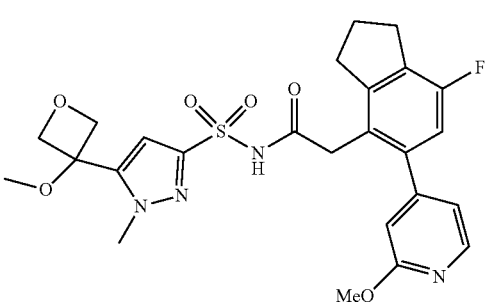
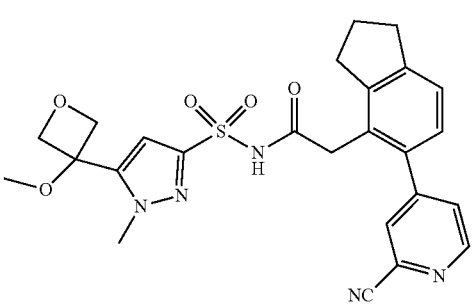
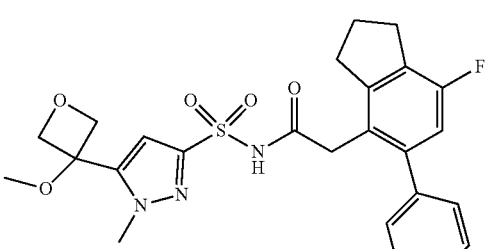
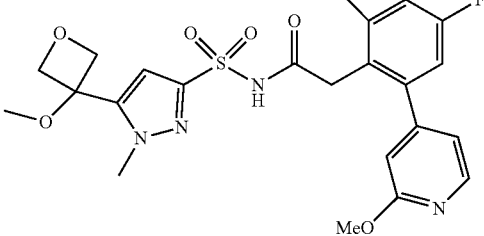

111
-continued
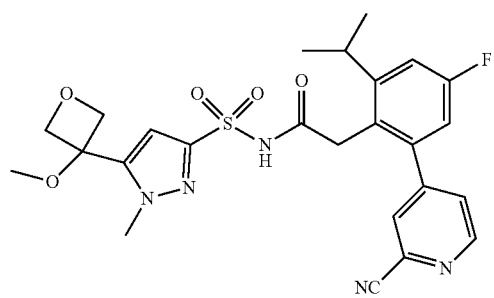
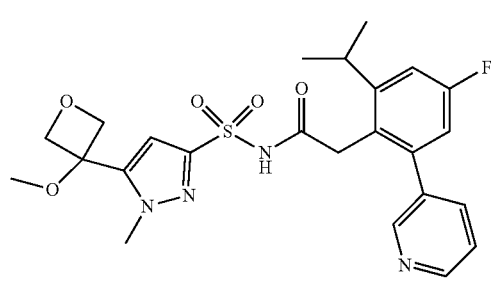
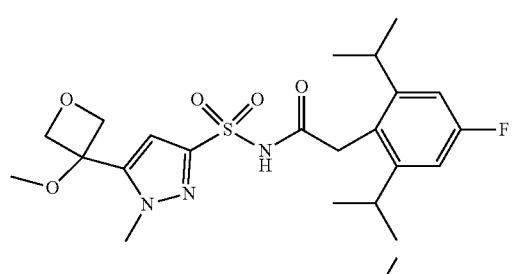
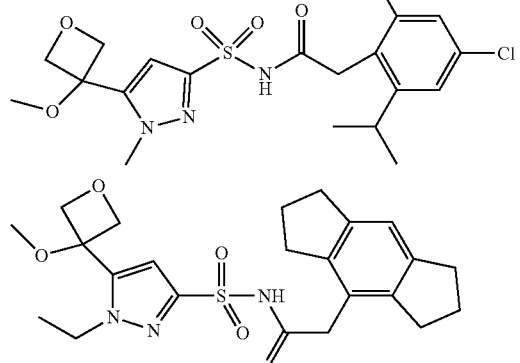
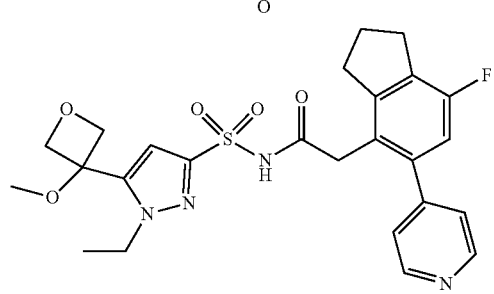
112
-continued
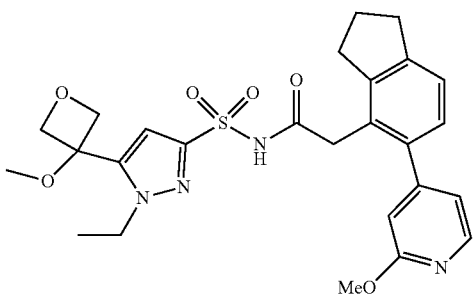
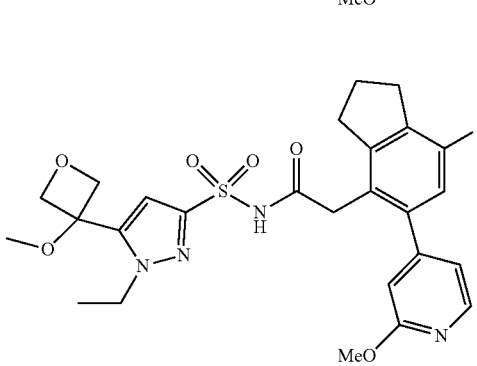
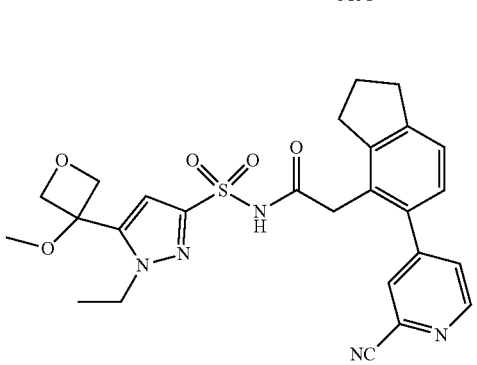
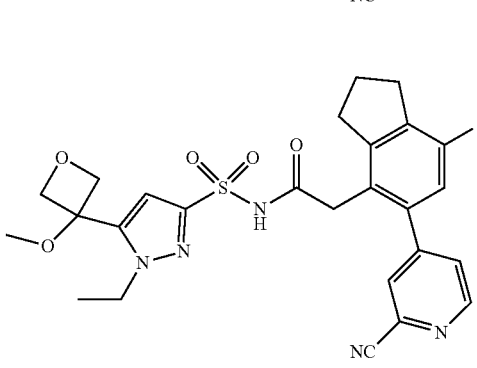
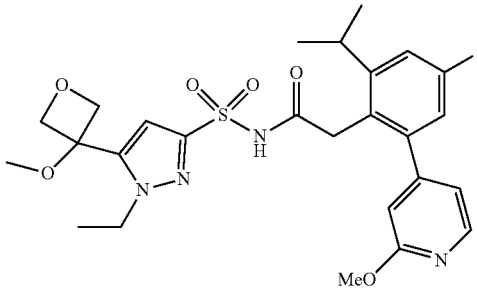

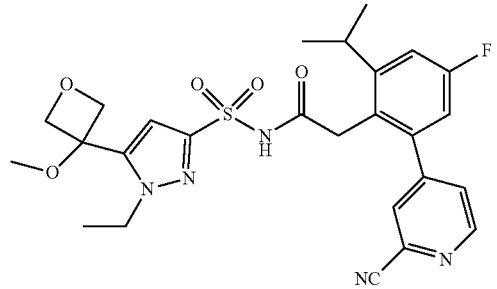
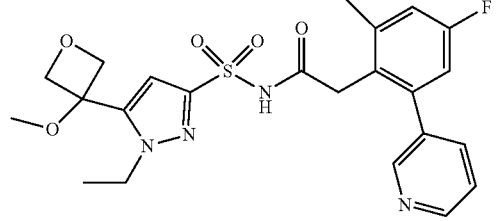
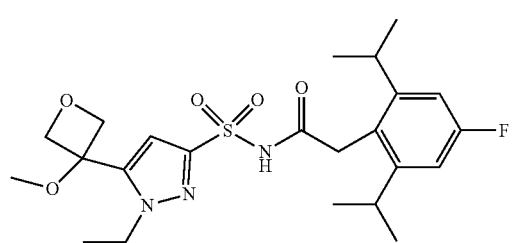
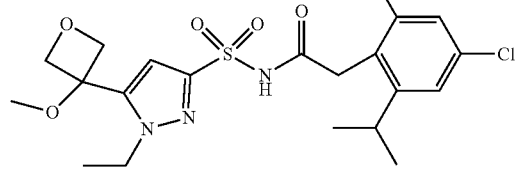
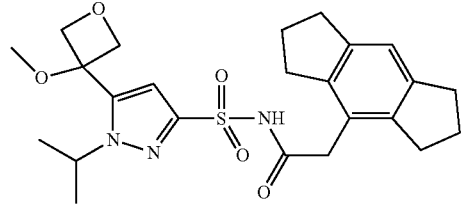
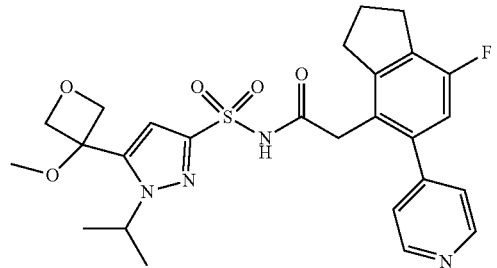
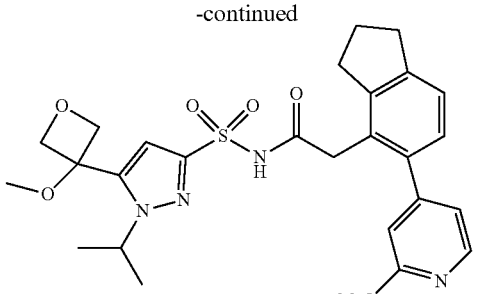
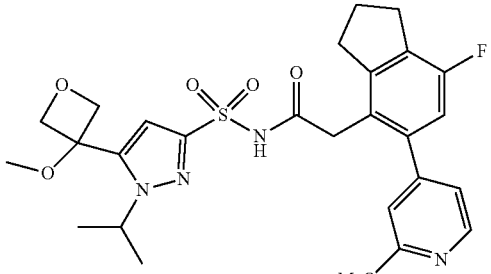
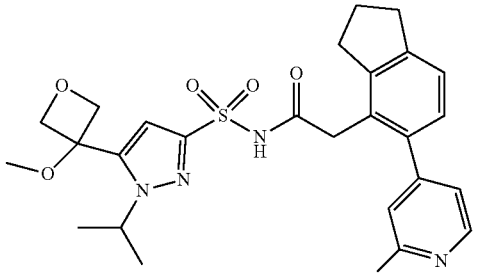
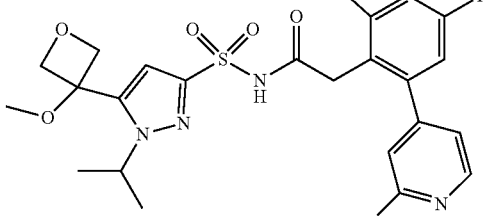
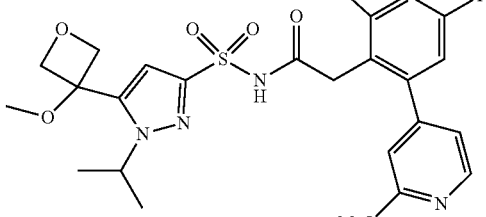
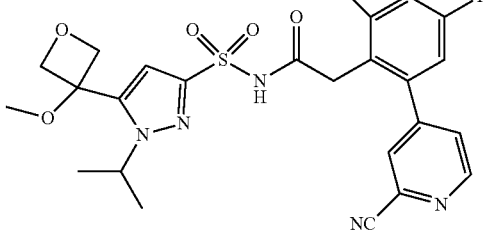

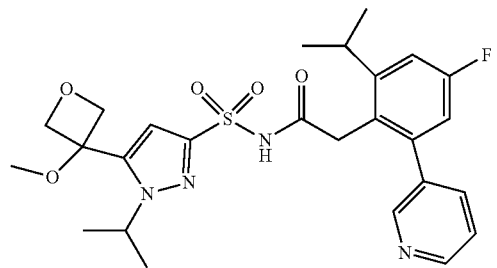
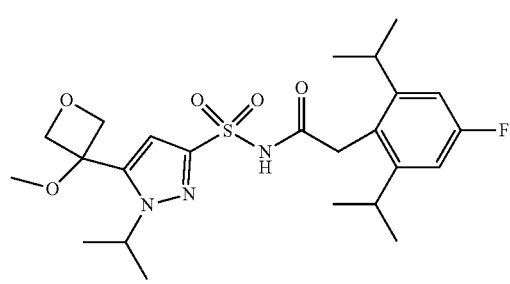
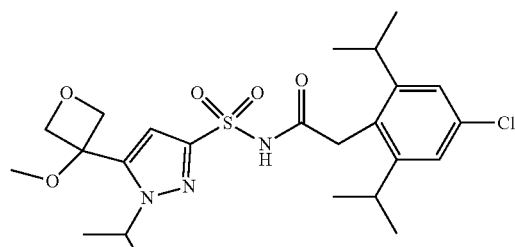
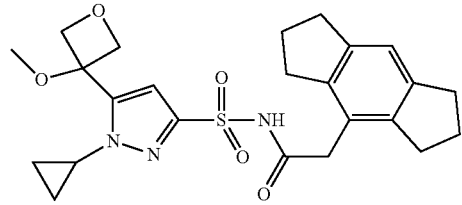
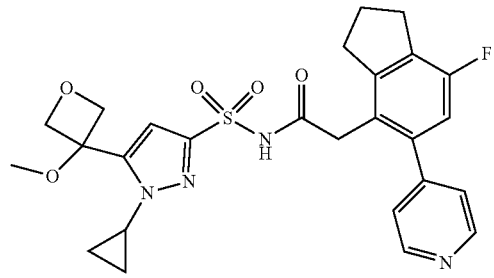
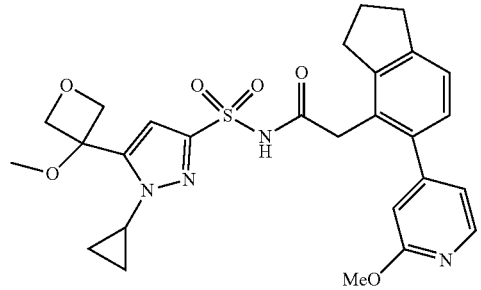
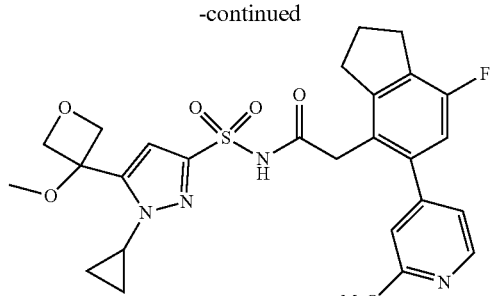
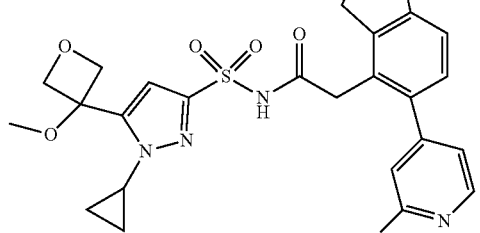
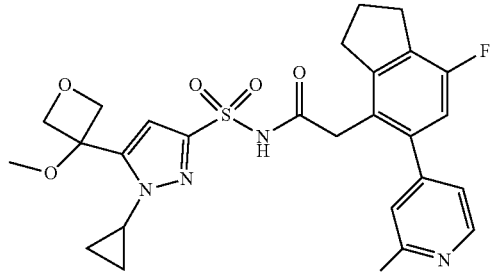
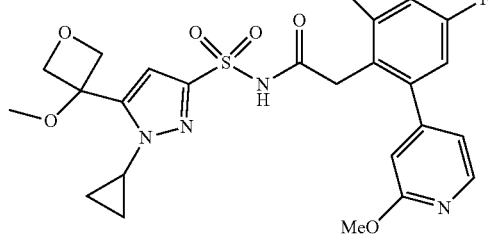
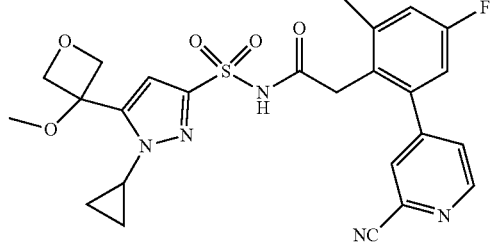
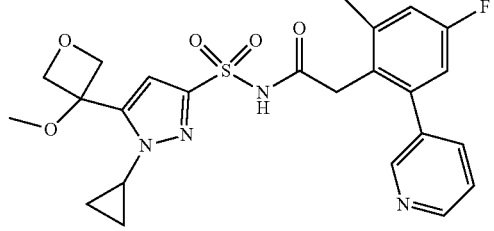

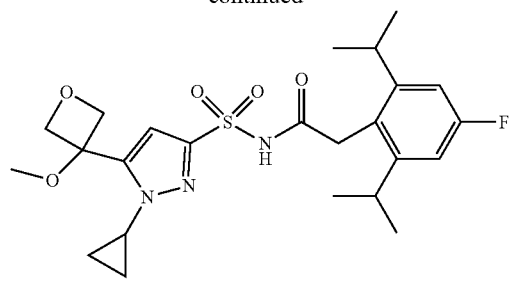
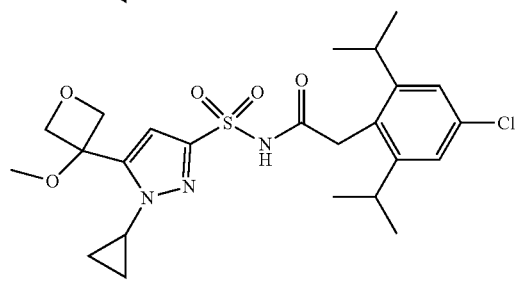
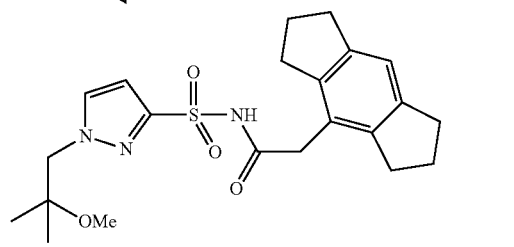
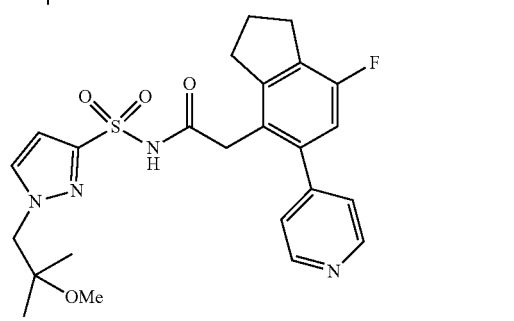
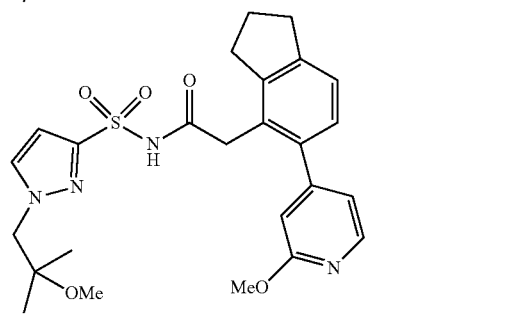
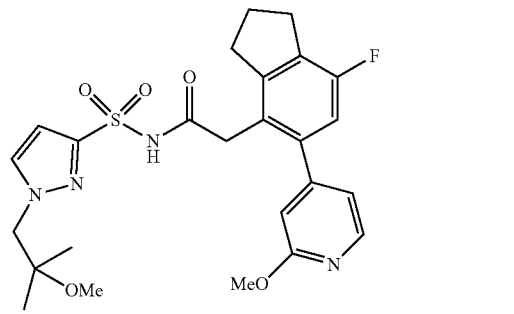
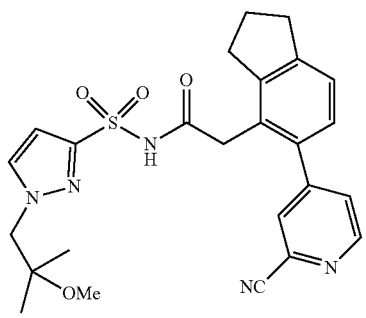
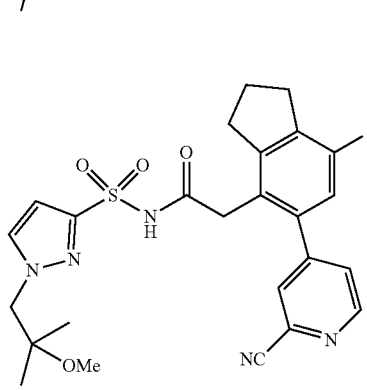
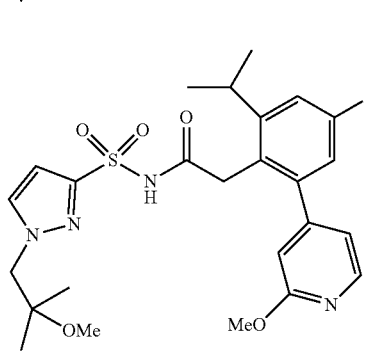
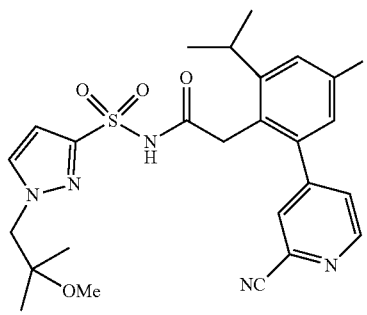
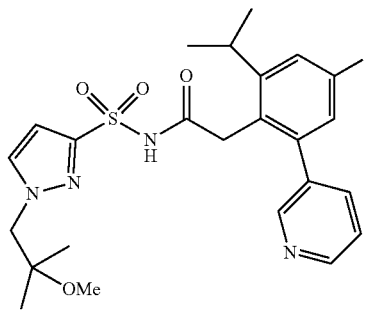

-continued

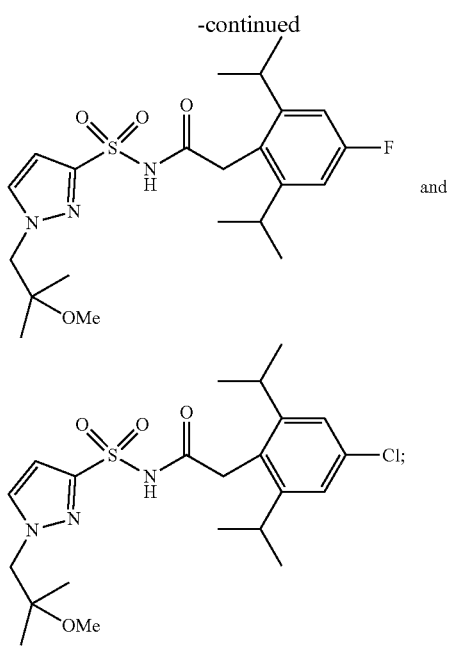

and pharmaceutically acceptable salts and solvates thereof.

13. A pharmaceutical composition comprising the compound or the pharmaceutically acceptable salt or solvate thereof as claimed in claim 1, and a pharmaceutically acceptable excipient.

14. A method of treating, delaying onset of, or reducing risk of a disease, disorder or condition in a subject, the method comprising the step of administering an effective amount of the compound or the pharmaceutically acceptable salt or solvate thereof as claimed in claim 1 to the subject, thereby treating, delaying onset of, or reducing risk of the disease, disorder or condition, wherein the disease, disorder or condition is responsive to NLRP3 inhibition.

15. The method as claimed in claim 14, wherein the disease, disorder or condition is selected from:
(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) graft versus host disease;
(xvi) allodynia; and
(xvii) any disease where an individual has been determined to carry a germline or somatic non-silent mutation in NLRP3.

16. The method as claimed in claim 14, wherein the disease, disorder or condition is selected from:
(i) cryopyrin-associated periodic syndromes (CAPS);
(ii) Muckle-Wells syndrome (MWS);
(iii) familial cold autoinflammatory syndrome (FCAS);
(iv) neonatal onset multisystem inflammatory disease (NOMID);
(v) familial Mediterranean fever (FMF);
(vi) pyogenic arthritis, pyoderma gangrenosum and acne syndrome (PAPA);
(vii) hyperimmunoglobulinemia D and periodic fever syndrome (HIDS);
(viii) Tumour Necrosis Factor (TNF) Receptor-Associated Periodic Syndrome (TRAPS);
(ix) systemic juvenile idiopathic arthritis;
(x) adult-onset Still's disease (AOSD);
(xi) relapsing polychondritis;
(xii) Schnitzler's syndrome;
(xiii) Sweet's syndrome;
(xiv) Behcet's disease;
(xv) anti-synthetase syndrome;
(xvi) deficiency of interleukin 1 receptor antagonist (DIRA); and
(xvii) haploinsufficiency of A20 (HA20).

17. The method as claimed in claim 14, wherein the compound is administered as a pharmaceutical composition further comprising a pharmaceutically acceptable excipient.

18. A method of inhibiting NLRP3 in a subject, comprising administering the compound or the pharmaceutically acceptable salt or solvate thereof as claimed in claim 1 to the subject thereby inhibiting NLRP3.

19. A method of analysing inhibition of NLRP3 or an effect of inhibition of NLRP3 by a compound, comprising contacting a cell or non-human animal with the compound or the pharmaceutically acceptable salt or solvate thereof as claimed in claim 1, and analysing inhibition of NLRP3 or an effect of inhibition of NLRP3 in the cell or non-human animal by the compound.

* * * * *

UNITED STATES PATENT AND TRADEMARK OFFICE
CERTIFICATE OF CORRECTION

PATENT NO. : 11,834,433 B2
APPLICATION NO. : 16/977251
DATED : December 5, 2023
INVENTOR(S) : David Miller et al.

It is certified that error appears in the above-identified patent and that said Letters Patent is hereby corrected as shown below:

In the Claims

In Column 107, Line 24, Claim 1, delete "–$OR_5$, –$NHR_5$" and insert -- –$OR^5$, –$NHR^5$ --, therefor.

In Column 107, Line 26, Claim 1, delete "–$OR_5$, –$NHR_5$" and insert -- –$OR^5$, –$NHR^5$ --, therefor.

In Column 108, Line 27, Claim 6, delete "$C_2$-$C_7$" and insert -- $C_2$-$C_6$ --, therefor.

Signed and Sealed this
Ninth Day of April, 2024

Katherine Kelly Vidal
*Director of the United States Patent and Trademark Office*